(12) United States Patent
Kusner et al.

(10) Patent No.: US 11,485,968 B2
(45) Date of Patent: *Nov. 1, 2022

(54) MICROFLUIDIC CARTRIDGE FOR PROCESSING AND DETECTING NUCLEIC ACIDS

(71) Applicant: NeuMoDx Molecular, Inc., Ann Arbor, MI (US)

(72) Inventors: Michael T. Kusner, Ann Arbor, MI (US); Sundaresh Brahmasandra, Ann Arbor, MI (US); Jeffrey Williams, Ann Arbor, MI (US); Robert Jaekel, Ann Arbor, MI (US)

(73) Assignee: NeuMoDx Molecular, Inc., Ann Arbor, MI (US)

( * ) Notice: Subject to any disclaimer, the term of this patent is extended or adjusted under 35 U.S.C. 154(b) by 511 days.

This patent is subject to a terminal disclaimer.

(21) Appl. No.: 15/808,183

(22) Filed: Nov. 9, 2017

(65) Prior Publication Data

US 2018/0066248 A1    Mar. 8, 2018

Related U.S. Application Data

(63) Continuation-in-part of application No. 15/407,160, filed on Jan. 16, 2017, now Pat. No. 10,557,132, and
(Continued)

(51) Int. Cl.
*B01L 3/00* (2006.01)
*B01L 7/00* (2006.01)
(Continued)

(52) U.S. Cl.
CPC .......... *C12N 15/1013* (2013.01); *B01L 3/502* (2013.01); *B01L 3/508* (2013.01);
(Continued)

(58) Field of Classification Search
None
See application file for complete search history.

(56) References Cited

U.S. PATENT DOCUMENTS

| | | |
|---|---|---|
| 776,747 A | 12/1904 | Kling |
| 778,036 A | 12/1904 | Hepp et al. |
| (Continued) | | |

FOREIGN PATENT DOCUMENTS

| | | |
|---|---|---|
| CN | 101432698 | 5/2009 |
| CN | 1773190 | 5/2010 |
| (Continued) | | |

OTHER PUBLICATIONS

Compton, Cancer and Metastasis Rev., vol. 11, pp. 105-119 (1992).
(Continued)

*Primary Examiner* — Liban M Hassan
(74) *Attorney, Agent, or Firm* — Sterne, Kessler, Goldstein & Fox P.L.L.C.

(57) ABSTRACT

A system, configured to facilitate processing and detection of nucleic acids, the system comprising a process fluid container and a cartridge comprising: a top layer, a set of sample port-reagent port pairs, a shared fluid port, a vent region, a heating region, and a set of detection chambers; an intermediate substrate, coupled to the top layer comprising a waste chamber; an elastomeric layer, partially situated on the intermediate substrate; and a set of fluidic pathways, each formed by at least a portion of the top layer and a portion of the elastomeric layer, wherein each fluidic pathway is fluidically coupled to a sample port-reagent port pair, the shared fluid port, and a detection chamber, comprises a portion passing through the heating region, and is configured to be occluded upon deformation of the elastomeric layer, to transfer a waste fluid to the waste chamber, and to pass through the vent region.

15 Claims, 26 Drawing Sheets

Related U.S. Application Data a continuation-in-part of application No. 15/249,771, filed on Aug. 29, 2016, which is a continuation of application No. 15/134,765, filed on Apr. 21, 2016, now Pat. No. 10,041,062, which is a continuation of application No. 14/704,215, filed on May 5, 2015, now Pat. No. 9,441,219, which is a continuation of application No. 13/766,359, filed on Feb. 13, 2013, now Pat. No. 9,050,594, and a continuation of application No. 13/765,996, filed on Feb. 13, 2013, now Pat. No. 9,738,887, said application No. 15/407,160 is a continuation of application No. 13/765,996, filed on Feb. 13, 2013, now Pat. No. 9,738,887.

(60) Provisional application No. 62/419,578, filed on Nov. 9, 2016, provisional application No. 61/667,606, filed on Jul. 3, 2012, provisional application No. 61/598,240, filed on Feb. 13, 2012.

(51) Int. Cl.

| | |
|---|---|
| *B01L 9/00* | (2006.01) |
| *C12N 15/10* | (2006.01) |
| *C12Q 1/6806* | (2018.01) |
| *C12M 3/00* | (2006.01) |
| *C12Q 1/68* | (2018.01) |
| *C12M 1/12* | (2006.01) |
| *B81C 3/00* | (2006.01) |
| *C12M 3/06* | (2006.01) |
| *B81C 1/00* | (2006.01) |
| *B29C 65/48* | (2006.01) |
| *B29C 65/00* | (2006.01) |
| *B29L 31/00* | (2006.01) |
| *B29C 65/60* | (2006.01) |
| *B29C 65/08* | (2006.01) |
| *C12Q 1/686* | (2018.01) |
| *B29K 21/00* | (2006.01) |
| *C12N 13/00* | (2006.01) |
| *C12Q 1/6813* | (2018.01) |

(52) U.S. Cl.
CPC ......... *B01L 3/5027* (2013.01); *B01L 3/50273* (2013.01); *B01L 3/502707* (2013.01); *B01L 3/502738* (2013.01); *B01L 3/527* (2013.01); *B01L 3/567* (2013.01); *B01L 7/525* (2013.01); *B81C 1/00119* (2013.01); *B81C 3/001* (2013.01); *C12M 23/16* (2013.01); *C12M 23/42* (2013.01); *C12M 25/02* (2013.01); *C12Q 1/68* (2013.01); *C12Q 1/6806* (2013.01); *B01L 3/5025* (2013.01); *B01L 3/502715* (2013.01); *B01L 3/502723* (2013.01); *B01L 3/502746* (2013.01); *B01L 3/502761* (2013.01); *B01L 3/523* (2013.01); *B01L 7/52* (2013.01); *B01L 2200/025* (2013.01); *B01L 2200/0605* (2013.01); *B01L 2200/0615* (2013.01); *B01L 2200/0668* (2013.01); *B01L 2200/0684* (2013.01); *B01L 2200/0689* (2013.01); *B01L 2200/10* (2013.01); *B01L 2200/12* (2013.01); *B01L 2200/142* (2013.01); *B01L 2300/021* (2013.01); *B01L 2300/022* (2013.01); *B01L 2300/044* (2013.01); *B01L 2300/06* (2013.01); *B01L 2300/0609* (2013.01); *B01L 2300/0627* (2013.01); *B01L 2300/0636* (2013.01); *B01L 2300/0672* (2013.01); *B01L 2300/0681* (2013.01); *B01L 2300/087* (2013.01); *B01L 2300/0809* (2013.01); *B01L 2300/0816* (2013.01); *B01L 2300/0861* (2013.01); *B01L 2300/0864* (2013.01); *B01L 2300/0867* (2013.01); *B01L 2300/0883* (2013.01); *B01L 2300/0887* (2013.01); *B01L 2300/0893* (2013.01); *B01L 2300/123* (2013.01); *B01L 2300/14* (2013.01); *B01L 2300/16* (2013.01); *B01L 2300/1822* (2013.01); *B01L 2300/1827* (2013.01); *B01L 2400/043* (2013.01); *B01L 2400/0406* (2013.01); *B01L 2400/0478* (2013.01); *B01L 2400/0481* (2013.01); *B01L 2400/0487* (2013.01); *B01L 2400/065* (2013.01); *B01L 2400/0622* (2013.01); *B01L 2400/0655* (2013.01); *B01L 2400/0694* (2013.01); *B01L 2400/086* (2013.01); *B29C 65/08* (2013.01); *B29C 65/484* (2013.01); *B29C 65/606* (2013.01); *B29C 66/1122* (2013.01); *B29C 66/21* (2013.01); *B29C 66/3022* (2013.01); *B29C 66/542* (2013.01); *B29C 66/71* (2013.01); *B29C 66/81423* (2013.01); *B29C 66/8322* (2013.01); *B29K 2021/00* (2013.01); *B29L 2031/756* (2013.01); *B81B 2201/054* (2013.01); *B81C 2203/032* (2013.01); *C12N 13/00* (2013.01); *C12Q 1/686* (2013.01); *C12Q 1/6813* (2013.01)

(56) References Cited

U.S. PATENT DOCUMENTS

| | | |
|---|---|---|
| 3,963,151 A | 6/1976 | North, Jr. |
| 5,681,529 A | 10/1997 | Taguchi et al. |
| 5,725,831 A | 3/1998 | Reichler et al. |
| 5,750,338 A | 5/1998 | Collins et al. |
| 5,783,148 A | 7/1998 | Cottingham et al. |
| 5,824,478 A | 10/1998 | Mueller |
| 5,853,667 A | 12/1998 | Seaton et al. |
| 5,863,502 A | 1/1999 | Southgate et al. |
| 6,168,948 B1 | 1/2001 | Anderson et al. |
| 6,331,266 B1 | 12/2001 | Powell et al. |
| 6,368,871 B1 | 4/2002 | Christel et al. |
| 6,374,684 B1 | 4/2002 | Dority |
| 6,374,685 B1 | 4/2002 | Daly |
| 6,431,476 B1 | 8/2002 | Taylor et al. |
| 6,440,725 B1 | 8/2002 | Pourahmadi et al. |
| 6,664,104 B2 | 12/2003 | Pourahmadi et al. |
| 6,692,700 B2 | 2/2004 | Handique |
| 6,818,185 B1 | 11/2004 | Petersen et al. |
| 6,852,287 B2 | 2/2005 | Ganesan |
| 6,860,993 B2 | 3/2005 | Effenhauser et al. |
| 6,872,315 B2 | 3/2005 | Effenhauser et al. |
| 6,878,540 B2 | 4/2005 | Pourahmadi et al. |
| 6,887,693 B2 | 5/2005 | McMillan et al. |
| 6,893,879 B2 | 5/2005 | Petersen et al. |
| 6,899,838 B2 | 5/2005 | Lastovich |
| 6,987,018 B2 | 1/2006 | Taylor et al. |
| 7,052,268 B2 | 5/2006 | Powell et al. |
| 7,135,144 B2 | 11/2006 | Christel et al. |
| 7,186,383 B2 * | 3/2007 | Webster ............ B01L 3/50273 422/505 |
| 7,192,557 B2 | 3/2007 | Wu et al. |
| 7,252,501 B2 | 8/2007 | Pruden et al. |
| 7,270,786 B2 | 9/2007 | Parunak et al. |
| 7,323,140 B2 | 1/2008 | Handique et al. |
| 7,332,130 B2 | 2/2008 | Handique |
| 7,372,616 B2 | 5/2008 | Bang et al. |
| 7,445,901 B2 | 11/2008 | Kudlicki et al. |
| 7,473,397 B2 | 1/2009 | Griffin et al. |
| 7,556,858 B2 | 7/2009 | Rasmussen et al. |
| 7,569,346 B2 | 8/2009 | Petersen et al. |
| 7,580,533 B2 | 8/2009 | Schwartz |
| 7,666,681 B2 | 2/2010 | Ammann et al. |
| 7,674,431 B2 | 3/2010 | Ganesan |
| 7,682,820 B2 | 3/2010 | Bader |
| 7,704,735 B2 | 4/2010 | Facer et al. |

(56) References Cited

U.S. PATENT DOCUMENTS

| | | |
|---|---|---|
| 7,731,906 B2 | 6/2010 | Handique et al. |
| 7,738,094 B2 | 6/2010 | Goldberg |
| 7,763,209 B2 | 7/2010 | Haley |
| 7,767,447 B2 | 8/2010 | Breidenthal et al. |
| 7,820,030 B2 | 10/2010 | Althaus et al. |
| 7,863,035 B2 | 1/2011 | Clemens et al. |
| 7,906,758 B2 | 3/2011 | Stults et al. |
| 7,914,994 B2 | 3/2011 | Petersen et al. |
| 7,935,537 B2 | 5/2011 | Haley |
| 7,943,388 B2 | 5/2011 | Baetzold et al. |
| 7,955,798 B2 | 6/2011 | Mauritz |
| 7,955,864 B2 | 6/2011 | Cox et al. |
| 7,964,413 B2 | 6/2011 | Macioszek et al. |
| 7,987,022 B2 | 7/2011 | Handique et al. |
| 7,995,798 B2 | 8/2011 | Krupnik et al. |
| 7,998,708 B2 | 8/2011 | Handique et al. |
| 8,003,329 B2 | 8/2011 | Macevicz |
| 8,008,046 B2 | 8/2011 | Maltezos et al. |
| 8,008,066 B2 | 8/2011 | Lair et al. |
| 8,043,581 B2 | 10/2011 | Ganesan |
| 8,048,375 B2 | 11/2011 | Breidenthal et al. |
| 8,048,386 B2 | 11/2011 | Dority et al. |
| 8,052,929 B2 | 11/2011 | Breidenthal et al. |
| 8,057,446 B2 | 11/2011 | Kane et al. |
| 8,088,616 B2 | 1/2012 | Handique |
| 8,105,477 B2 | 1/2012 | Althaus et al. |
| 8,105,783 B2 | 1/2012 | Handique |
| 8,110,158 B2 | 2/2012 | Handique |
| 8,133,671 B2 | 3/2012 | Williams et al. |
| 8,163,535 B2 | 4/2012 | Reed et al. |
| 8,168,134 B2 | 5/2012 | Lehto |
| 8,182,763 B2 | 5/2012 | Duffy et al. |
| 8,183,359 B2 | 5/2012 | Becker et al. |
| 8,187,557 B2 | 5/2012 | Van Atta et al. |
| 8,247,176 B2 | 8/2012 | Petersen et al. |
| 8,248,597 B2 | 8/2012 | Goldberg |
| 8,268,245 B2 | 9/2012 | Wahl |
| 8,268,603 B2 | 9/2012 | Taylor et al. |
| 8,273,308 B2 | 9/2012 | Handique et al. |
| 8,287,820 B2 | 10/2012 | Williams et al. |
| 8,288,520 B2 | 10/2012 | Eder et al. |
| 8,323,584 B2 | 12/2012 | Ganesan |
| 8,323,899 B2 | 12/2012 | Sherman et al. |
| 8,323,900 B2 | 12/2012 | Handique et al. |
| 8,324,372 B2 | 12/2012 | Brahmasandra et al. |
| 8,349,564 B2 | 1/2013 | Macioszek et al. |
| 8,388,908 B2 | 3/2013 | Blaga et al. |
| 8,394,336 B2 | 3/2013 | Curcio |
| 8,404,198 B2 | 3/2013 | Amshey et al. |
| 8,414,845 B2 | 4/2013 | Chen et al. |
| 8,415,103 B2 | 4/2013 | Handique |
| 8,420,015 B2 | 4/2013 | Ganesan et al. |
| 8,431,413 B2 | 4/2013 | Dority et al. |
| 8,440,149 B2 | 5/2013 | Handique |
| 8,449,833 B2 | 5/2013 | Nieuwenhuis |
| 8,470,586 B2 | 6/2013 | Wu et al. |
| 8,470,588 B2 | 6/2013 | Boehm et al. |
| 8,473,104 B2 | 6/2013 | Handique et al. |
| 8,480,976 B2 | 7/2013 | Breidenthal et al. |
| 8,491,178 B2 | 7/2013 | Breidenthal et al. |
| 8,501,461 B2 | 8/2013 | Knight et al. |
| 8,506,908 B2 | 8/2013 | Benn et al. |
| 8,513,962 B2 | 8/2013 | Kiyokawa et al. |
| 8,640,555 B2 | 2/2014 | Zenhausern et al. |
| 8,642,787 B2 | 2/2014 | Fukushima et al. |
| 8,672,532 B2 | 3/2014 | Jovanovich et al. |
| 8,709,787 B2 | 4/2014 | Handique |
| 8,734,761 B2 | 5/2014 | Willard et al. |
| 8,738,106 B2 | 5/2014 | Rabinowitz et al. |
| 8,852,862 B2 | 10/2014 | Wu et al. |
| 9,040,288 B2 | 5/2015 | Handique et al. |
| 9,050,594 B2 | 6/2015 | Williams et al. |
| 9,101,930 B2 | 8/2015 | Williams et al. |
| 9,180,451 B2 | 11/2015 | Ziglioli et al. |
| 9,238,809 B2 | 1/2016 | Khripin et al. |
| 9,339,812 B2 | 5/2016 | Williams et al. |
| 9,382,532 B2 | 7/2016 | Brahmasandra et al. |
| 9,618,506 B2 | 4/2017 | Lowe et al. |
| 9,663,779 B2 | 5/2017 | Fabis et al. |
| 9,789,481 B2 | 10/2017 | Petersen et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,590,410 B2 | 3/2020 | Brahmasandra et al. |
| 10,604,788 B2 | 3/2020 | Wu et al. |
| 2002/0042125 A1 | 4/2002 | Petersen et al. |
| 2002/0045246 A1 | 4/2002 | McMillan et al. |
| 2002/0055167 A1 | 5/2002 | Pourahmadi et al. |
| 2002/0087110 A1 | 7/2002 | Effenhauser et al. |
| 2002/0110492 A1 | 8/2002 | Handique |
| 2002/0141903 A1 | 10/2002 | Parunak et al. |
| 2002/0142471 A1 | 10/2002 | Handique et al. |
| 2002/0142482 A1 | 10/2002 | Wu et al. |
| 2002/0160518 A1 | 10/2002 | Hayenga et al. |
| 2002/0175079 A1 | 11/2002 | Christel et al. |
| 2002/0187547 A1 | 12/2002 | Taylor et al. |
| 2003/0049174 A1 | 3/2003 | Ganesan |
| 2003/0162304 A1 | 8/2003 | Dority et al. |
| 2003/0170686 A1 | 9/2003 | Hoet et al. |
| 2004/0007796 A1 | 1/2004 | Lastovich |
| 2004/0018611 A1 | 1/2004 | Ward et al. |
| 2004/0032001 A1 | 2/2004 | Gilmer et al. |
| 2004/0053268 A1 | 3/2004 | Karlsen |
| 2004/0138154 A1 | 7/2004 | Yu et al. |
| 2004/0166031 A1 | 8/2004 | Taylor et al. |
| 2004/0186111 A1 | 9/2004 | Sun et al. |
| 2004/0209331 A1 | 10/2004 | Ririe |
| 2004/0219070 A1 | 11/2004 | Handique |
| 2004/0222349 A1 | 11/2004 | Powell et al. |
| 2005/0006309 A1 | 1/2005 | Effenhauser et al. |
| 2005/0106742 A1 | 5/2005 | Wahl |
| 2005/0112754 A1 | 5/2005 | Yoon et al. |
| 2005/0152808 A1 | 7/2005 | Ganesan |
| 2005/0194316 A1 | 9/2005 | Pourahmadi et al. |
| 2005/0205199 A1 | 9/2005 | Green |
| 2005/0214927 A1 | 9/2005 | Haley |
| 2005/0250199 A1 | 11/2005 | Anderson et al. |
| 2006/0030038 A1 | 2/2006 | Taylor et al. |
| 2006/0036348 A1 | 2/2006 | Handique et al. |
| 2006/0046262 A1 | 3/2006 | Mauritz |
| 2006/0099719 A1 | 5/2006 | Curcio |
| 2006/0205085 A1 | 9/2006 | Handique et al. |
| 2006/0207891 A1 | 9/2006 | Althaus et al. |
| 2006/0211130 A1 | 9/2006 | Macioszek et al. |
| 2007/0031282 A1* | 2/2007 | Zucchelli ............. G01N 35/028 422/400 |
| 2007/0062583 A1 | 3/2007 | Cox et al. |
| 2007/0184463 A1 | 8/2007 | Molho et al. |
| 2007/0243600 A1 | 10/2007 | Lair et al. |
| 2008/0014114 A1 | 1/2008 | Van et al. |
| 2008/0050804 A1 | 2/2008 | Handique et al. |
| 2008/0057572 A1* | 3/2008 | Petersen .................. B01L 7/52 435/306.1 |
| 2008/0160601 A1 | 7/2008 | Handique |
| 2008/0182301 A1 | 7/2008 | Handique et al. |
| 2008/0212069 A1 | 9/2008 | Goldberg et al. |
| 2008/0213755 A1 | 9/2008 | Geiser et al. |
| 2008/0217246 A1 | 9/2008 | Benn et al. |
| 2008/0219894 A1 | 9/2008 | Ganesan et al. |
| 2008/0227189 A1 | 9/2008 | Bader |
| 2008/0241569 A1 | 10/2008 | Qin et al. |
| 2008/0262213 A1 | 10/2008 | Wu et al. |
| 2008/0280285 A1 | 11/2008 | Chen et al. |
| 2009/0047713 A1 | 2/2009 | Handique |
| 2009/0057550 A1 | 3/2009 | Stults et al. |
| 2009/0097725 A1 | 4/2009 | Krupnik et al. |
| 2009/0130745 A1 | 5/2009 | Williams et al. |
| 2009/0136386 A1 | 5/2009 | Duffy et al. |
| 2009/0136913 A1 | 5/2009 | Breidenthal et al. |
| 2009/0142745 A1 | 6/2009 | Breidenthal et al. |
| 2009/0155123 A1 | 6/2009 | Williams et al. |
| 2009/0191643 A1 | 7/2009 | Boehm et al. |
| 2009/0215125 A1 | 8/2009 | Reed et al. |
| 2009/0269248 A1 | 10/2009 | Falb et al. |

(56) References Cited

U.S. PATENT DOCUMENTS

| | | |
|---|---|---|
| 2010/0009351 A1 | 1/2010 | Brahmasandra et al. |
| 2010/0029544 A1 | 2/2010 | Cheng et al. |
| 2010/0068706 A1 | 3/2010 | Pourahmadi et al. |
| 2010/0075311 A1 | 3/2010 | Barrault et al. |
| 2010/0075336 A1 | 3/2010 | Knight et al. |
| 2010/0120129 A1 | 5/2010 | Amshey et al. |
| 2010/0158754 A1 | 6/2010 | Ganesan |
| 2010/0159463 A1 | 6/2010 | Eder et al. |
| 2010/0159561 A1 | 6/2010 | Becker et al. |
| 2010/0166612 A1 | 7/2010 | Lehto |
| 2010/0261197 A1 | 10/2010 | Goldberg et al. |
| 2010/0279430 A1 | 11/2010 | Haley |
| 2010/0300563 A1 | 12/2010 | Ramunas et al. |
| 2011/0003281 A1 | 1/2011 | Woudenberg et al. |
| 2011/0020793 A1 | 1/2011 | Macevicz |
| 2011/0038768 A1 | 2/2011 | Handique |
| 2011/0039345 A1 | 2/2011 | Althaus et al. |
| 2011/0053169 A1 | 3/2011 | Macioszek et al. |
| 2011/0100101 A1 | 5/2011 | Zenhausern et al. |
| 2011/0165562 A1 | 7/2011 | Pourahmadi et al. |
| 2011/0189661 A1 | 8/2011 | Breidenthal et al. |
| 2011/0193017 A1 | 8/2011 | Snelling et al. |
| 2011/0201099 A1 | 8/2011 | Anderson et al. |
| 2011/0207140 A1 | 8/2011 | Handique et al. |
| 2011/0275087 A1 | 11/2011 | Breidenthal et al. |
| 2012/0022695 A1 | 1/2012 | Handique et al. |
| 2012/0034705 A1 | 2/2012 | Dority et al. |
| 2012/0046203 A1 | 2/2012 | Walsh et al. |
| 2012/0085416 A1 | 4/2012 | Ganesan |
| 2012/0122108 A1 | 5/2012 | Handique |
| 2012/0183454 A1 | 7/2012 | Handique |
| 2012/0231456 A1 | 9/2012 | Breidenthal et al. |
| 2013/0209326 A1 | 8/2013 | Williams et al. |
| 2014/0147892 A1 | 5/2014 | Brahmasandra et al. |

FOREIGN PATENT DOCUMENTS

| | | |
|---|---|---|
| CN | 101842690 | 6/2013 |
| EP | 0707077 | 4/1996 |
| GB | 2125007 | 2/1984 |
| WO | 048164 | 6/2002 |
| WO | 003200 | 1/2004 |
| WO | 064635 | 6/2007 |
| WO | 097342 | 8/2008 |
| WO | 115626 | 9/2008 |
| WO | 022994 | 2/2009 |
| WO | 038536 | 3/2009 |
| WO | 072821 | 7/2010 |
| WO | 121315 | 10/2010 |

OTHER PUBLICATIONS

Oh Tae Jeong et al: "Polyamines Protect Against DNA Strand Breaks and Aid Cell Survival Against Irradiation in *Escherichia coli*", Biotechnology Techniques, vol. 12, No. 10, Oct. 1998 (Oct. 1998), pp. 755-758, XP002599273, ISSN: 0951-208X the whole docu.

Agostino, Luciana D. et al.; "Nuclear Aggregates of Polyamines", IUBMB Life, Taylor and Francis, London, GB LNKD-DOI:10.1080/15216540600662525, vol. 58, No. 2, Feb. 1, 2006 (Feb. 1, 2006), pp. 75-82, XP007914693, ISSN: 1521-6543.

Khan, Ahsan U. et al.; "Spermine and Spermidine Protection of Plasmid DNA Against Single-Strand Breaks Induced by Singlet Oxygen", Proceedings of the National Academy of Sciences of the United States (PNAS), National Academy of Science, US, vol. 89.

Marton, L J et al.; Polyamine-DNA Interactions Possible Site of New Cancer Chemotherapeutical Research (New York) vol. 3, No. 6, 1986, pp. 311-317, XP007914671, ISSN: 0724-8741 p. 311, col. 2, line 26-line 35; figure 1.

\* cited by examiner

SIDE VIEW

TOP VIEW

MICROFLUIDIC CARTRIDGE FOR PROCESSING AND DETECTING NUCLEIC ACIDS

CROSS-REFERENCE TO RELATED APPLICATIONS

This application is a continuation-in-part of U.S. application Ser. No. 15/407,160 filed on 16 Jan. 2017, which is a continuation of U.S. application Ser. No. 13/765,996 filed on 13 Feb. 2013, which claims the benefit of U.S. Provisional Application Ser. No. 61/667,606, filed on 3 Jul. 2012, and U.S. Provisional Application Ser. No. 61/598,240, filed on 13 Feb. 2012, which are herein incorporated in their entirety by this reference.

This application is also a continuation-in-part of U.S. application Ser. No. 15/249,771 filed on 29 Aug. 2016, which is a continuation of co-pending U.S. patent application Ser. No. 15/134,765 filed 21 Apr. 2016, which is a continuation of U.S. patent application Ser. No. 14/704,215, filed 5 May 2015, which is a continuation of U.S. patent application Ser. No. 13/766,359, filed 13 Feb. 2013, which claims the benefit of U.S. Provisional Application Ser. No. 61/667,606, filed on 3 Jul. 2012, and U.S. Provisional Application Ser. No. 61/598,240, filed on 13 Feb. 2012, which are incorporated herein in their entirety by this reference. U.S. application Ser. No. 15/249,771 is also a continuation of co-pending U.S. patent application Ser. No. 15/134,765, filed 21 Apr. 2016, which is a continuation of U.S. patent application Ser. No. 14/704,215, filed 5 May 2015, which claims priority to co-pending U.S. application Ser. No. 13/765,996, filed 13 Feb. 2013, which are incorporated herein in their entirety by this reference.

This application also claims the benefit of U.S. Provisional Application No. 62/419,578, filed 9 Nov. 2016, which is incorporated herein in its entirety by this reference.

TECHNICAL FIELD

This invention relates generally to the molecular diagnostics field, and more specifically to an improved microfluidic cartridge for processing and detecting nucleic acids.

BACKGROUND

Molecular diagnostics is a laboratory discipline that has developed rapidly during the last 25 years. It originated from basic biochemistry and molecular biology research procedures, but now has become an independent discipline focused on routine analysis of nucleic acids (NA), including deoxyribonucleic acid (DNA) and ribonucleic acid (RNA) for diagnostic use in healthcare and other fields requiring nucleic acid analysis. Molecular diagnostic analysis of biological samples can include the detection and/or monitoring of one or more nucleic acid materials present in the specimen. The particular analysis performed may be either qualitative and/or quantitative. Methods of analysis may involve isolation, purification, and amplification of nucleic acid materials, and polymerase chain reaction (PCR) is a common technique used to amplify nucleic acids. Often, a nucleic acid sample to be analyzed is obtained in insufficient quantity, quality, and/or purity, hindering a robust implementation of a diagnostic technique. Current sample processing methods and molecular diagnostic techniques are also labor/time intensive, low throughput, and expensive, and systems of analysis are insufficient. Furthermore, methods of isolation, processing, and amplification are often specific to certain nucleic acid types and not applicable across multiple acid types. Due to these and other deficiencies of current molecular diagnostic systems and methods, there is thus a need for improved devices for processing and amplifying nucleic acids. Thus, there is a need in the molecular diagnostics field to create an improved microfluidic cartridge to facilitate processing and detecting of nucleic acids. This invention provides such a microfluidic cartridge.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Microfluidic Cartridge

Figure 1A:
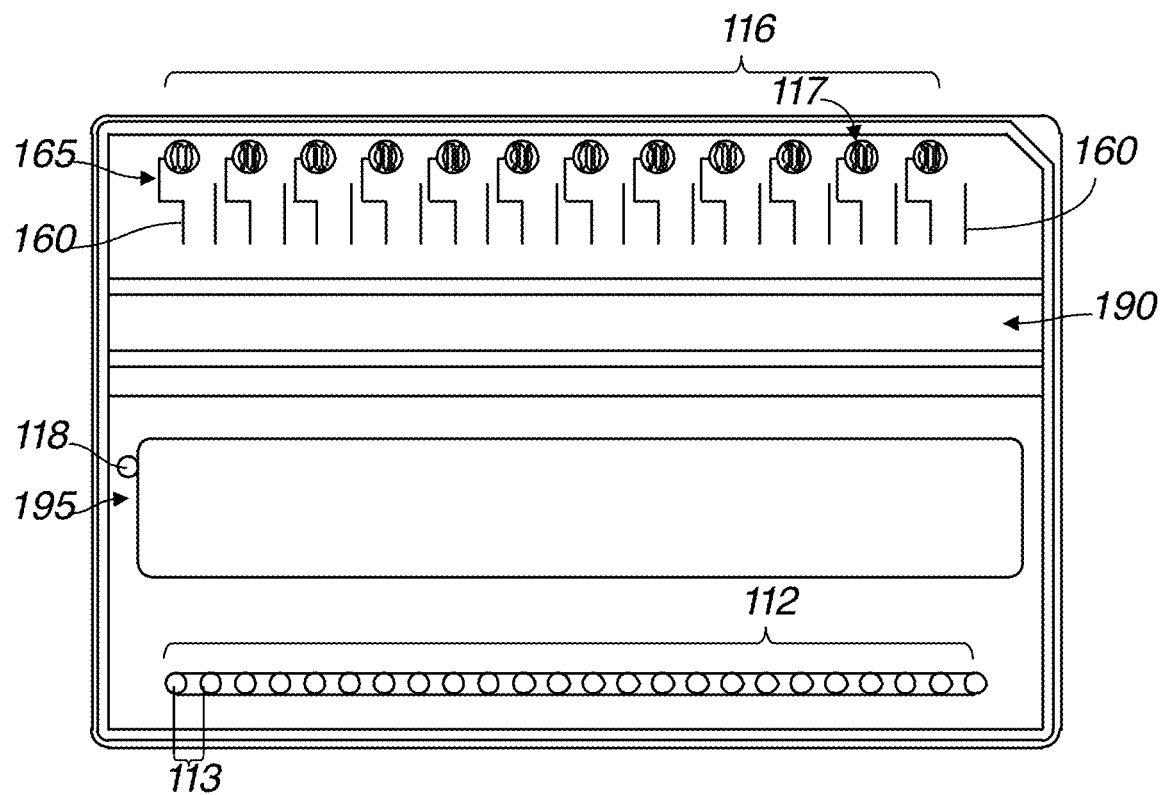
FIGS. 1A-1C depict an embodiment of a microfluidic cartridge (top and side views) and an embodiment of a microfluidic pathway of the microfluidic cartridge.
Figure 1B:
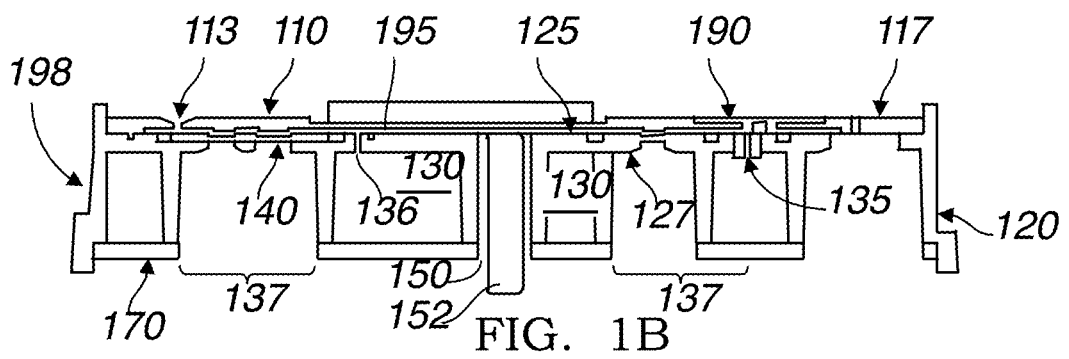
Figure 1C:
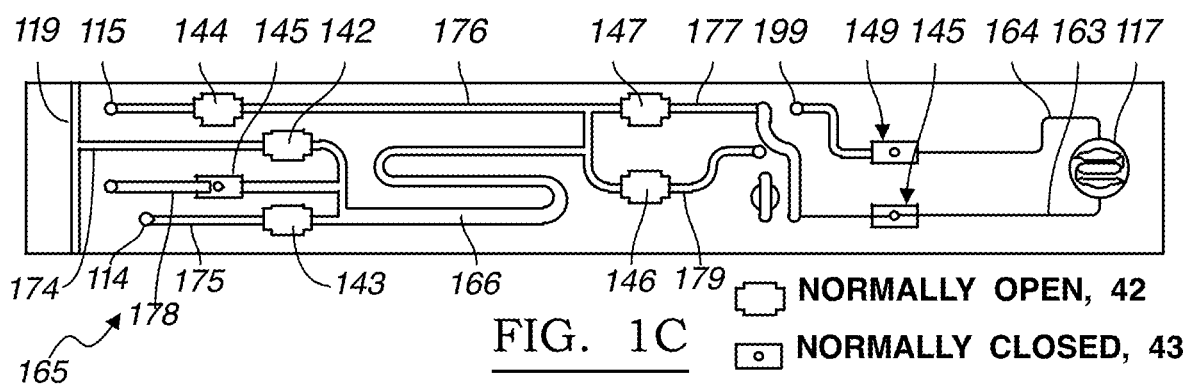

As shown in FIGS. 1A-1C, an embodiment of a microfluidic cartridge 100 for processing and detecting nucleic acids comprises: a top layer 110 comprising a set of sample port-reagent port pairs 112 and a set of detection chambers 116; an intermediate substrate 120, coupled to the top layer 110 and partially separated from the top layer by a film layer 125, configured to form a waste chamber 130; an elastomeric layer 140 partially situated on the intermediate substrate 120; a magnet housing region 150 accessible by a magnet 152 providing a magnetic field 156; and a set of fluidic pathways 160, each formed by at least a portion of the top layer 110, a portion of the film layer 125, and a portion of the elastomeric layer 140. In other embodiments, the microfluidic cartridge 100 may further comprise a bottom layer 170 coupled to the intermediate substrate 120 and configured to seal the waste chamber 130. Furthermore, the top layer 110 of the microfluidic cartridge 100 may further comprise a shared fluid port 118, a vent region 190, and a heating region 195, such that each fluidic pathway 165 in the set of fluidic pathways 160 is fluidically coupled to a sample port-reagent port pair 113, the shared fluid port 118, the waste chamber 130, and a detection chamber 117, comprises a capture segment 166 configured to pass through the heating region and the magnetic field, and is configured to pass through the vent region 190 upstream of the detection chamber 117. Each fluidic pathway 165 thus functions to receive and facilitate processing of a sample fluid containing nucleic acids as it passes through different portions of the fluidic pathway 165. As configured, the microfluidic cartridge 100 can be used to facilitate molecular diagnostic processes and techniques, and preferably conforms to microtiter plate dimensional standards. Alternatively, the microfluidic cartridge 100 may be any appropriate size. In a specific application, the microfluidic cartridge 100 can be used to facilitate a PCR procedure for analysis of a sample containing nucleic acids.

1.1 Microfluidic Cartridge—Top Layer

The top layer 110 of an embodiment of the microfluidic cartridge 100 functions to accommodate elements involved in performing a molecular diagnostic procedure (e.g. PCR), such that a sample containing nucleic acids, passing through the cartridge, can be manipulated by the elements involved in performing the molecular diagnostic procedure. The top layer 110 is preferably composed of a structurally rigid/stiff material with low autofluorescence, such that the top layer 110 does not interfere with sample detection by fluorescence or chemiluminescence techniques, and an appropriate glass transition temperature and chemical compatibility for PCR or other amplification techniques. Preferably, the top layer 110 is composed of a polypropylene-based polymer, but the top layer 110 may alternatively be composed of any appropriate material (e.g. cyclic olefin polymer). In a specific embodiment, the top layer 110 is composed of 1.5 mm thick polypropylene produced by injection molding, with a glass transition temperature between 136 and 163° C. The top layer 110 may alternatively be composed of any appropriate material, for example, a polypropylene based polymer. As shown in FIGS. 1B and 1C, the top layer 110 preferably comprises a set of sample port-reagent port pairs 112, a fluid port 118, a vent region 190, a heating region 195 crossing a capture segment 166 of a fluidic pathway 165, and a set of detection chambers 116.

Each sample-port-reagent port pair 113 of an embodiment of the top layer 110 comprises a sample port 114 and a reagent port 115. The sample port 114 functions to receive a volume of a sample fluid potentially containing the nucleic acids of interest for delivery of the volume of fluid to a portion of a fluidic pathway 165 coupled to the sample port-reagent port pair 113. In a specific embodiment, the volume of a sample fluid is a biological sample with magnetic beads for nucleic acid isolation; however, the volume of fluid comprising a sample fluid may alternatively be any appropriate fluid containing a sample with nucleic acids. Preferably, each sample port 114 is isolated from all other sample ports, in order to prevent cross-contamination between samples of nucleic acids being analyzed. Additionally, each sample port 114 is preferably of an appropriate geometric size and shape to accommodate a standard-size pipette tip used to deliver the volume of a sample fluid without leaking. Alternatively, all or a portion of the sample ports 114 are configured to be coupled to fluid conduits or tubing that deliver the volume of a sample fluid.

Each sample-port reagent port pair 113 of an embodiment of the top layer 110 also comprises a reagent port 115, as shown in FIG. 1A. The reagent port 115 in a sample port-reagent port pair 113 functions to receive a volume of fluid comprising a reagent used in molecular diagnostics, for delivery of the volume of fluid comprising a reagent to a portion of a fluidic pathway 165 coupled to the sample port-reagent port pair 113. In a specific embodiment, the volume of fluid comprising a reagent used in molecular diagnostics is a sample of reconstituted molecular diagnostic reagents mixed with nucleic acids released and isolated using the microfluidic cartridge 100; however, the volume of fluid comprising a reagent used in molecular diagnostics may alternatively be any appropriate fluid comprising reagents used in molecular diagnostics. Preferably, each reagent port 115 is isolated from all other reagent ports, in order to prevent cross-contamination between samples of nucleic acids being analyzed. Additionally, each reagent port 115 is preferably of an appropriate geometric size to accommodate a standard-size pipette tip used to deliver the volume of fluid comprising a reagent used in molecular diagnostics. Alternatively, all or a portion of the reagent ports 115 are configured to be coupled to fluid conduits or tubing that deliver the volume of fluid comprising a reagent used in molecular diagnostics.

Preferably, the set of sample port-reagent port pairs 112 is located near a first edge of the top layer 110, such that the configuration of the sample port-reagent port pairs 112 functions to increase accessibility, for instance, by a pipettor delivering fluids to the microfluidic cartridge 100. In one specific example, the microfluidic cartridge 100 is configured to be aligned within a module, with the set of sample port-reagent port pairs 112 accessible outside of the module, such that a multichannel pipette head can easily access the set of sample port-reagent port pairs 112. Preferably, as shown in FIG. 1A, the set of sample port-reagent port pairs 112 is configured such that the sample ports 114 and the reagent ports 115 alternate along the first edge of the top layer 110. In an alternative embodiment, the set of sample port-reagent port pairs 112 may not be located near an edge of the top layer 110, and may further not be arranged in an alternating fashion.

Figure 2:
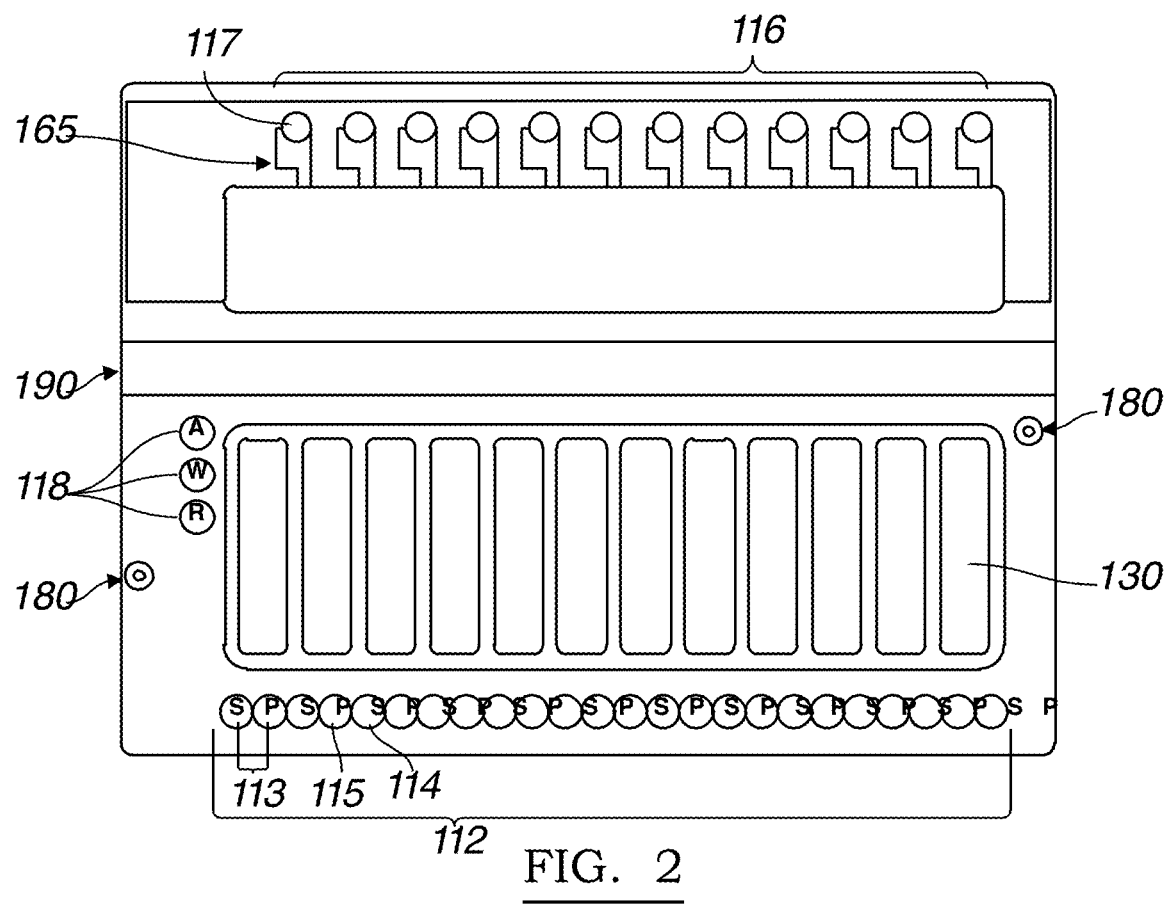
FIG. 2 depicts an alternative embodiment of a microfluidic cartridge (top view) showing individual waste chambers located on the top of cartridge and multiple fluid ports.

The fluid port 118 of the top layer 110 of the microfluidic cartridge functions to receive at least one of a wash fluid, a release fluid, and a gas used in a molecular diagnostic procedure, such as PCR. In an embodiment, the wash fluid, the release fluid, and/or the gas are common to all samples being analyzed during a run of the diagnostic procedure using the microfluidic cartridge 100; in this embodiment, as shown in FIG. 1A, the fluid port 118 is preferably a shared fluid port, fluidically coupled to all fluidic pathways 165 coupled to the sample port-reagent port pairs 112, and configured to deliver the same wash fluid, release fluid, and/or gas through the shared fluid port. Alternatively, as shown in FIG. 2, the top layer may comprise more than one fluid port 118, configured to deliver different wash fluids, release fluids, and/or gases to individual or multiple fluidic pathways 165 coupled to the set of sample port-reagent port pairs 112.

Preferably, the fluid port 118 is located along an edge of the microfluidic cartridge 100, which functions to increase accessibility to the fluid port by a system delivering fluids to the fluid port 118. In a specific embodiment, as shown in FIG. 1A, the fluid port is located approximately midway along an edge of the microfluidic cartridge 100, different from the edge along which the set of sample port-reagent port pairs 112 is located. Alternatively, the fluid port 118 may not be located along an edge of the microfluidic cartridge 100. Additionally, the fluid port 118 is preferably configured to be coupled to a syringe pump for fluid delivery; however, the fluid port 118 may alternatively configured to couple to any appropriate system for fluid delivery. Preferably, the wash fluid is a wash buffer for washing bound nucleic acid samples (i.e. nucleic acids bound to magnetic beads), the release fluid is a reagent for releasing bound nucleic acids samples from the magnetic beads, and the gas is pressurized air for moving fluids and demarcating separate reagents. Alternatively, the wash fluid, release fluid, and gas may be any appropriate liquids or gases used to carry out a molecular diagnostic procedure.

The heating region 195 of the top layer 110 functions to accommodate and position a heating element relative to elements of the microfluidic cartridge 100. The heating element preferably heats a defined volume of fluid and the magnetic beads, which has traveled through the microfluidic cartridge 100, according to a specific molecular diagnostic procedure protocol (e.g. PCR protocol), and is preferably an element external to the microfluidic cartridge 100; alternatively, the heating element may be integrated with the microfluidic cartridge and/or comprise a thermally conductive element integrated into the microfluidic cartridge 100. The heating region 195 is preferably a recessed fixed region of the top layer 110, downstream of the sample port-reagent port pairs 112, as shown in FIGS. 1A and 1B. Alternatively, the heating region may not be fixed and/or recessed, such that the heating region 195 sweeps across the top layer 110 of the microfluidic cartridge 100 as the heating element is moved. The microfluidic cartridge 100 may altogether omit the heating region 195 of the top layer 110, in alternative embodiments using alternative processes (e.g. chemical methods) for releasing nucleic acids from nucleic acid-bound magnetic beads.

The vent region 190 of an embodiment of the top layer 110 functions to remove unwanted gases trapped within a fluidic pathway 165 of the microfluidic cartridge, and may additionally function to position a defined volume of fluid within a fluidic pathway 165 of the microfluidic cartridge. The vent region 190 is preferably located downstream of the heating region 195 in an embodiment where the heating region 195 is fixed on the top layer 110 of the microfluidic cartridge 100, but alternatively may be located at another appropriate position on the top layer 110 such that unwanted gases are substantially removed from the microfluidic cartridge 100 during analysis. The top layer 110 may alternatively comprise more than one vent region 190 located at appropriate positions in the top layer 110. Preferably, as shown in FIGS. 1A and 1B, the vent region 190 is a recessed region in the top layer 110, and further comprises a film covering the vent region 190. Preferably, the film covering the vent region 190 is a gas-permeable but liquid-impermeable film, such that unwanted gases may be released from the microfluidic cartridge 100, but fluids remain within the microfluidic cartridge 100 and flow to the point of contacting the film. This functions to remove unwanted gases and position a defined volume of fluid within a fluidic pathway 165 of the microfluidic cartridge. In a specific embodiment, the film covering the vent region is a hydrophobic porous polytetrafluoroethylene-based material, synthesized to be gas-permeable but liquid-impermeable. Alternatively, the film covering the vent region may be gas and liquid permeable, such that unwanted gases and liquids are expelled from the microfluidic cartridge 100 through the vent region 190. Other alternative embodiments of the microfluidic cartridge 100 may altogether omit the vent region.

The set of detection chambers 116 of an embodiment of the top layer 110 functions to receive a processed nucleic acid sample, mixed with molecular diagnostic reagents, for molecular diagnostic analysis. Preferably, the set of detection chambers 116 is located along an edge of the top layer 110, opposite the edge along which the set of sample port-reagent port pairs 112 is located, which allows sample fluids dispensed into the microfluidic cartridge 100 to be processed and mixed with molecular diagnostic reagents on their way to a detection chamber 117 of the set of detection chambers 116 and facilitates access to the detection chambers by external elements performing portions of a molecular diagnostics protocol (e.g. heating and optics systems). Alternatively, the set of detection chambers 116 may not be located along an edge of the top layer 110. In a first variation, as shown in FIGS. 1A and 11B, each detection chamber 117 in the set of detection chambers comprises a serpentine-shaped channel 16 for facilitating analysis of a solution of nucleic acids mixed with reagents. In the first variation, three portions of the serpentine-shaped channel 16 are preferably wide and shallow to facilitate heating, and are interconnected by two narrow portions, which function to increase fluid flow resistance and reduce the proportion of nucleic acid not contained within the detection area. The first variation functions to facilitate filling of the set of detection chambers in a manner that reduces the potential for trapped air bubbles, to facilitate rapid molecular diagnostic techniques, and to comply with current imaging technologies. In a specific example of the first variation, each serpentine-shaped channel 16 is injected molded into the top layer 110 of the microfluidic cartridge 100, and the three interconnected portions of the serpentine-shaped channel 16 are each 1600 μm wide by 400 μm deep.

In a second variation, each detection chamber 117 in the set of detection chambers has a depth between 0.400 mm and 1.00 mm, and a diameter between 3.50 mm and 5.70 mm, to provide a volumetric configuration that facilitates reaction efficiency. In a specific example of the second variation, each detection chamber 117 in the set of detection chambers 116 is configured to contain a total volume of 10 uL, and has a depth of 0.80 mm and a diameter of 3.99 mm; however, in alternative embodiments, each detection chamber 117 in the set of detection chambers 116 may be configured to contain a total volume less than or greater than 10 uL.

Preferably, as shown in FIGS. 1A and 1B, the lower regions of each detection chamber 117 in the set of detection chambers 116 includes a PCR compatible film that is thin, to facilitate efficient thermocycling, and has low autofluorescence, to facilitate light-based molecular diagnostic assays performed at the set of detection chambers 116. The PCR compatible film is preferably composed of a polypropylene based polymer thermally bonded to the bottom of the top layer, but may alternatively be composed of any appropriate PCR-compatible material and bonded in any fashion. In one specific variation, the PCR compatible film is a cyclic olefin polymer (COP) film, thermally bonded to the top layer 110, with a glass transition temperature suitable for a molecular diagnostic protocol. In one alternative embodiment, depending on the configuration of imaging, heating, and/or cooling elements external to the microfluidic cartridge 100, the top and/or bottom of the detection chambers 117 in the set of detection chambers 116 may be entirely formed of a clear or transparent material (e.g. glass or plastic) allowing transmission of light. In a variation of this alternative embodiment, lensing, other optical components, or additional structures may also be incorporated into the detection chambers, to facilitate light transmission and/or focusing. In the variation of the alternative embodiment, a lens may be manufactured (e.g. injection molded) directly to form a surface of a detection chamber 117.

Figure 3:
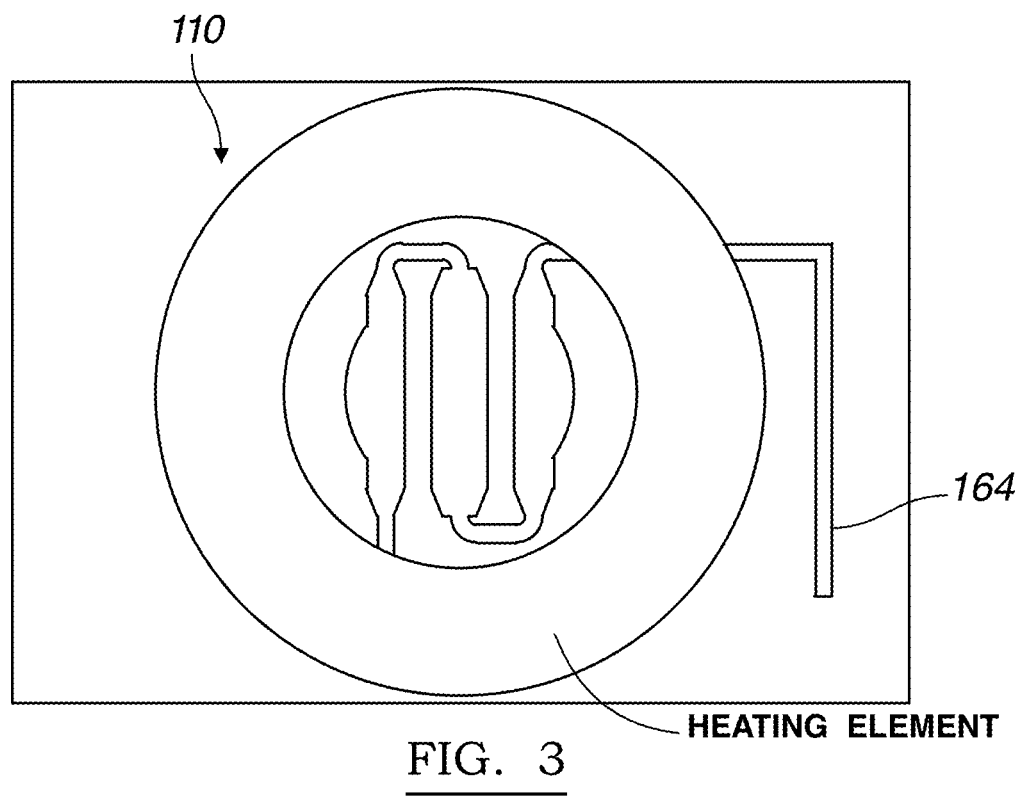
FIG. 3 depicts an alternative embodiment of a detection chamber of the microfluidic cartridge (top view) and a heating element configured to heat the detection chamber.

In the embodiment of the set of detection chambers 116 that includes a PCR compatible film, the PCR compatible film may further include a thermally conductive component, which functions to transfer heat from a heating element to the detection chamber. Depending on the position of the heating element(s) relative to the microfluidic cartridge 100 during analysis, the thermally conductive component of the PCR compatible film may be integrated with just the upper region of each detection chamber, just the lower region of each detection chamber, or both the upper and lower regions of each Detection chamber. The thermally conductive component of the PCR compatible film may comprise a wire mesh with a substantially small wire diameter, as shown in FIG. 3, thermally conductive particles distributed through the PCR compatible film (in a manner that still allows for optical clarity), or any other appropriate thermally conductive component (e.g. thermally conductive beads integrated into the PCR compatible film). The region laterally around the detection chamber may also further include one or more heat-transfer elements or air channels speed heat dissipation. Alternatively, a detection chamber 117 in the set of detection chambers 116 may not include a PCR compatible film with a thermally conductive component. Preferably, each detection chamber 117 is heated using a diced silicon wafer with conductive channels flip-chip bonded to a detection chamber to provide resistive heating; however, each detection chamber 117 may alternatively be heated using any appropriate heating device or method, and may be assembled using any appropriate method.

Preferably, each detection chamber 117 in the set of detection chambers 116 is thermally isolated from all other detection chambers, in order to prevent contamination of data from a detection chamber 117 due to heat transfer from other detection chambers in the set of detection chambers 116. In one embodiment, each detection chamber 117 of the set of detection chambers 116 is spaced far from adjacent detection chambers to limit thermal crosstalk. In another alternative embodiment, the top layer 110 may comprises slots between adjacent detection chambers to separate the detection chambers with an air gap. In one variation, thermal isolation is achieved by surrounding the side walls of each detection chamber 117 with a thermally insulating material, such as an insulating epoxy, putty, filler, or sealant. In another variation, the thermally insulating material has a low density, which functions to reduce heat transfer from other detection chambers. In yet another variation, thermal isolation is achieved by geometrically separating or displacing the detection chambers relative to each other within the top layer 110 of the microfluidic cartridge 100, such that heat transfer between detection chambers is hindered.

Preferably, each detection chamber 117 in the set of detection chambers 116 is also optically isolated from all other detection chambers, in order to prevent contamination of data from a detection chamber 117 due to light transfer from other detection chambers in the set of detection chambers 116. Preferably, optical isolation is achieved with detection chambers having substantially vertical walls, and separating each detection chamber 117 in the set of detection chambers from each other. However, in one variation, the sidewalls of each detection chamber 117 in the set of detection chambers 116 are either composed of or surrounded by a material with low autofluorescence and/or poor optical transmission properties to achieve optical isolation. In another variation, the sidewalls of each detection chamber 117 are surrounded by an optically opaque material, thus allowing transmission of light to a detection chamber 117 through only the top and bottom regions of the detection chamber 117. Alternatively, the microfluidic cartridge 100 may not further comprise any provisions for optical isolation of each detection chamber 117 in the set of detection chambers 116, aside from constructing the set of detection chambers 116 with a material having low autofluorescence.

Additionally, each detection chamber 117 in the set of detection chambers 116 may be further optimized to meet volumetric capacity requirements, facilitate high thermocycling rates, facilitate optical detection, and facilitate filling in a manner that limits bubble generation. Alternatively each detection chamber 117 in the set of detection chambers 116 may not be optimized to meet volumetric capacity requirements, facilitate high thermocycling rates, facilitate optical detection, and/or facilitate filling in a manner that limits bubble generation.

The top layer 110 of the microfluidic cartridge 100 may further comprise a set of cartridge-aligning indentations 180, which function to align the microfluidic cartridge 100 as it moves through an external module. As shown in FIG. 2 the set of cartridge-aligning indentations 180 are preferably located such that they do not interfere with any ports 112, 118, the heating region, 195, the vent region 190, and/or the set of detection chambers 116. In an embodiment, the top layer 110 of the microfluidic cartridge preferably comprises at least four cartridge-aligning indentations, located at points on the periphery of the top layer 110, and the cartridge-aligning indentations are configured to be recessed regions configured to mate with alignment pins in a system external to the microfluidic cartridge 100. Alternatively, the cartridge-aligning indentations may be grooves, such that the microfluidic cartridge 100 accurately slides into position along the grooves within a system external to the microfluidic cartridge 100. In yet another alternative embodiment, the set of cartridge-aligning indentations 180 may be any appropriate indentations that allow for positioning of the microfluidic cartridge 100 within an external system. However, the microfluidic cartridge 100 may altogether omit the set of cartridge-aligning indentations 180, and rely upon other features of the microfluidic cartridge 100 to facilitate alignment.

1.2 Microfluidic Cartridge—Intermediate Substrate

As shown in FIG. 1B, an embodiment of the microfluidic cartridge also comprises an intermediate substrate 120, coupled to the top layer 110 and partially separated from the top layer 110 by a film layer 125, configured to form a waste chamber 130. The intermediate substrate 120 functions to serve as a substrate to which layers of the microfluidic cartridge may be bonded, to provide guides for the valve pins, and to provide a waste chamber volume into which a waste fluid may be deposited. Preferably, the depth of the intermediate substrate 120 provides a waste chamber volume adequate to accommodate the volume of waste fluids generated within the microfluidic cartridge 100. Additionally, the depth of the intermediate substrate 120 provides a low profile for the microfluidic cartridge 100 to facilitate movement throughout a compact molecular diagnostic system. Preferably, the intermediate substrate 120 of the microfluidic cartridge 100 is also configured such that the footprint of microfluidic cartridge 100 adheres to microtiter plate standards, to facilitate automated handling of the microfluidic cartridge 100. The intermediate substrate 120 is preferably composed of a low-cost, structurally stiff material, such as polypropylene. However, similar to the top layer 120, the intermediate substrate may be alternatively composed of a structurally stiff material with low autofluorescence, such that the intermediate substrate 120 does not interfere with sample detection by fluorescence techniques, and an appropriate glass transition temperature for PCR techniques. In one variation of this alternative embodiment, the intermediate substrate 120 is composed of a cyclic olefin polymer (COP), produced by injection molding, with a glass transition temperature between 136 and 163° C. In yet another alternative embodiment, the intermediate substrate 120 may be composed of any appropriate material, for example, a polycarbonate based polymer.

Preferably, the intermediate substrate 120 of the microfluidic cartridge 100 is coupled to the top layer 110 and partially separated from the top layer 110 by a film layer 125. The film layer 125 functions to isolate individual fluidic pathways 165 of the microfluidic cartridge, to prevent leakage, to provide an appropriate environment for sample processing and conducting a molecular diagnostic protocol, and to provide access between a microfluidic channel (of a fluidic pathway 165) above the film layer 125 and elements below the film layer 125 (e.g. waste chamber and/or fluidic pathway occluder). Preferably, the film layer is a polypropylene (PP) with an appropriate glass transition temperature, such that it is PCR compatible and thermally bondable to the top layer 110; however, the film layer may alternatively be any appropriate material. In a specific embodiment, the film layer 125 is a polypropylene film between 30 and 100 microns thick and die cut to produce openings at a set of occlusion positions, to provide access between a microfluidic channel of a fluidic pathway 165 above the film layer 125 and elements below the film layer 125. In this specific embodiment, the openings are slightly oversized prior to assembly, in order to allow for constriction during assembly (due to thermal and pressure effects) and to provide higher tolerance during assembly of microfluidic cartridge layers. Alternatively, the film layer is any appropriate material such that it substantially isolates individual fluidic pathways, and is easily processable to provide access between a microfluidic channel of a fluidic pathway 165 above the film layer and elements below the film layer 125.

Preferably, the top layer 110, the film layer 125, and the intermediate substrate are bonded together, such that the top layer 110, film layer, 125, and intermediate substrate form a bonded unit with a hermetic seal to prevent fluid leakage. A hermetic seal is preferably formed using a silicone rubber layer coupled to the film layer 125, but may alternatively be formed using an alternative material or method. In a specific embodiment, a hermetic seal formed using a silicone rubber layer is only required at locations of openings within the film layer (e.g., at locations where an external occluder interacts with the microfluidic cartridge). Preferably, in an embodiment where the top layer 110, the film layer 125, and the intermediate substrate 120 are substantially identical materials (e.g. polypropylene), at least one of thermal bonding, adhesives, and ultrasonic welding are used to coupled the layers 110, 125, 120 together. In an embodiment where the top layer 110, the film layer 125, and the intermediate substrate 120 are substantially different materials—a combination of thermal bonding methods and adhesives may be used to bond the top layer 110, the film layer 125, and the intermediate substrate 120 of the microfluidic cartridge 100 together. In an alternative embodiment, the top layer 110, the film layer 125, and the intermediate substrate 120 of the microfluidic cartridge 100 may be thermally bonded together in a single step. In yet another alternative embodiment, the top layer 110, the film layer 125, and the intermediate substrate 120 may alternatively be modular, in applications where a portion of the microfluidic cartridge 100 is partially reusable (e.g. in an application where the waste chamber may be discarded after use, but the top layer and film may be reused). In yet another alternative embodiment, the top layer 110, the film layer 125, and the intermediate substrate 120 may only be partially bonded, such that a molecular diagnostic system, into which the microfluidic cartridge 100 is loaded, is configured to compress the top layer 110, the film layer 125, and the intermediate substrate 120 together, preventing any fluid leakage.

As shown in FIG. 1B, the intermediate substrate 120 of an embodiment of the microfluidic cartridge 100 is configured to form a waste chamber 130, which functions to receive and isolate waste fluids generated within the microfluidic cartridge 100. The waste chamber 130 is preferably continuous and accessible by each fluidic pathway 165 of the microfluidic cartridge 100, such that all waste fluids generated within the microfluidic cartridge 100 are deposited into a common waste chamber; however, each fluidic pathway 165 of the microfluidic cartridge 100 may alternatively have its own corresponding waste chamber 130, such that waste fluids generated within a fluidic pathway 165 of the microfluidic cartridge 100 are isolated from waste fluids generated within other fluidic pathways 165 of the microfluidic cartridge 100. In a specific embodiment of the microfluidic cartridge 100 with a continuous waste chamber, the waste chamber has a volumetric capacity of approximately 25 mL; however, the waste chamber 130 of another embodiment may have a different volumetric capacity. The intermediate substrate 120 further comprises a waste vent 135, which provides access between a microfluidic channel of a fluidic pathway 165 above the film layer 125 and the waste chamber 130. Preferably, the intermediate substrate 130 comprises more than one waste inlet 136, such that the waste chamber is accessible at more than one location along a fluidic pathway 165 through the waste inlets 136. Alternatively, the intermediate substrate 120 may include a single waste inlet 136, such that all waste fluids generated within the microfluidic cartridge 100 are configured to travel through the single waste inlet 136 into the waste chamber 130. Also, as shown in FIG. 1B, the intermediate substrate 120 may comprise a waste vent 131, such that the waste chamber 130 is vented to prevent pressure build up in the waste chamber as waste fluid is added.

Figure 4:
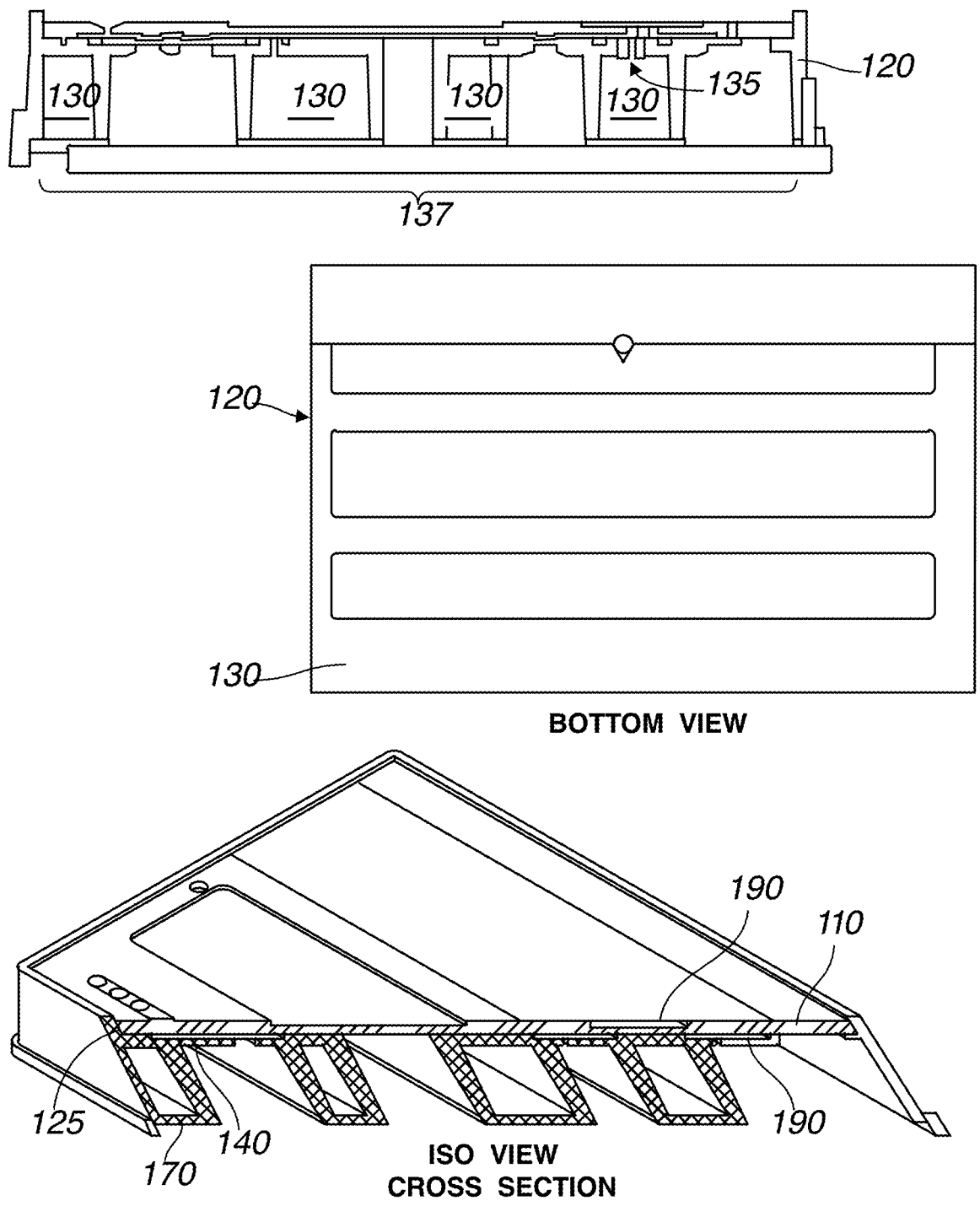
FIG. 4 depicts an embodiment of a waste chamber of the microfluidic cartridge.

As shown in FIGS. 1B and 4, the waste chamber 130 formed by the intermediate substrate 120 preferably has a corrugated surface 137, such that the waste chamber 130 is not only configured to receive and isolate a waste fluid, but also functions to 1) provide structural stability for the microfluidic cartridge 100 and 2) allow elements external to the microfluidic cartridge 100 to enter spaces formed by the corrugated surface 137, for greater accessibility to elements of the microfluidic cartridge 100. Also shown in FIGS. 1B and 4, each of the ridges in the corrugated surface 137 may not have the same dimensions, as a result of the locations of elements within and external to the microfluidic cartridge 100. In an embodiment of the waste chamber 130 with a corrugated surface 137, at least two ridges of the corrugated surface 137 are preferably the same height, such that the microfluidic cartridge 100 sits substantially level on a flat base. In an alternative embodiment, all ridges of the corrugated surface 137 of the waste chamber 130 are identical, for structural symmetry, and in yet another embodiment, the waste chamber 130 may not have a corrugated surface 137.

In one preferred embodiment, the intermediate substrate 120 of the microfluidic cartridge 100 further comprises a set of valve guides, which function to direct a series of external pins or other indenters through the valve guides at a set of occlusion positions 141, thus affecting flow through a microfluidic channel of a fluidic pathway 165 at the set of occlusion positions 141. The set of valve guides 127 may also function to facilitate alignment of the microfluidic cartridge 100 within an external molecular diagnostic module. In a first embodiment, as shown in FIG. 1B, the set of valve guides 127 comprises holes within the intermediate substrate 120 at the set of occlusion positions 141, with sloped edges configured to direct a pin or indenter through the holes. In the first embodiment, the set of valve guides 127 may be produced in the intermediate substrate 120 by injection molding, or may alternatively be produced by drilling, countersinking, chamfering, and/or beveling. In another embodiment, the set of valve guides 127 comprises grooves with holes, such that a pin or indenter is configured to travel along a groove and through a hole that defines the valve guide. In a simplified alternative variation, the set of valve guides 127 may comprise holes through the intermediate substrate 120, wherein the holes do not have sloped edges. In yet another simplified alternative variation, the set of valve guides 127 may comprise a slot configured to provide access to the elastomeric layer 140 by a group of occluding objects (e.g. pins or indenters), rather than a single occluding object.

1.3 Microfluidic Cartridge—Elastomeric and Bottom Layers

As shown in FIGS. 1B and 5A-5D, an embodiment of the microfluidic cartridge 100 also comprises an elastomeric layer 140 partially situated on the intermediate substrate 120, which functions to provide a deformable substrate that, upon deformation, occludes a microfluidic channel of a fluidic pathway 165 contacting the elastomeric layer 140 at an occlusion position of a set of occlusion positions 141. Preferably, the elastomeric layer 140 comprises an inert, liquid impermeable material, of an appropriate thickness, that can be heated to temperatures encountered during manufacturing and/or specified in a molecular diagnostic protocol, without substantial damage (i.e. compromised surface and/or loss of mechanical robustness) and is chemically compatible with a PCR assay. Preferably, the elastomeric layer 140 is non-continuous, such that portions of the elastomeric layer 140 are positioned relative to the intermediate substrate 120 in a manner that directly covers holes provided by the set of valve guides 127. Alternatively, the elastomeric layer 140 is a continuous layer, spanning a majority of the footprint of the microfluidic cartridge 100 while covering holes provided by the set of valve guides 127. In a specific embodiment, the elastomeric layer 140 comprises 500 micron thick strips of a low-durometer silicone that can be heated to at least 120° C. without substantial damage, which are bonded to a portion of the intermediate substrate 120 using a silicone-based adhesive and slightly compressed between the film layer 125 and the intermediate substrate 120. In a variation of the specific embodiment, the elastomeric layer 140 may alternatively be held in place solely by pressure between the intermediate layer 120 and the top layer 110. Preferably, the elastomeric layer 140 is reversibly deformable over the usage lifetime of the microfluidic cartridge 100, such that any occlusion of a microfluidic channel of a fluidic pathway 165 contacting the elastomeric layer 140 is reversible over the usage lifetime of the microfluidic cartridge. Alternatively, the elastomeric layer 140 may not be reversibly deformable, such that an occlusion of a microfluidic channel of a fluidic pathway 165 contacting the elastomeric layer 140 is not reversible.

Figure 5A:
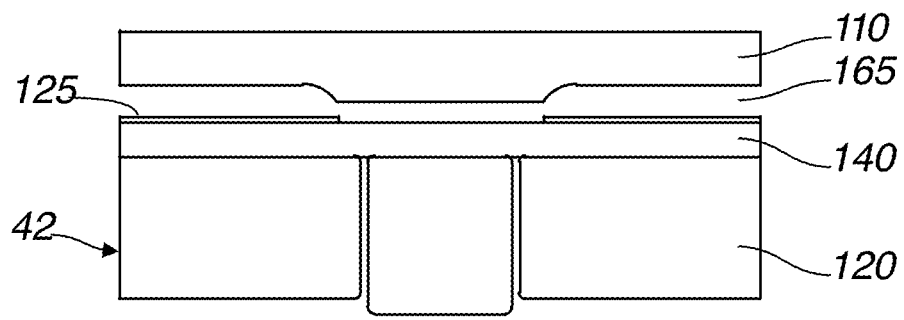
FIGS. 5A-5D depict embodiments of the elastomeric layer of the microfluidic cartridge, in open and occluded configurations.
Figure 5B:
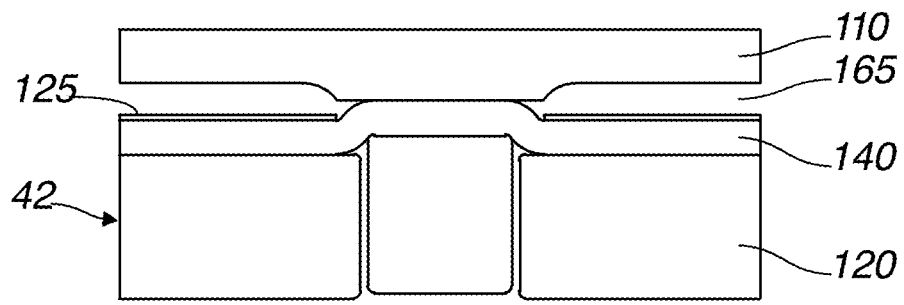
Figure 5C:
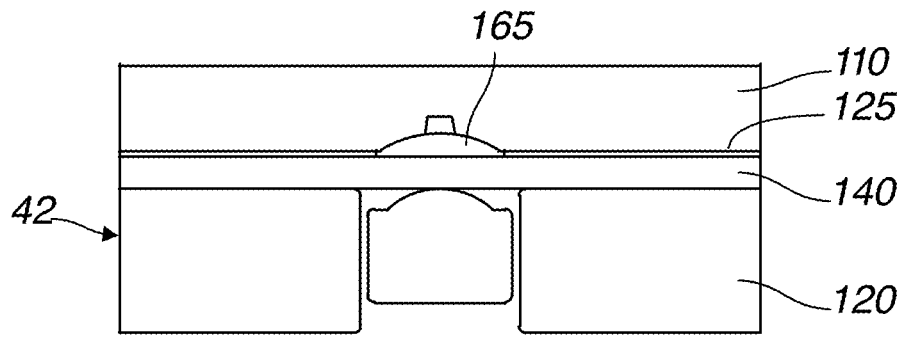
Figure 5D:
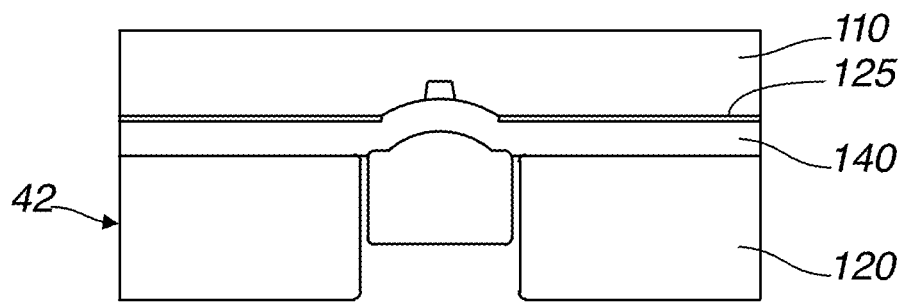

The set of occlusion positions 141 preferably comprises at least two types of occlusion positions, as shown in FIG. 1C, including a normally open position 42 and a normally closed position 43. As shown in FIGS. 5A-5D, the elastomeric layer 140 at a normally open position 42 of the set of occlusion positions 141 may be closed upon occlusion by an occluding object (FIGS. 5B and 5D). Preferably, a normally open position 42 is configured to withstand pressures that can be generated by a fluid delivery system (e.g. a syringe pump) without leaking, upon occlusion by an occluding object at the normally open position 42. In one specific example, a ½ barrel-shaped pin head may be used to fully occlude a normally open position 42 having an arched cross section, as in FIG. 5C, with near constant pressure on the portion of the elastomeric layer compressed between the occluding object and occluding position.

The normally closed position 43 of the set of occlusion positions 141, functions to be normally closed, but to be forced open in response to fluid delivery by a fluid delivery system. In one variation, the normally closed position 43 may be formed by manufacturing (e.g. injection molding) the top layer 100, such that the top layer material at a normally closed position 43 extends down to the elastomeric layer 140. If an occluding object is held away from the normally closed position 43, the occlusion position is closed, but can be forced open due to fluid pressure applied by a fluid delivery system (e.g. syringe pump). When not in operation, however, the normally closed position 43 is configured to prevent leakage and/or fluid bypass. The normally closed position may also be held closed by an occluding object, to prevent leakage even under pressure provided by a fluid delivery system, or under pressure experienced during a high temperature step (e.g., thermocycling) to prevent evaporation of a sample undergoing thermocycling.

The microfluidic cartridge 100 may further comprise a bottom layer 170 configured to couple to the intermediate substrate, which functions to allow waste to be contained within the microfluidic cartridge 100, and allow microfluidic cartridges to be stacked. The bottom layer thus facilitates reception, isolation, and containment of a waste fluid within the waste chamber. Preferably, the bottom layer 170 is composed of the same material as the intermediate substrate 120 for cost and manufacturing considerations, and bonded to the intermediate substrate 120 in a manner that provides a hermetic seal, such that a liquid within the waste chamber 130 does not leak out of the waste chamber 130. In a specific embodiment, the bottom layer 170 and the intermediate substrate 120 are both composed of a polypropylene-based material, and bonded together using an adhesive. In an embodiment of the microfluidic cartridge 100 where the waste chamber 130 has a corrugated surface, the bottom layer 170 preferably only seals voids defining the waste chamber 130, such that non-waste chamber regions (i.e. non-waste housing regions) are not covered by the bottom layer 170. Alternatively, the microfluidic cartridge 100 may omit the bottom layer 170, such that any waste fluid that enters the waste chamber 130 completely leaves the microfluidic cartridge 100 and is collected off-cartridge by a waste-collecting subsystem of an external molecular diagnostic system. In this alternative embodiment, the intermediate substrate 120 is configured to fluidically couple to the waste-collecting subsystem.

1.4 Microfluidic Cartridge—Magnet Housing

The magnet housing region 150 of the microfluidic cartridge 100 functions to provide access to and/or house at least one magnet 152 providing a magnetic field 156 for purification and isolation of nucleic acids. Preferably, the magnet housing region 150 is defined by the film layer and the intermediate substrate, such that the film layer and the intermediate substrate form the boundaries of the magnet housing region 150. In an embodiment of the microfluidic cartridge 100 comprising a bottom layer 170, the magnet housing region 150 may further be defined by the bottom layer 170, such that the bottom layer partially forms a boundary of the magnet housing region 150. The magnet housing region 150 is preferably a rectangular prism-shaped void in the microfluidic cartridge 150, and accessible only through one side of the microfluidic cartridge 100, as shown in FIG. 1B. Preferably, the magnet housing region 150 can be reversibly passed over a magnet 152 to house the magnet 152, and retracted to remove the magnet 152 from the magnet housing region 150; however, the magnet 152 may alternatively be irreversibly fixed within the magnet housing region 150 once the magnet 152 enters the magnet housing region 150.

Preferably, the magnet housing region 150 is bounded on at least two sides by the waste chamber 130, and positioned near the middle of the microfluidic cartridge 100, such that a fluidic pathway 165 passing through the magnetic field 156 passes through the magnetic field 156 at least at one point along an intermediate portion of the fluidic pathway 165. Preferably, the magnet housing region 150 also substantially spans at least one dimension of the microfluidic cartridge, such that multiple fluidic pathways 165 of the microfluidic cartridge 100 cross the same magnet housing region 150, magnet 152, and/or magnetic field 156. Alternatively, the magnet housing region 150 may be configured such that a magnet within the magnet housing region 150 provides a magnetic field spanning all fluidic pathways 165 of the microfluidic cartridge in their entirety. In alternative embodiments, the microfluidic cartridge may comprise more than one magnet housing region 150, a magnet housing region 150 may be configured to receive and/or house more than one magnet 152, and/or may not be positioned near the middle of the microfluidic cartridge 100. In yet another alternative embodiment, the magnet housing region 150 may permanently house a magnet 152, such that microfluidic cartridge comprises a magnet 152, integrated with the intermediate substrate 120. In embodiments where the magnet 152 is retractable from the microfluidic cartridge 100, the magnet 152 may be a permanent magnet or an electromagnet. In embodiments where the magnet 152 is configured to be integrated with the microfluidic cartridge 100, the magnet 152 is preferably a permanent magnet, which provides a stronger magnetic field per unit volume.

1.5 Microfluidic Cartridge—Fluidic Pathways

The set of fluidic pathways 160 of the microfluidic cartridge 100 functions to provide a fluid network into which volumes of sample fluids, reagents, buffers and/or gases used in a molecular diagnostics protocol may be delivered, out of which waste fluids may be eliminated, and by which processed nucleic acid samples may be delivered to a detection chamber for analysis, which may include amplification and/or detection. Preferably, each fluidic pathway 165 in the set of fluidic pathways 160 is formed by at least a portion of the top layer, a portion of the film layer, and a portion of the elastomeric layer 140, such that each fluidic pathway 165 may be occluded upon deformation of the elastomeric layer 140 at a set of occlusion positions 141. Additionally, at least one fluidic pathway 165 in the set of fluidic pathways 160 is preferably fluidically coupled to a sample port-reagent port pair 113 of the set of sample port-reagent port pairs 112, a fluid port 118, a waste chamber 130, and a detection chamber 117 of the set of detection chambers 116. Furthermore, at least one fluidic pathway 165 in the set of fluidic pathways 160 is preferably configured to be occluded upon deformation of the elastomeric layer 140, configured to transfer a waste fluid to the waste chamber 30, comprises a capture segment 166 passing through the heating region 195 and a magnetic field 156, and is configured to pass through the vent region 190 upstream of a detection chamber 117. Alternative embodiments may omit preferred elements of the embodiment of the fluidic pathway 165 described above, such as a vent region 190 or a heating region 195, or add additional elements to the embodiment of the fluidic pathway 165 described above.

A fluidic pathway 165 of the set of fluidic pathways 160 may comprise portions (i.e. microfluidic channels) that are located on both sides of the top layer 110, but is preferably located primarily on the bottom side of the top layer (in the orientation shown in FIG. 1B). In the orientation of the microfluidic cartridge 100 shown in FIG. 1B, a microfluidic channel on top of the top layer 110 may be further covered by second film layer 168 that seals the microfluidic channel on top of the top layer 110. The second film layer 168 may be comprise a cyclic olefin polymer (COP) film, thermally or adhesively bonded to the top layer 110, or alternatively may comprise another material that is bonded to the top layer 110. The use of film layers 125, 168 to cover microfluidic channels on either side of the top layer 110 facilitates manufacturing, such that long stretches of a fluidic pathway 165 do not need to be produced within the interior of the top layer 110. Preferably, microfluidic channels may be etched, formed, molded, cut, or otherwise shaped into the rigid structure of the top layer 110, and either remain on one side of the top layer 110, or pass through the thickness of the top layer 110.

In one variation, in the orientation of the microfluidic cartridge 100 shown in FIG. 11B, a fluidic pathway 165 is preferably located primarily on the bottom side of the top layer 110, comprising a segment running to a vent region 190 on the top side of the top layer 110. All other segments of the fluidic pathway 165 are preferably located on the bottom side of the top layer 110, allowing the fluidic pathway 165 to be sealed by the film layer 125 without requiring a separate film layer to seal channels located on the top of the top layer 110.

In another variation, in the orientation of the microfluidic cartridge 100 shown in FIG. 1B, a fluidic pathway 165 is preferably located primarily on the bottom side of the top layer 110, comprising a segment running to a detection chamber 163 on the top side of the top layer 110 and a segment running away from the detection chamber 164 on the top side of the top layer 110. In this variation, the fluidic pathway 165 thus crosses the thickness of the top layer 110 upstream of the first segment running to the detection chamber 163, and crosses the thickness of the top layer 110 downstream of the segment running away from the detection chamber 164, and crosses the thickness of the top layer 110 to couple to a sample port 114 and a reagent port 115 on the top side of the top layer 110. In another variation, as shown in FIG. 6C, a fluidic pathway 165 is preferably located primarily on the bottom side of the top layer 110, comprising only a segment running away from the detection chamber 164 on the top side of the top layer 110. In this other variation, the fluidic pathway 165 thus crosses the thickness of the top layer 110 downstream of the second portion, and crosses the thickness of the top layer 110 to couple to a sample port 114 and a reagent port 115 on the top side of the top layer 110. Alternatively, other embodiments may comprise a fluidic pathway 165 with a different configuration of portions on the top side of the top layer 110 and/or portions on the bottom side of the top layer 110.

As shown in FIGS. 1C, 6C, 7 and 9, a fluidic pathway 165 of the set of fluidic pathways 160 is branched and preferably comprises an initial segment 174 fluidically coupled to a fluid channel 119 coupled to a fluid port 118, a sample segment 175 coupled to a sample port 114, a reagent segment 176 coupled to a reagent port 115, a capture segment 166 passing through at least one of the heating region 195 and a magnetic field 156, a vent segment 177 configured to pass through the vent region 190, a segment running to a detection chamber 163, a segment running away from the detection chamber 164, and at least one waste segment 178, 179 configured to transfer a waste fluid to a waste chamber 130. Individual segments of the fluidic pathway 165 are preferably configured to pass through at least one occlusion position of the set of occlusion positions 141, to controllably direct fluid flow through portions of the fluidic pathway 165. A fluidic pathway 165 may also further comprise an end vent 199, which functions to prevent any fluid from escaping the microfluidic channel.

The initial segment 174 of the fluidic pathway 165 functions to deliver common liquids and/or gases from a fluid port 118 through at least a portion of the fluidic pathway 165, the sample segment 175 functions to deliver a volume of a sample fluid (e.g. sample comprising nucleic acids bound to magnetic beads) to a portion of the fluidic pathway 165, and the reagent segment 176 functions to deliver a volume of fluid comprising a reagent to a portion of the fluidic pathway 165. The capture segment 166 functions to facilitate isolation and purification of nucleic acids from the volume of the sample fluid, and may be s-shaped and/or progressively narrowing, to increase the efficiency and/or effectiveness of isolation and purification. Alternatively, the capture segment 166 may altogether be replaced by a substantially straight portion 166 or any other geometric shape or configuration that functions to facilitate isolation and purification of nucleic acids from the volume of the sample fluid. The capture segment 166 of the fluidic pathway 165 preferably has an aspect ratio less than one, which functions to facilitate capture of magnetic particles, but may alternatively have an aspect ratio that is not less than one.

The vent segment 177 functions to deliver a processed sample fluid through the vent region 190 for gas removal. The segment running to a detection chamber 163 functions to deliver a processed sample fluid to the detection chamber 117 with a reduced quantity of gas bubbles, and the segment running away from the detection chamber 164 functions to deliver a fluid away from the detection chamber 117. The segments may be arranged in at least one of several configurations to facilitate isolation, processing, and amplification of a nucleic acid sample, as described in three exemplary embodiments below:

A first embodiment, as shown in FIG. 1C, of a fluidic pathway 165 preferably comprises an initial segment 174 fluidically coupled to a fluid channel 119 coupled to a shared fluid port 118, a sample segment 175 coupled to a sample port 114 and to the initial segment 174, and an s-shaped capture segment 166, configured to pass through the heating region 195 and a magnetic field 156, coupled to the initial segment 174 and the sample segment 175. In a variation of the first embodiment, the s-shaped capture segment 166 may comprise an initial wide arc 166 to provide a greater surface area for magnetic bead capture. In another variation of the first embodiment, the capture segment 166 may alternatively be a progressively narrowing s-shaped capture segment 166. The first embodiment of the fluidic pathway 165 also comprises a reagent segment 176 coupled to a reagent port 115 and to the capture segment 166, a vent segment 177 coupled to the reagent segment 176 and configured to pass through the vent region 190, a segment running to a detection chamber 163 from the vent region 190, a winding segment running away from the detection chamber 164, and an end vent 199 coupled to the segment running away from the detection chamber 164. The first embodiment of the fluidic pathway 165 also comprises a first waste segment 178 configured to couple the initial segment 174 to the waste chamber 130, and a second waste segment 179 configured to couple the capture segment 166 to the waste chamber 1300. The first waste segment 178 preferably functions to allow evacuation of excess release fluids from a fluidic pathway 165, for precise metering of the amount of release reagents used in a molecular diagnostic procedure using a low volume of sample.

In the first embodiment, the set of occlusion positions 141 comprises a first occlusion position 142 located along the initial segment 174 between points at which the initial segment couples to the fluid channel 119 and to the capture segment 166. The set of occlusion positions 141 also comprises a second occlusion position 143 located along the sample segment 175, a third occlusion position 144 located along the reagent segment 176, a fourth occlusion position 145 located along the first waste segment 178, and a fifth occlusion position 146 located along the second waste segment 179. In the first embodiment, the set of occlusion positions 141 also comprises a sixth occlusion position 147 located along the vent segment 177 upstream of the vent region 190, a seventh occlusion position 148 located along the segment running to the detection chamber 163, and an eighth occlusion position 149 located along the segment running away from the detection chamber 164. In the first embodiment, the first, second, third, fifth, and sixth occlusion positions 142, 143, 144, 146, 147 are normally open positions 42 and the fourth, seventh, and eighth occlusions positions 145, 148, 149 are normally closed positions 43, as shown in FIG. 1C.

Figure 1D:
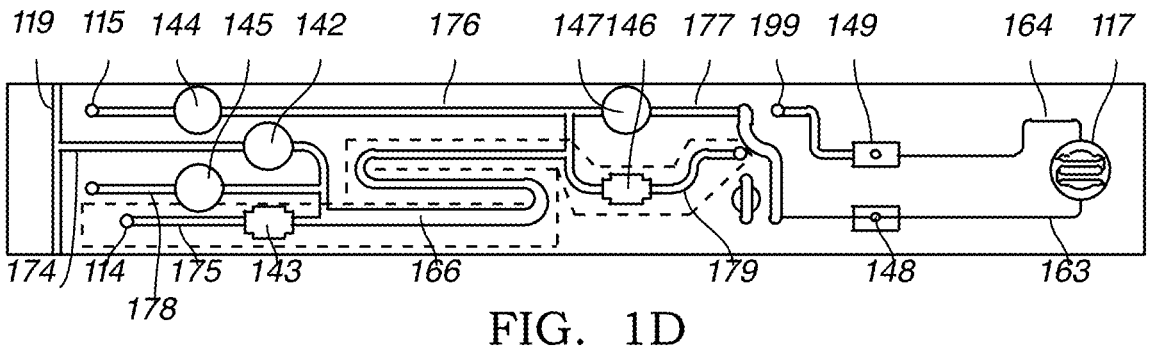
FIGS. 1D-K depict an example embodiment of subsets of occlusion positions defining truncated portions of a fluidic pathway.
Figure 1E:
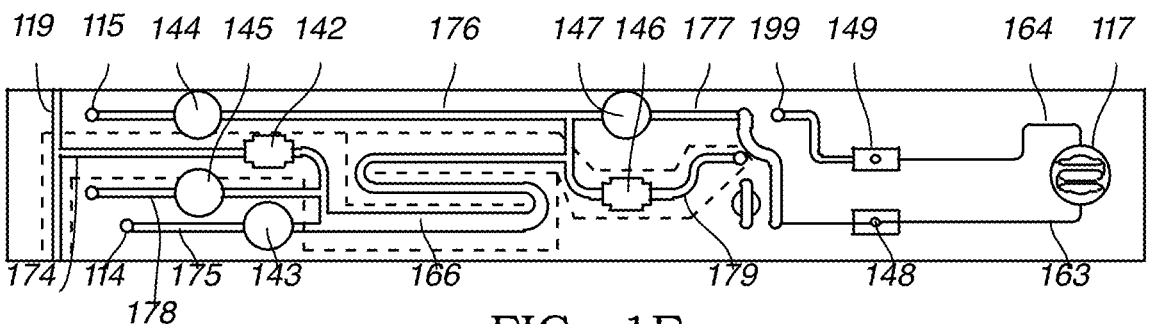

The occlusion positions of the set of occlusion positions 141 of the first embodiment are preferably located such that occluding subsets of the set of occlusion positions 141 defines unique truncated fluidic pathways to controllably direct fluid flow. For example, as shown in FIG. 1D, occluding the fluidic pathway 165 at the first, third, fourth, and sixth occlusion positions 142, 144, 145, 147 forms a truncated pathway by which a volume of a sample fluid, comprising nucleic acids bound to magnetic beads and delivered into the sample port 114, may flow past the second occlusion positions 143 into the capture segment 166 for isolation and purification of nucleic acids using the heating region 195 and the magnetic field 156. Nucleic acids bound to magnetic beads may thus be trapped within the capture segment 166 by the magnetic field 156, while other substances in the volume of sample fluid may pass into the waste chamber 130 by passing the fifth occlusion position 146. Following this subset of occlusion positions, the occlusion at the first occlusion position 142 may be reversed, as shown in FIG. 1E, and the fluidic pathway 165 may be occluded at the second occlusion position 143 to form a second truncated pathway by which a wash fluid may be delivered through the fluid port 118, into the capture segment 166 (thus washing the trapped magnetic beads), and into the waste chamber 130 by passing the fifth occlusion position 146. The occlusion at the second occlusion position 143 may then be reversed, and the first occlusion position 142 may be occluded (as shown in FIG. 1D), so that other fluidic pathways in the set of fluidic pathways 160 may be washed. After all fluidic pathways have been washed, a volume of air may be transferred through the fluid port 118 to prevent mixture of a wash solution with a release solution.

Figure 1F:
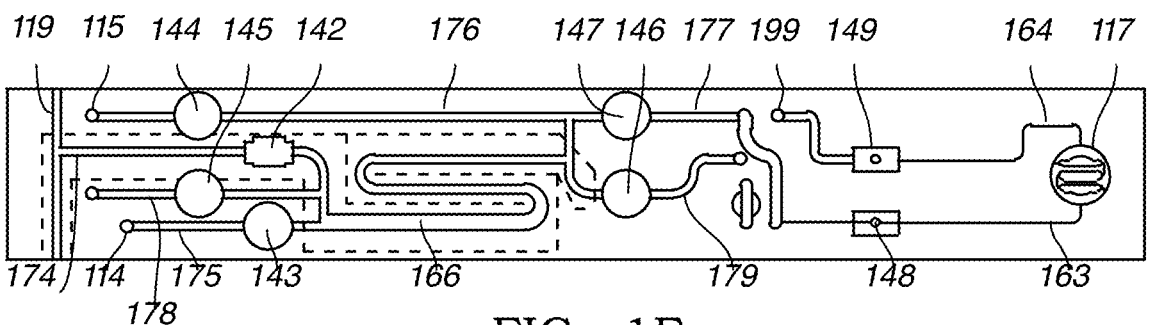

Thereafter in the first embodiment, as shown in FIG. 1E, the fluidic pathway 165 may be occluded at the second occlusion position 143 and the occlusion at the first occlusion 142 may be reversed, thus creating a third truncated pathway as shown in FIG. 1D. A release solution may then be delivered through the fluid port 118, into the capture segment 166, and to the waste chamber 130 by passing the fifth occlusion position 146. The release solution may then be sealed within a fourth truncated pathway (including the capture segment 166) of the fluidic pathway 165 by occluding the fluidic pathway at the fifth occlusion position 146, as shown in FIG. 1F. A release solution may then be delivered to other fluidic pathways of the set of fluidic pathways 160.

Figure 1G:
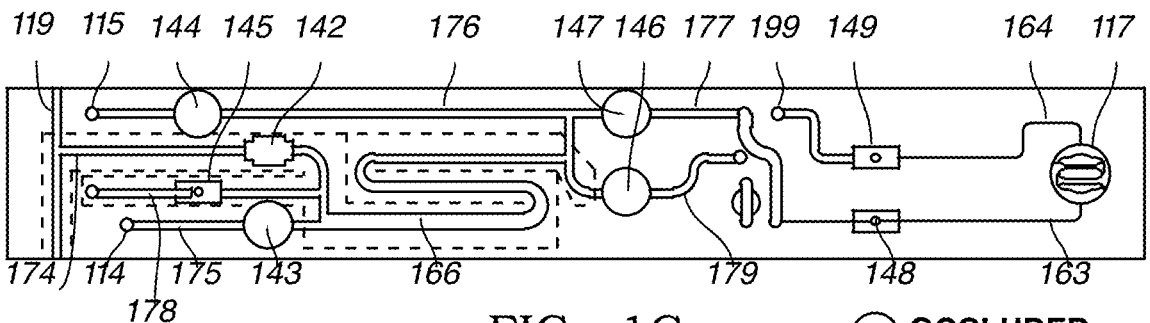
Figure 1H:
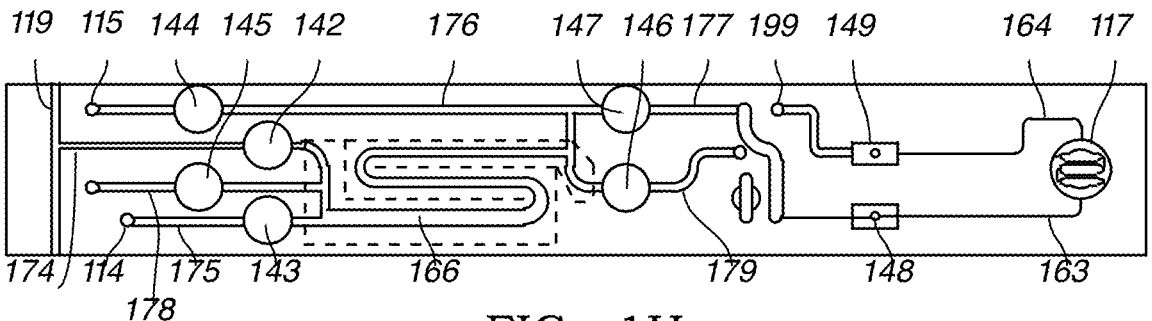

Thereafter, as shown in FIG. 1G, the occlusion at the fourth occlusion position 145 may be reversed, creating a fifth truncated pathway, and release solution within the fluidic pathway 165 may be metered by pumping air through the fluid port 118, which functions to push a portion of the release solution into the waste chamber 130. A volume of release solution will still be maintained within the capture segment 166 at this stage. As shown in FIG. 1H, the first and the fourth occlusion positions 142, 145 may then be occluded to form a sixth truncated pathway sealing the volume of release solution, with the captured magnetic beads bound to nucleic acids, within the capture segment 166. The volume of the remaining release solution is therefore substantially defined by the microchannel volume between junctions in the fluidic pathway 165 near the fourth and sixth occlusion positions 145, 147, and may be any small volume but in a specific variation is precisely metered to be 23+/−1 microliters. Release solution may be sealed within capture segments of other fluidic pathways using a similar process. A heater may then be provided at the sixth truncated pathway, inducing a pH shift within the sixth truncated pathway to unbind nucleic acids from the magnetic beads.

Figure 1I:
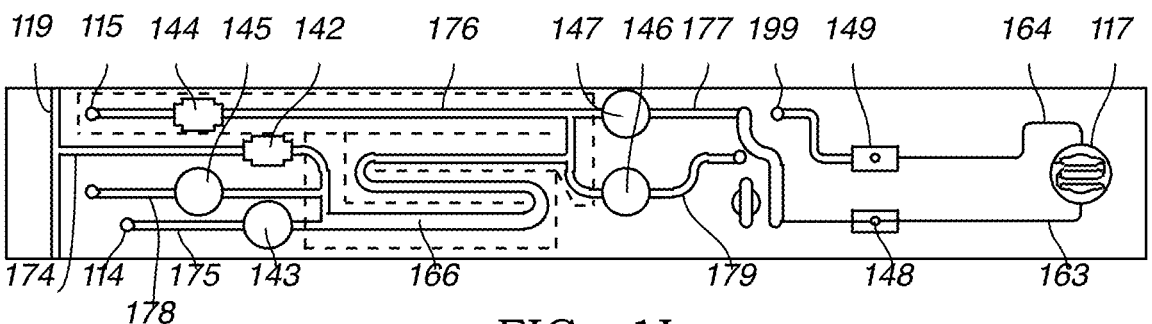
Figure 1J:
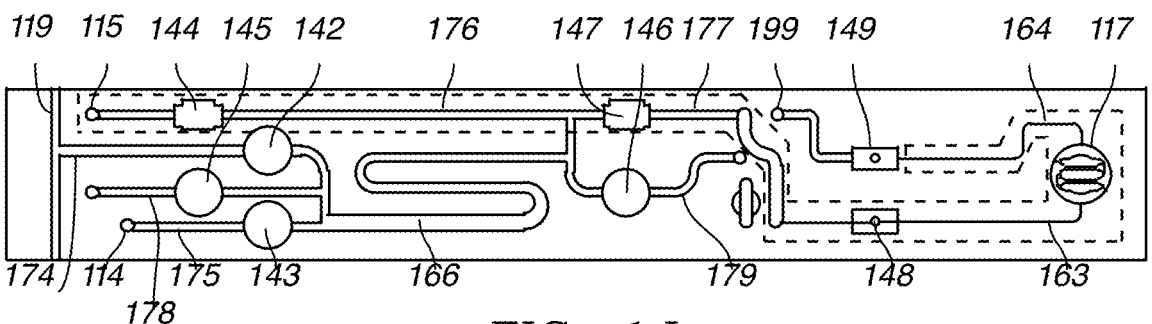
Figure 1K:
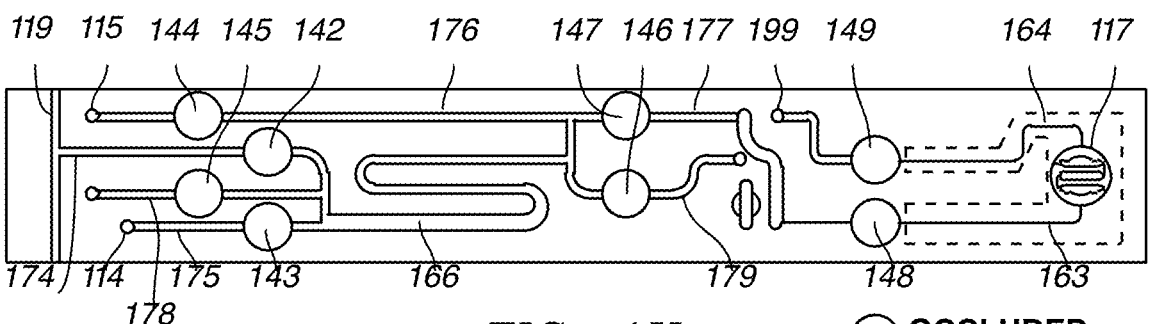

Thereafter in the first embodiment, as shown in FIG. 1i, the occlusions at the first and third occlusion positions 142, 144 may be reversed, defining a seventh truncated pathway, and the entire released nucleic acid sample (e.g. ~20 microliters) may be aspirated out of the microfluidic cartridge through the reagent port 115. This released nucleic acid sample is then used to reconstitute a molecular diagnostic reagent stored off of the microfluidic cartridge 100. During the reconstitution, the occlusion at the sixth occlusion position 147 may be reversed, and the fluidic pathway 165 may be occluded at the first occlusion position 142 to form an eighth truncated pathway, as shown in FIG. 1J. Once reconstitution of the molecular diagnostic reagent with the released nucleic acid sample is complete and well mixed, the reconstituted mixture may then be dispensed through the reagent port 115, through the eighth truncated pathway, and to the detection chamber 117, by using a fluid handling system to push the seventh occlusion position (normally closed) open. The detection chamber 117 is completely filled with the mixed reagent-nucleic acid sample, after which the fluidic pathway 165 is occluded at the third, sixth, seventh and eighth occlusion positions 144, 147, 148, 149, defining ninth truncated pathway, as shown in FIG. 1K. Other pathways of the set of fluidic pathways 165 may be similarly configured to receive a reagent-nucleic acid mixture. An external molecular diagnostic system and/or module may then perform additional processes, such as thermocycling and detection, on the volume of fluid within the detection chamber 117.

An alternative variation of the first embodiment may further comprise additional occlusion positions or alternative variations of the set of occlusion positions 141, such that occlusion at the additional occlusion positions permanently seals the waste chamber from the fluidic pathway 165. Other alternative variations of the first embodiment may also comprise configurations of the set of occlusion positions 141 that are different than that described above. The variations may be configured, such that the a fluidic pathway 165 facilitates meter release, does not allow meter release, facilitates addition of other reagents (e.g. neutralization or DNase reagents), facilitates additional washing steps, and/or facilitates other operations without changing the layout of the fluidic pathway 165 of a microfluidic cartridge embodiment. Thus, multiple unique operations may be performed using the same microfluidic cartridge, by occluding fluidic pathways 160 at varied subsets of a set of occlusion positions 141.

A second embodiment, as shown in FIG. 6C, of a fluidic pathway 165' preferably comprises an initial segment 174' fluidically coupled to a fluid channel 119' coupled to a shared fluid port 118', a sample segment 175' coupled to a sample port 114' and to the initial segment 174', and a capture segment 166', configured to pass through the heating region 195 and a magnetic field 156, coupled to the initial segment 174'. The second embodiment of the fluidic pathway 165' also comprises a reagent segment 176' coupled to a reagent port 115' and to the turnabout portion 176', a vent segment 177' coupled to the reagent segment 176' and to the capture segment 166' and configured to pass through the vent region 190, a segment running to a detection chamber 163' from the vent region 190, a segment running away from the detection chamber 164', and an end vent 199 coupled to the segment running away from the detection chamber 164'. The second embodiment of the fluidic pathway 165' also comprises a first waste segment 178', coupled to the initial segment 174' at a point between points connecting the initial segment 174' to the sample segment 175' and to the capture segment 166'. The first waste segment 178' is configured to couple the initial segment 174' to the waste chamber 130. The second embodiment of the fluidic pathway 165' also comprises a second waste segment 179' configured to couple the capture segment 166' to the waste chamber 130', and an end vent segment 197' coupled to the capture segment 166' downstream of the point of connection to the second waste segment 179', and coupled to an end vent 199. The end vent segment 197' functions to provide fine metering of a fluid flowing through the fluidic pathway 165'.

In the second embodiment, the set of occlusion positions 141' comprises a first occlusion position 142' located along the initial segment 174' between points at which the initial segment couples to the fluid channel 119' and to the sample segment 175'. The set of occlusion positions 141' also comprises a second occlusion position 143' located along the sample segment 175', a third occlusion position 144' located along the reagent segment 176', a fourth occlusion position 145' located along the first waste segment 178', and a fifth occlusion position 146' located along the second waste segment 179'. In the second embodiment, the set of occlusion positions 141' also comprises a sixth occlusion position 147' located along the vent segment 177' upstream of the vent region 190, a seventh occlusion position 148' located along the segment running to the detection chamber 163', and an eighth occlusion position 149' located along the segment running away from the detection chamber 164'. Additionally, in the second embodiment, the set of occlusion positions 141 comprises a ninth occlusion position 157' located along the sample segment 175' between the sample port 114 and the second occlusion position 143, a tenth occlusion position 158' located along the end vent segment 197', and an eleventh occlusion position 159' located along the capture segment 166' between points at which the capture segment 166' couples to the end vent segment 197' and to the vent segment 177'.

The occlusion positions of the set of occlusion positions 141' of the second embodiment are preferably located such that occluding of subsets of the set of occlusion positions 141' defines unique truncated fluidic pathways to controllably direct fluid flow. For example, occluding the fluidic pathway 165' at the first, fourth, sixth, tenth, and eleventh occlusion positions 142', 145', 147', 158', 159' forms a truncated pathway by which a volume of a sample fluid, comprising nucleic acids bound to magnetic beads and delivered into the sample port 114, may flow into the capture segment 166' for isolation and purification of nucleic acids using the heating region 195 and the magnetic field 156. Nucleic acids bound to magnetic beads may thus be trapped within the capture segment 166' by the magnetic field 156, while other substances in the volume of sample fluid may pass into the waste chamber 130 by passing the fifth occlusion position 146'. Following this subset of occlusion positions, the occlusion at the first occlusion position 142' may be reversed, and the fluidic pathway 165' may be occluded at the second occlusion position 143' to form a second truncated pathway by which a wash fluid may be delivered through the fluid port 118, into the capture segment 166' (thus washing the trapped magnetic beads), and into the waste chamber 130 by passing the fifth occlusion position 146'. A volume of air may then be pumped through the fluid port 118 to flush any remaining wash solution into the waste chamber 130.

Thereafter, in the second embodiment, the fluidic pathway 165' may be occluded at the fifth occlusion position 146' and the occlusion at the tenth occlusion position 158' may be reversed, closing access to the waste chamber 130 and opening access to the end vent segment 197'. A release solution may then be delivered through the fluid port 118, into the capture segment 166', and to the end vent segment 197'. The volume of the release solution is therefore defined by the microchannel volume between the fourth and tenth occlusion positions 145', 158', and may be any small volume but in a specific variation is precisely metered to be 15 microliters. Thereafter, occluding the fluidic pathway 165' at the tenth occlusion position 158', reversing the occlusion at the fourth occlusion position 145' (defining a fourth truncated pathway), and delivering air through the fluid port 118 pushes any remaining release buffer from the fluidic pathway 118 into the waste chamber 130, thereby ensuring that excess release buffer is not later exposed to nucleic acids bound to the magnetic beads (at this point, the nucleic acids are not substantially released from the magnetic beads because heat has not been added). Thereafter, the fluidic pathway 165' is occluded at the first and fourth occlusion positions 142', 145', defining a fifth truncated pathway comprising the capture segment 166', and the magnetic beads are heated to an appropriate temperature and time (e.g., 60 degrees for 5 minutes) within the heating region 195 to release the nucleic acids from the magnetic beads and into the release buffer.

Thereafter, in the second embodiment, the occlusions at the first and eleventh occlusion positions 142', 159' are reversed, defining a sixth truncated pathway, the entire released nucleic acid sample (e.g. ~15 microliters) may be aspirated out of the microfluidic cartridge through the reagent port 115. This released nucleic acid sample is then used to reconstitute a molecular diagnostic reagent mixture stored off of the microfluidic cartridge 100. During the reconstitution process, the occlusion at the sixth occlusion position 147' may be reversed, thus defining a seventh truncated pathway. Once reconstitution of the molecular diagnostic reagent mixture with the released nucleic acid sample is complete and well mixed, the reconstituted mixture may then be aspirated through the reagent port 115 through the seventh truncated pathway to the detection chamber 117, completely filling the detection chamber 117, after which the fluidic pathway 165' is be occluded at third, seventh, eighth, and ninth occlusion positions 144', 148', 149', 157' defining an eighth truncated pathway. An external molecular diagnostic system and/or module may then perform additional processes on the volume of fluid within the detection chamber 117.

An alternative variation of the second embodiment may further comprise additional occlusion positions or alternative variations of the set of occlusion positions 141', such that occlusion at the additional occlusion positions permanently seals the waste chamber from the fluidic pathway 165'. Other alternative variations of the second embodiment may also comprise configurations of the set of occlusion positions 141' that are different than that described above.

Figure 7:
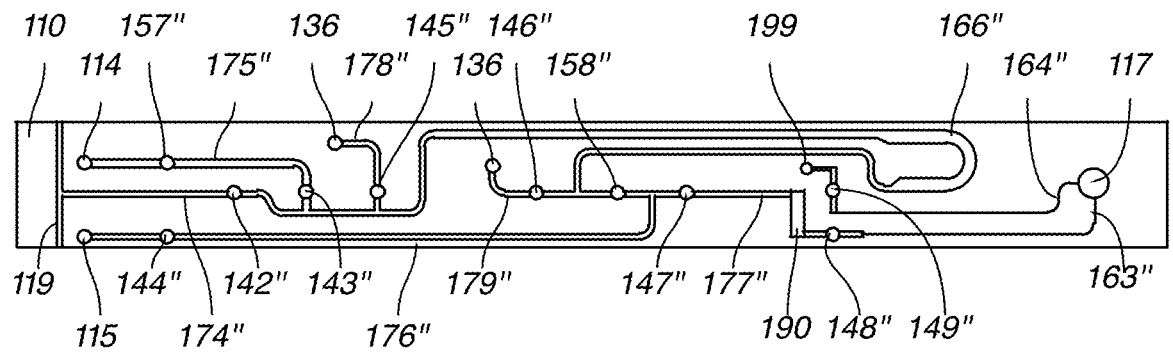
FIG. 7 depicts another alternative embodiment of a microfluidic pathway of the microfluidic cartridge.

A third embodiment, as shown in FIG. 7, of a fluidic pathway 165" preferably comprises an initial segment 174" fluidically coupled to a fluid channel 119" coupled to a shared fluid port 118, a sample segment 175" coupled to a sample port 114 and to the initial segment 174", and a capture segment 166" coupled to the initial segment 174". The third embodiment of the fluidic pathway 165" also comprises a reagent segment 176" coupled to a reagent port 115, a vent segment 177" coupled to the reagent segment 176" and to the capture segment 166", and configured to pass through the vent region 190, a segment running to a detection chamber 163" from the vent region 190, a segment running away from the detection chamber 164", and an end vent 199 coupled to the segment running away from the detection chamber 164". The third embodiment of the fluidic pathway 165" also comprises a first waste segment 178" configured to couple the initial segment 174" to the waste chamber 130, and a second waste segment 179" configured to couple the capture segment 166" to the waste chamber 130.

In the third embodiment, the set of occlusion positions 141" comprises a first occlusion position 142" located along the initial segment 174" between points at which the initial segment 174" couples to the fluid channel 119" and to the sample segment 175". The set of occlusion positions 141" also comprises a second occlusion position 143" located along the sample segment 175", a third occlusion position 144" located along the reagent segment 176", a fourth occlusion position 145" located along the first waste segment 178", and a fifth occlusion position 146" located along the second waste segment 179". In the third embodiment, the set of occlusion positions 141" also comprises a sixth occlusion position 147" located along the vent segment 177" upstream of the vent region 190, a seventh occlusion position 148" located along the segment running to the detection chamber 163", an eighth occlusion position 149" located along the segment running away from the detection chamber 164", and a ninth occlusion position 157'" located along the vent segment 177" between the point at which the vent segment 177" couples to the second waste segment 179" and the sixth occlusion point 147".

Similar to the first and the second embodiments, the occlusion positions of the set of occlusion positions 141" of the third embodiment are preferably located such that an occlusion of subsets of the set of occlusion positions 141" defines unique truncated fluidic pathways to controllably direct fluid flow. Example truncated fluidic pathways, defined by occluding the fluidic pathway 165" using subsets of the set of occlusion positions 141", are shown in FIG. 7.

Figure 8A:
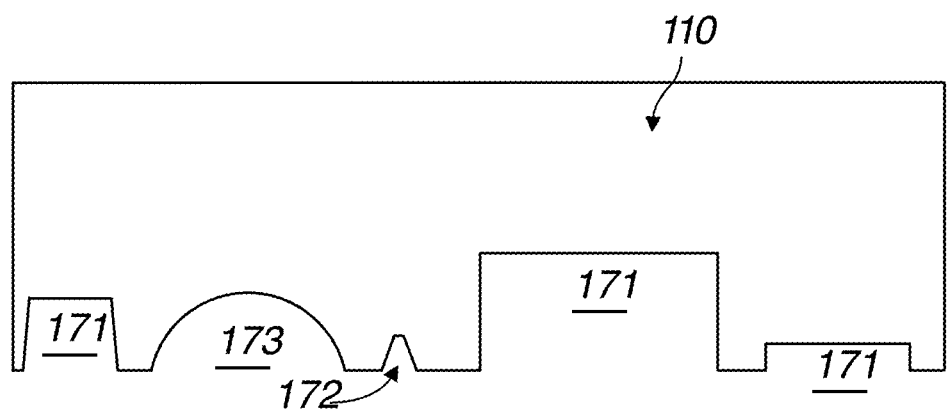
FIGS. 8A and 8B depict schematics of microfluidic channel cross sections.

Preferably, a fluidic pathway 165 of the set of fluidic pathways 160 comprises at least one of a first channel type 171, a second channel type 172 with a reduced cross sectional area, and a third channel type 173 with an curved surface as shown in FIG. 8A. A variation of the first channel type 171 has an approximately rectangular cross section with slightly sloping walls, such that at least two walls of the first channel type 171 slope toward each other to facilitate manufacturing of the first channel type 171; however, alternative variations of the first channel type 171 may have non-sloping walls or walls that slope away from each other. In specific embodiments of the first channel type 171, the walls of the first channel type 171 slope at 6° from vertical, to facilitate extraction of injection molded parts, and are between 300 and 1600 microns wide and between 100 and 475 microns tall. In a first specific embodiment of the second channel type 172, the cross section of the second channel type 172 is a 250 micron wide equilateral triangle with the top truncated to be 200 microns deep. In a second specific embodiment of the second channel type 172, the cross section of the second channel type is a truncated triangle that is 160 microns wide and 160 microns deep. In a specific embodiment of the third channel type 173, the surface of the third channel type is defined by Gaussian function, and is 800 microns wide and 320 microns deep. Alternative embodiments of the third channel type 173 may comprise a surface defined by any appropriate curved function.

Figure 8B:
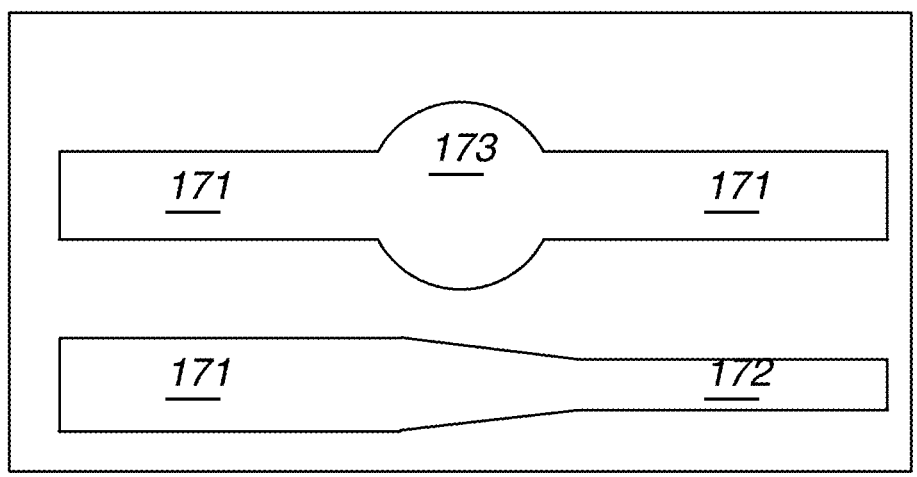
Figure 8C:
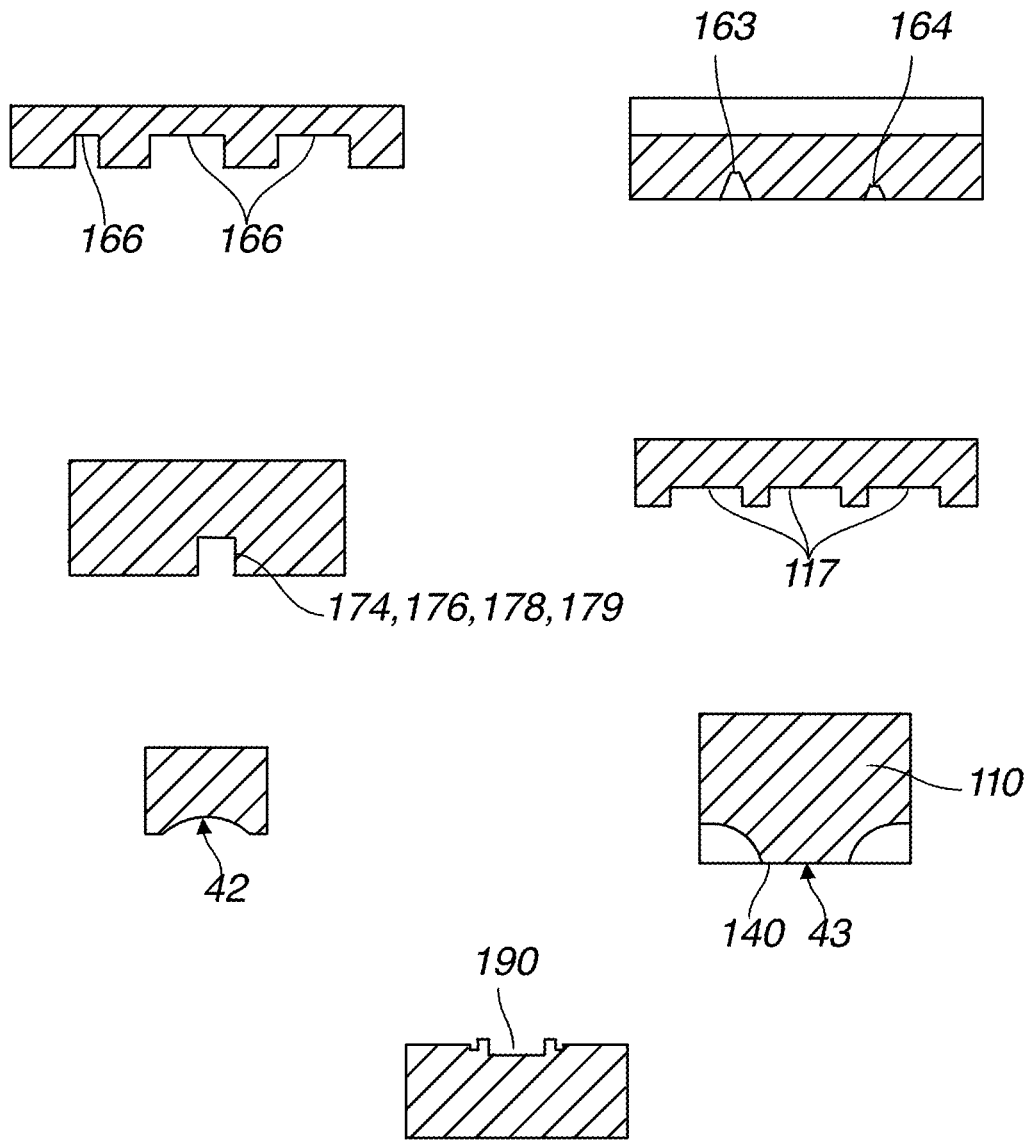
FIG. 8C depicts specific embodiments of microfluidic channel cross sections.

The first channel type 171 is preferably used over a majority of a fluidic pathway 165, and preferably in portions near a vent region 190, in a capture segment 166 configured to pass through a magnetic field 156, and in a segment leading to a Detection chamber 163. Preferably, an embodiment of the first channel type 171, comprising a wide channel with little depth is used in regions configured to pass through a magnetic field 156, such that particles in the regions are driven closer to the magnetic field source. The second channel type 172 is preferably used near a vent region 190 of a fluidic pathway 165, and preferably in portions of a fluidic pathway 165 leading to and away from a detection chamber 163, 164 (to constrict fluid flow into the Detection chamber 117). The third channel type 173 is preferably used in a portion of a fluidic pathway 165 near a normally open position 42 of the set of occlusion positions 141. Transitions between different channel types 171, 172, 173 may be abrupt, or alternatively, may be gradual, as shown in FIG. 8B. The first, second, and third channel types 171, 172, 173 may also alternatively be used in any appropriate portion of a fluidic pathway 165. Example embodiments of channel types for segments of a fluidic pathway are shown in FIG. 8C.

Multiple fluidic pathways may be configured to pass through a single heating region 195 of the microfluidic cartridge 100, a single vent region 190 of the microfluidic cartridge 100, and/or a magnetic field 156 produced by a magnet 152 housed within a single magnet housing region 150. Preferably all fluidic pathways of the set of fluidic pathways 160 are configured to pass through a single heating region 195 of the microfluidic cartridge 100, a single vent region 190 of the microfluidic cartridge 100, and a magnetic field 156 produced by a magnet 152 housed within a single magnet housing region 150; however, alternative embodiments of the set of fluidic pathways 160 of the microfluidic cartridge may comprise different configurations wherein fluidic pathways of the set of fluidic pathways 160 do not share a single heating region 195, a single vent region 190, and/or a magnetic field 156.

Figure 9:
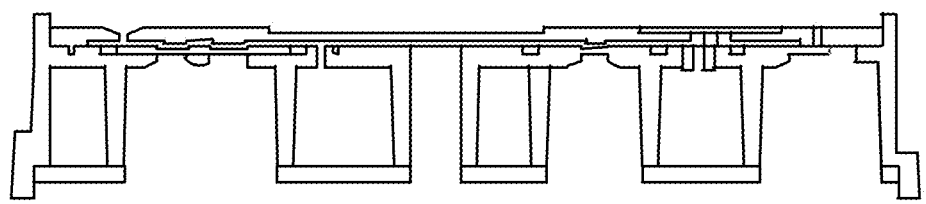
FIG. 9 depicts an embodiment of the microfluidic cartridge with twelve fluidic pathways (four of which are shown)
Figure 9:
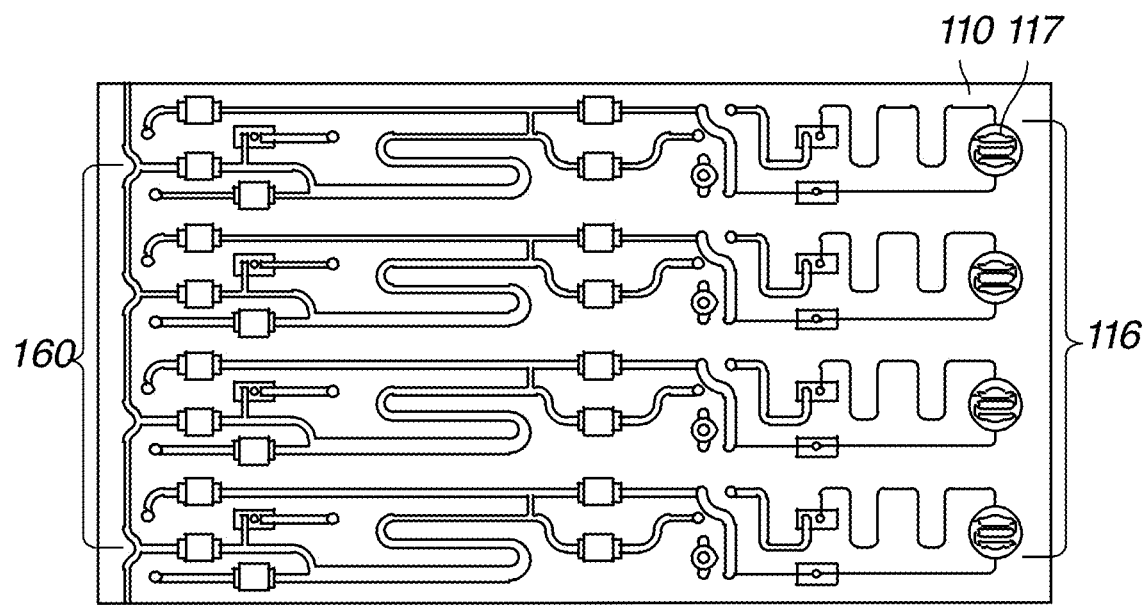

Additionally, the set of fluidic pathways 160 of the microfluidic cartridge 100 may comprise virtually any number of fluidic pathway 165 and/or the set of Detection chambers 116 may comprise virtually any number of Detection chambers 116 as can practically be integrated into the microfluidic cartridge 100. In one specific embodiment, the set of fluidic pathways 160 may comprise twelve fluidic pathways 165, four of which are shown in FIG. 9.

1.6 Microfluidic Cartridge—Additional Microfluidic Cartridge Elements

Figure 10A:
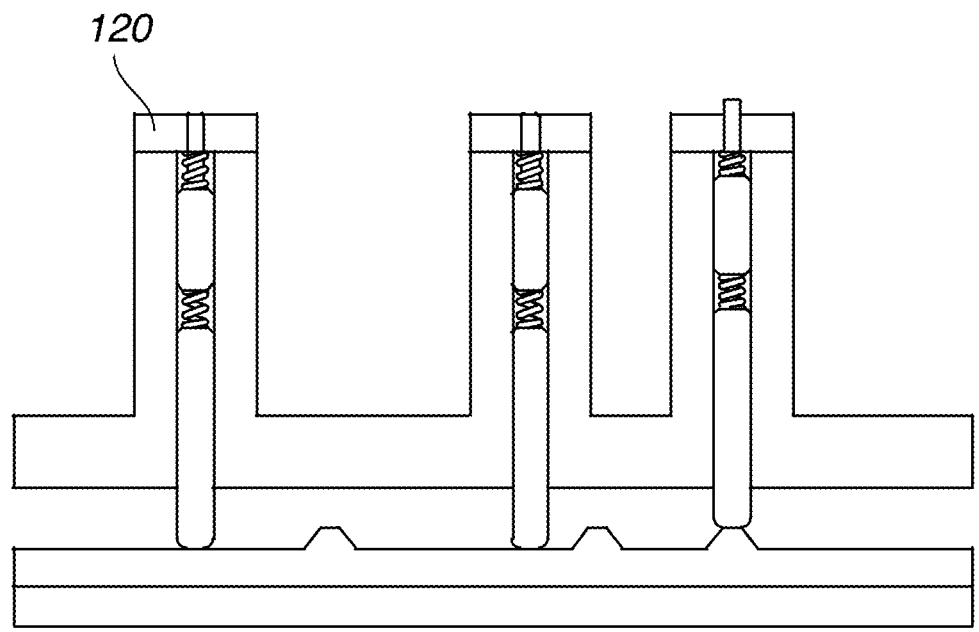
FIGS. 10A and 10B depict embodiments of occlusion of fluidic pathways with the elastomeric layer and a valving mechanism.
Figure 10B:
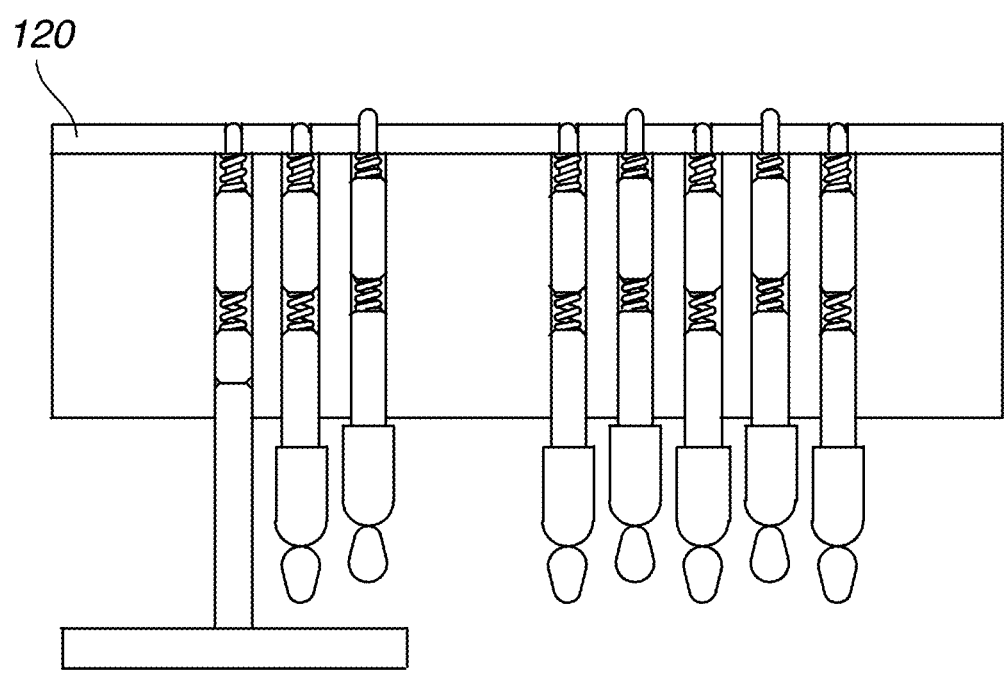

The microfluidic cartridge 100 is preferably configured such that actual valving members are not integrated into the microfluidic cartridge 100; thus, opening and/or occluding portions of a fluidic pathway 165 are performed by systems located external to the microfluidic cartridge. As an example, portions of a fluidic pathway 165 may be opened or occluded at occlusion positions, as described above, by the action of a valving member or mechanism held beneath the card that applies a biasing force to deform the elastomeric layer 140 and occlude a fluidic pathway 165. The force may be applied by a mechanical member (e.g., a pin, post, etc.), an electromechanical member (e.g. a solenoid), a pneumatic or hydraulic member (e.g., air, water, etc.) or any other appropriate means, as shown in FIGS. 10A and 10B. In some variations, the cartridge may include one or more registration regions that allow the card to be aligned with respect to the valving member or mechanism. In alternative embodiments, the elastomeric layer 140, the set of valve guides 127, and the set of occlusion positions 141 may be omitted and replaced with valves integrated within the microfluidic cartridge 100, that are configured to controllably occlude and open portions of a fluidic pathway 165.

Other embodiments of the microfluidic cartridge 100 may further comprise a tag 198 that functions to encode and provide identifying information related to the microfluidic cartridge 100. The tag 198 may comprise a barcode, QR code, or other optical machine-readable tag, or may alternatively be an electronic tag, such as an RFID chip. The identifying information preferably comprises at least information relating to the position of a microfluidic cartridge 100 within a molecular diagnostic system, and information relating to samples analyzed using the microfluidic cartridge 100 (e.g. how many positions remain available for conducting tests). In alternative variations, the tag may relate other information about samples (e.g. sample type, sample volume, sample concentration, date) processed using the microfluidic cartridge 100. Preferably, the tag does not interfere with procedures being performed using the microfluidic cartridge, and is located in an unobtrusive position on the microfluidic cartridge 100, such as a side panel of the microfluidic cartridge 100. Alternatively, the microfluidic cartridge 100 may not comprise a tag 198, and a user or other entity may relate identifying information to the microfluidic cartridge 100 using any appropriate element.

Figure 6A:
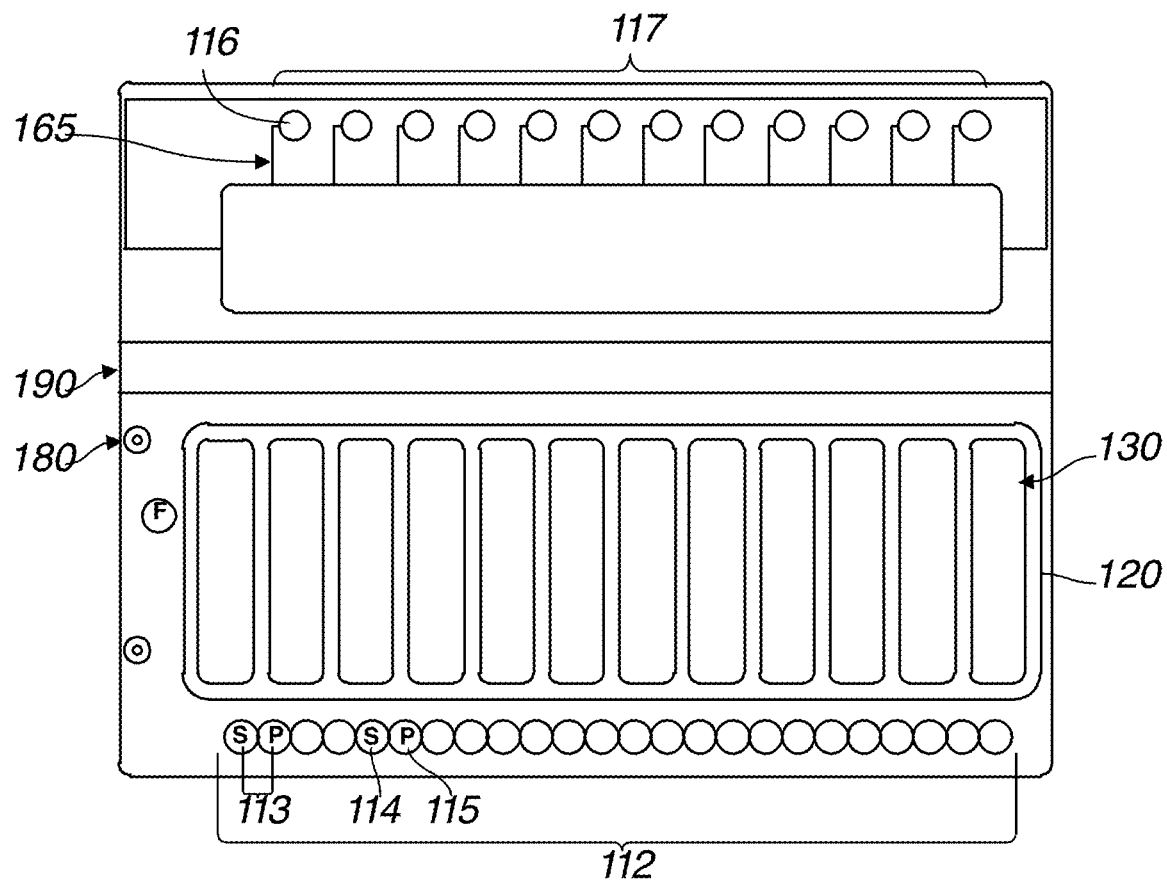
FIGS. 6A-6C depict an alternative embodiment of a microfluidic cartridge (top and side views) and an alternative embodiment of a microfluidic pathway of the microfluidic cartridge.
Figure 6B:
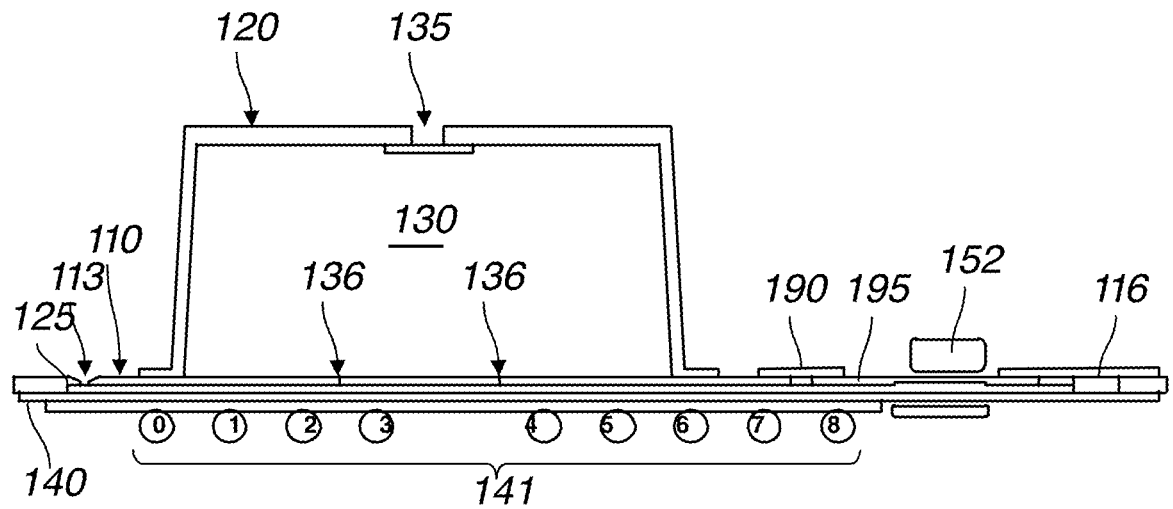
Figure 6C:
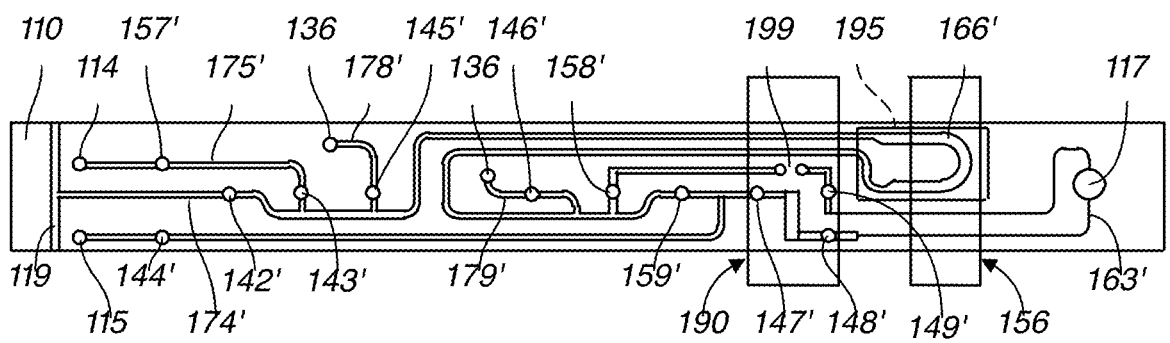
Figure 11A:
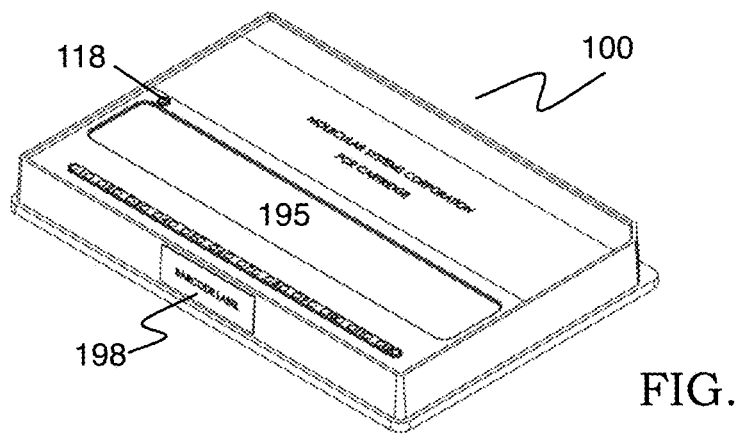
FIGS. 11A and 11B depict an embodiment of the microfluidic cartridge.
Figure 11B:
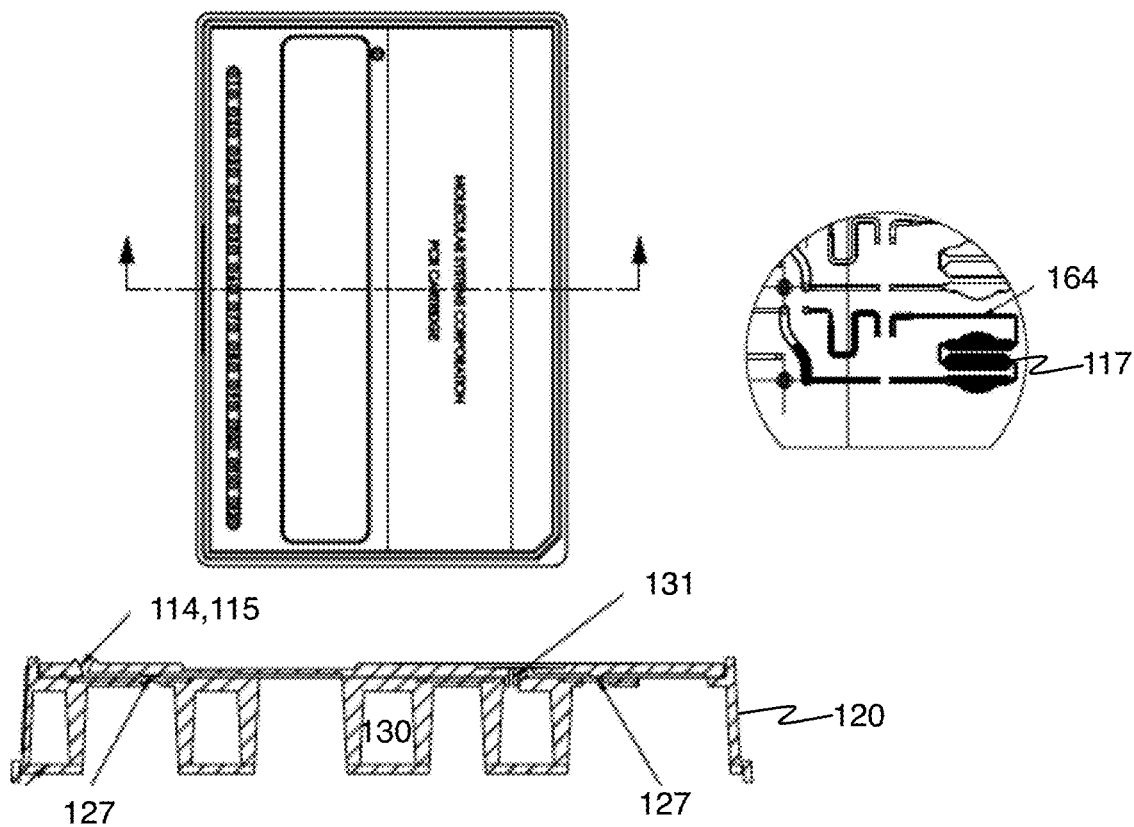

As a person skilled in the art will recognize from the previous detailed description and from the FIGURES and claims, modifications and changes can be made to the preferred embodiments of the microfluidic cartridge 100 without departing from the scope of this invention, as is shown in the example embodiment shown in FIGS. 11A and 11B, and in the alternative example embodiment of FIGS. 6A-6C, wherein in the orientation of FIG. 6B, the intermediate substrate 120 comprising a waste chamber 130 is coupled to the top layer 110, and the elastomeric layer 140 is located on the bottom of the microfluidic cartridge 100.

2. First Specific Embodiment of a Microfluidic Cartridge

The following description a specific embodiment of the microfluidic cartridge 100 is for illustrative purposes only, and should not be construed as definitive or limiting of the scope of the claimed invention.

Figure 14A:
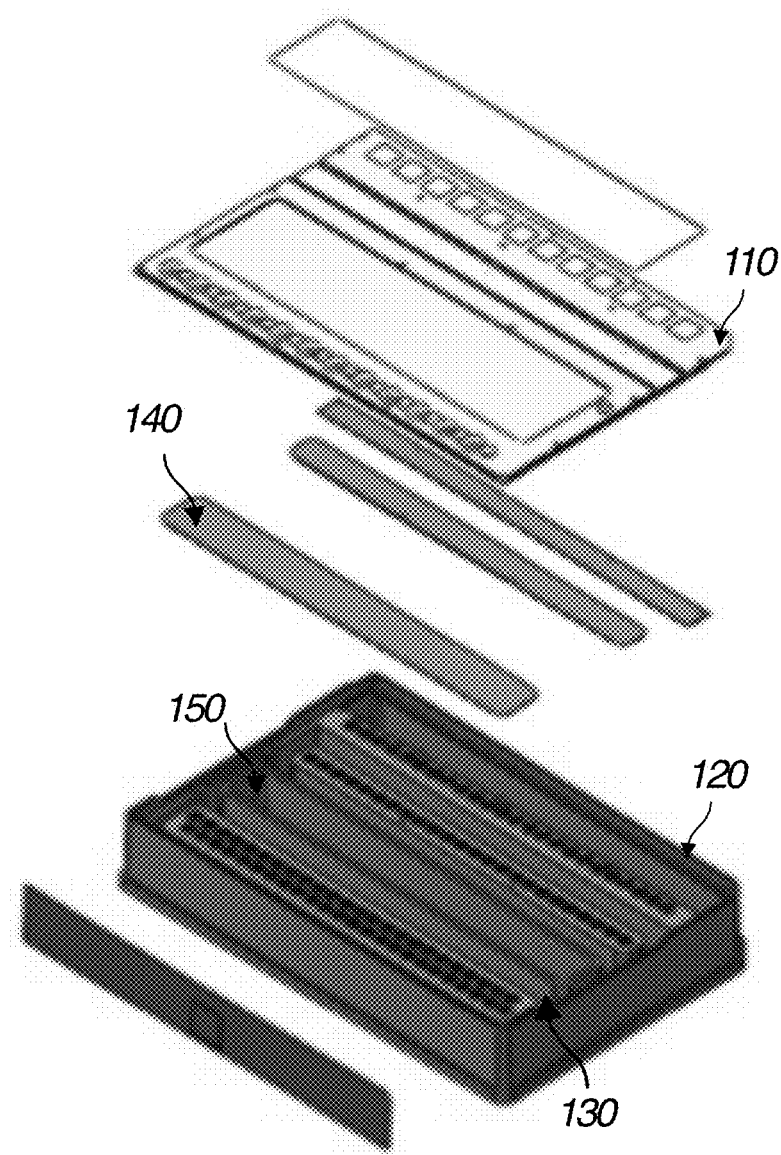
FIGS. 14A-14D depict portions of a specific example of the microfluidic cartridge.
Figure 14B:
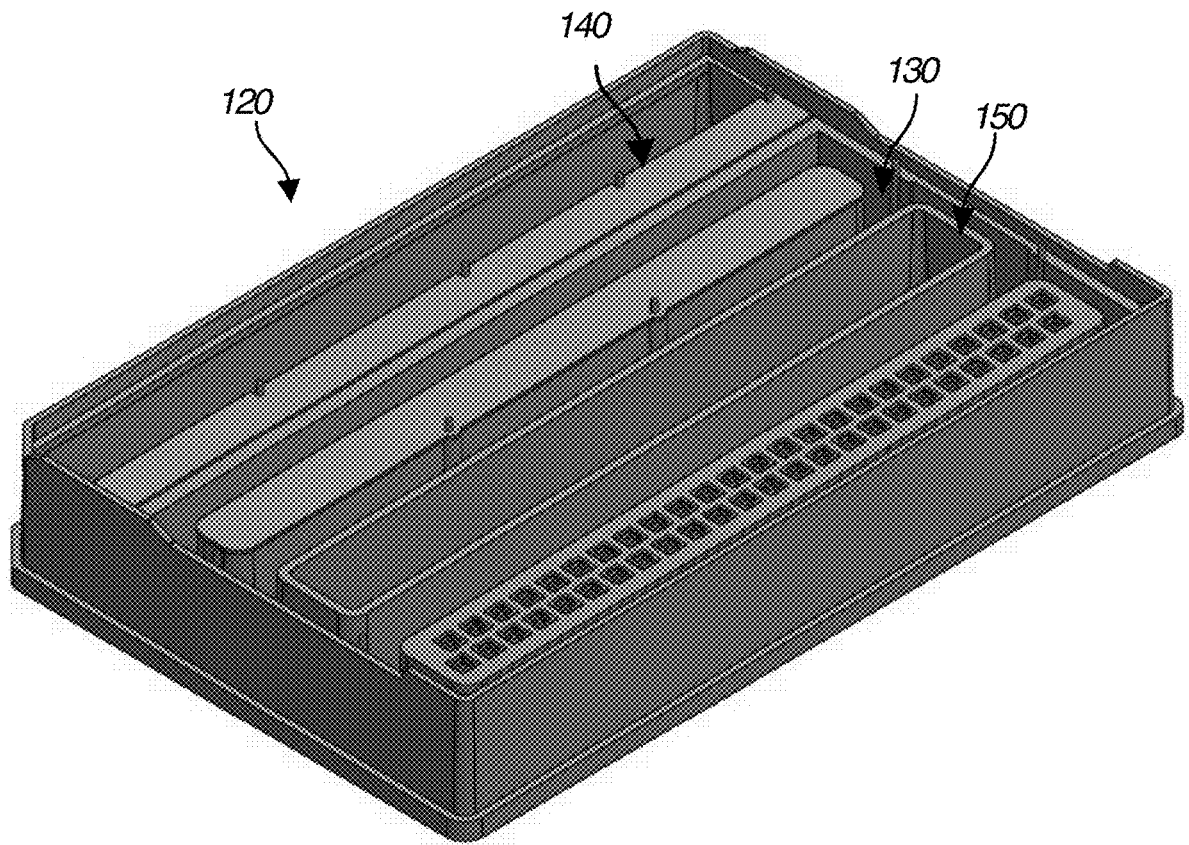

The specific embodiment of the microfluidic cartridge 100 shown in FIGS. 14A-14B includes feature variations which function to perform at least one of the following: improve waste fluid containment), improve valve sealing with elements that use a lower amount of mechanical pressure over the cartridge to form a complete valve seal and provide a buffer against manufacturing imperfections (e.g., as a result of a molding process, as a result of any other process), increase capacity of the waste chamber 130, improve airflow in relation to venting elements, reduce assembly complexity, improve manufacturability (e.g., with elimination of steps and elements that produce bottlenecks and/or require an above threshold amount of handling), and take advantage of advances in automation.

The specific embodiment of the microfluidic cartridge 10000, as shown in FIGS. 14A-14B, meets SLAS ANSI guidelines for a microtiter plate footprint, governing the dimensions of the specific embodiment of the microfluidic cartridge 100. The specific embodiment of the microfluidic cartridge 100 is thus 127.76 mm long and 85.48 mm wide.

The specific embodiment of the microfluidic cartridge 100 comprises a top layer 110 including a set of twelve sample port-reagent port pairs 112, a set of twelve detection chambers 116, a shared fluid port 118, a heating region 195, and a vent region 190; an intermediate substrate 120, coupled to the top layer 110 and partially separated from the top layer 110 by a film layer 125, configured to form a waste chamber 130; an elastomeric layer 140 partially situated on the intermediate substrate 120; a magnet housing region 150 accessible by a magnet 152 providing a magnetic field 156; a bottom layer 170 coupled to the intermediate substrate 120 and configured to seal the waste chamber, and a set of fluidic pathways 160, formed by at least a portion of the top layer 110 and a portion of the elastomeric layer 140, in a manner analogous to that shown (e.g., as in FIGS. 1A-1C) and described.

The top layer 110 of the specific embodiment of the microfluidic cartridge 100 functions preferably as described in Section 1.1, and is composed of polypropylene with low autofluorescence and a glass transition temperature suitable for PCR. The majority of the top layer 110 of the specific embodiment is 1.5 mm thick (aside from regions defining ports, the vent, the heating region 195 or fluidic pathways 165), and is produced by injection molding without the use of a mold release. The polypropylene is clear to allow transmission of light in the detection chambers. The injection molding process defines the set of 12 sample port-reagent port pairs, which are located along one long edge of the top layer 110, and also defines the set of 12 detection chambers 116, which are located along the opposite long edge of the top layer 110. The detection chambers 117 do not completely transect the top layer 110, as shown in FIGS. 11A and 11B. Each detection chamber 117 of the specific embodiment is identical and comprised of three interconnected channels, configured in a circular arrangement, with each of the interconnected channels approximately 0.4 mm deep and 1.6 mm wide at its widest point, resulting in a total volume of ~10 mL for each detection chamber 117. The dimensions of the detection chambers 117 of the specific embodiment are such that the detection chambers 117 facilitate heating from one side (resulting in simpler heater design yet fast cycling given the small depth of the channels). The bottoms of the detection chambers 117 are formed by the film layer 125, which is polypropylene film compatible with PCR (100 microns thick or less) that offers low autofluorescence. The film layer 125 can withstand temperatures up to 120° C. or more.

The fabrication process for the specific example also defines the shared fluid port 118 of the top layer 110 and the vent region 190, which is recessed 0.5 mm into the top surface of the top layer 110 (in the orientation shown in FIGS. 14A-14B), and is covered with a polytetrafluoroethylene membrane, which is hydrophobic, gas permeable, and liquid impermeable. A label is bonded with adhesive to the top layer 110 over the vent region 190, which serves to identify the cartridge and protect the vent region 190. The fabrication process also defines the heating region 195, which is recessed and spans the long dimension of the top layer 110, slightly offset from a midline of the top layer 110. The top layer 110 of the specific embodiment requires approximately 15 grams of polypropylene, and all draft angles for the top layer 110 are a minimum of 4 degrees, as defined by an injection molding process.

Figure 14C:
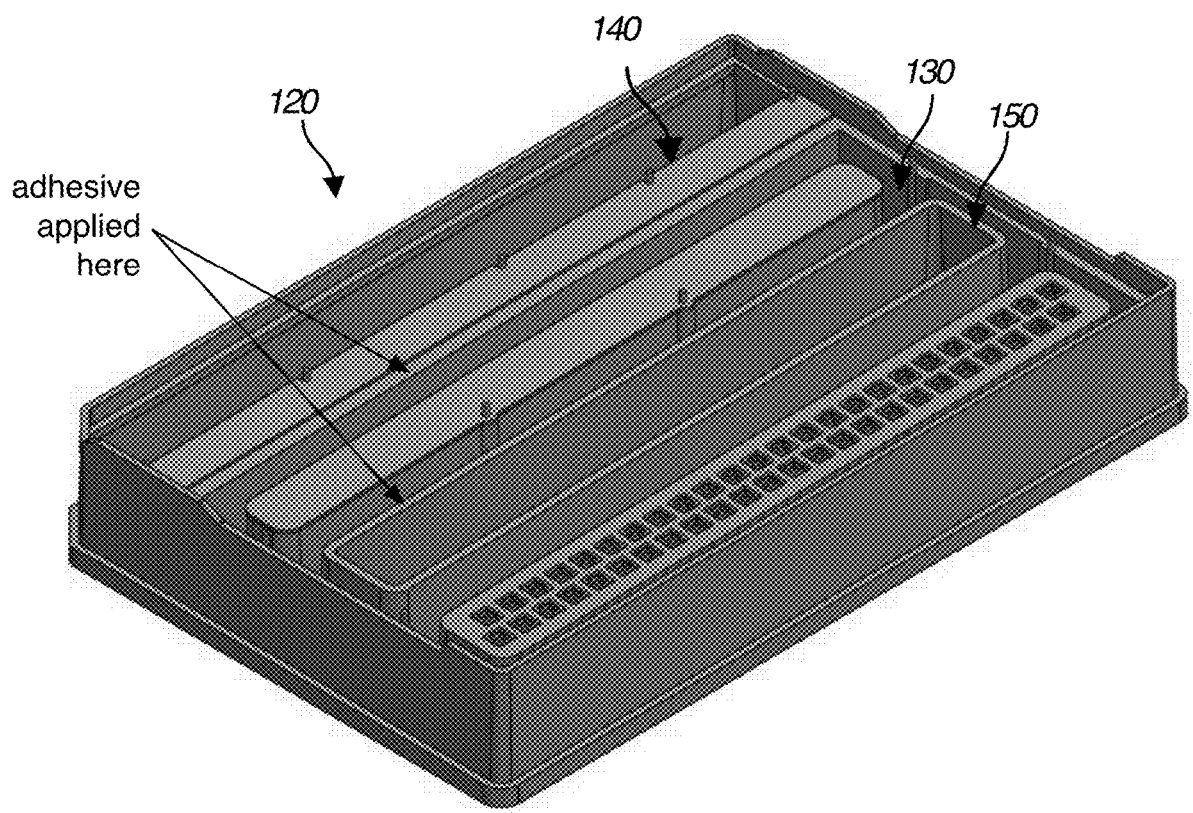

In the specific embodiment, the intermediate substrate 120 is composed of a polypropylene material to minimize cost and simplify assembly, and in the orientation shown in FIGS. 14A-14B, the top of the intermediate substrate 120 is 1.5 mm thick. As shown in FIG. 14C, the specific example includes an adhesive (e.g., silicone glue) at perimeter regions of the intermediate substrate 120 and at a superior planar surface associated with the magnet housing region 150, in order to form a complete seal. Additionally, in the specific example, an inferior region of the intermediate substrate 120 is molded or otherwise bonded to the bottom layer 170 to mitigate risk of leaking through base regions of the cartridge 100.

Figure 14D:
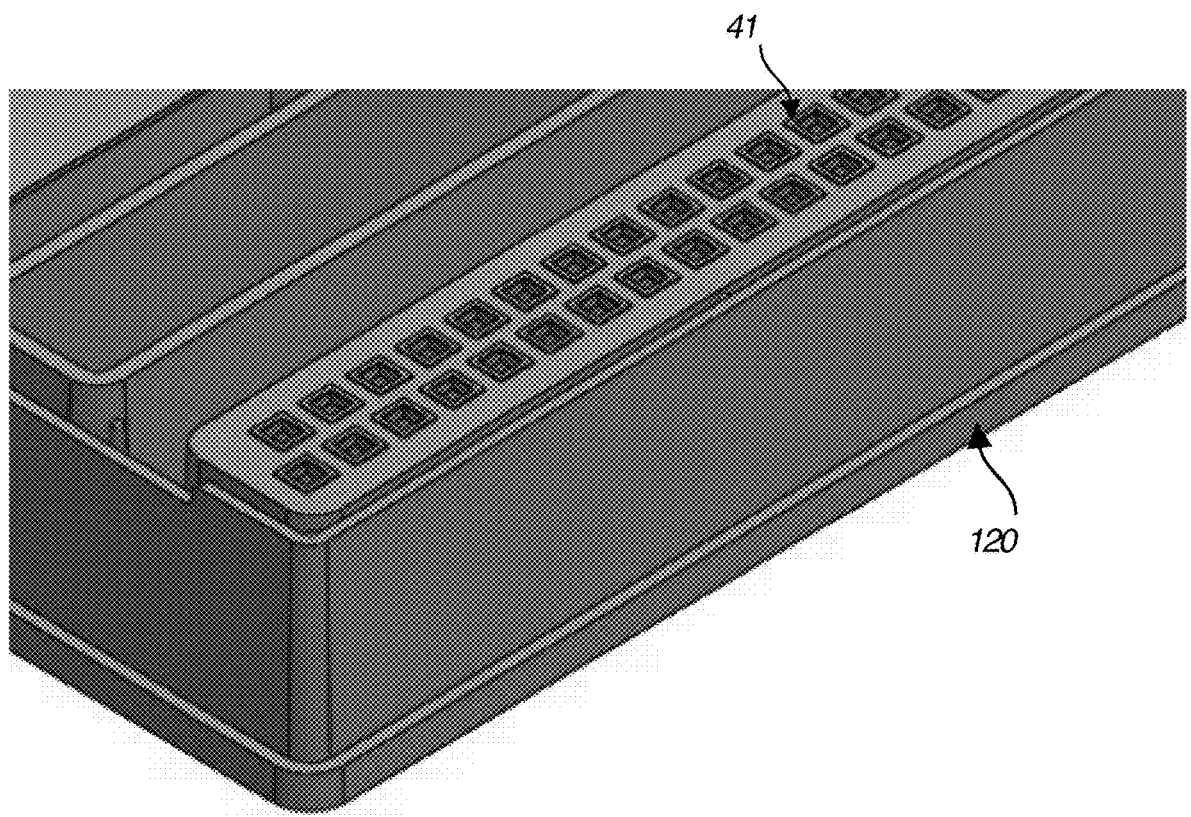

The intermediate substrate 120 also comprises a set of valve guides 127, at a set of occlusion positions 141, which are holes with chamfered edges through the intermediate substrate 127. Each valve guide in the set of valve guides 127 is 2.1 mm×2.1 mm square, and configured to accommodate an occluder with a 2 mm×2 mm square head for normally open positions 42 or 2.1 mm diameter circle to accommodate a 2 mm diameter round pin for normally closed positions 43. The intermediate substrate 120 also comprises a set of sealing features about each of the set of valves/occlusion positions 141, in order to provide pressure concentration and to mitigate effects of manufacturing imperfections. The sealing features 41 comprise protruding boundaries about each of the openings associated with the set of occlusion positions 141, as shown in FIG. 14D, which further compress sheets of the elastomeric layer 140 described in more detail below. In specific examples, the sealing features 41 define a wall with a wall thickness and a height about each opening of the set of occlusion positions 141; however, variations of the specific example can omit the sealing features 41.

The elastomeric layer 140 of the specific embodiment is composed of a low durometer silicone, and comprises strips that are 500 microns thick and that can withstand temperatures of 120° C. at a minimum. The strips of the elastomeric layer 140 are arranged over the set of valve guides 127 and on surfaces of the intermediate substrate 120 adjacent to and surrounding the vent region 190, in order to provide a gap between the intermediate substrate 120 and the top layer 110 to allow for venting during sample processing. The strips of the elastomeric layer 140 can be bonded to the top of the intermediate substrate 120 using a silicone adhesive or any other suitable adhesive. Additionally, the elastomeric layer 140 is slightly compressed between the top layer 110 and the top of the intermediate substrate (in the orientation shown in FIG. 14B).

The bottom layer 170 of the specific embodiment of the microfluidic cartridge 100 is composed of polypropylene, identical to that of the intermediate substrate 120. The bottom layer is 1.5 mm thick, and is contiguous in the area of the set of Detection chambers 116, such that an outer perimeter of the entire bottom layer 170 substantially spans the footprint of the microfluidic cartridge 10000. The bottom layer 170 of the specific embodiment is bonded to the intermediate substrate 120 using polymer adhesive, providing a hermetic seal that ensures that a waste fluid within the waste chamber 130 of the intermediate substrate 120 does not leak out of the waste chamber 130.

The specific embodiment of the microfluidic cartridge 100 comprises twelve fluidic pathways 165 in the set of fluidic pathways 160, such that the microfluidic cartridge 100 is capable of testing up to twelve samples using twelve distinct fluidic pathways 165. Each of the twelve fluidic pathways 165 is coupled to one of the twelve sample port-reagent port pairs 113 on one end of the microfluidic cartridge 100, and coupled to one of the twelve detection chambers 117 on the other end of the microfluidic cartridge, as shown in FIGS. 1A, 1C, 14A, and 14B. Each fluidic pathway 165 is substantially identical (aside from portions connecting to an initial segment 174 fluidically coupled to a fluid channel 119 coupled to a fluid port 118) and identical to the first embodiment of a fluidic pathway described in Section 1.5 and shown in FIG. 1C. Additionally, the microfluidic channels comprising each fluidic pathway 165 are of the first channel type 171 and 500 microns wide by 475 microns deep, aside from the microfluidic channels of the segments leading to and away from the detection chambers 163, 164, the turnabout portions 166, and the vent segments 177. Also, parallel microfluidic channels of the fluidic pathways 165 of the specific embodiment are typically evenly spaced at 2.25 mm (center-to-center).

The fluidic pathways 165 of the specific embodiment are, in their default condition, open at all occlusion positions, aside from the fourth, seventh, and eighth, occlusion positions 145, 148, 149, as shown in FIG. 1C. Furthermore, the s-shaped capture segment 166 of a fluidic pathway of the specific embodiment is configured to have a volume capacity of 22 µL, have a width of 5.5 mm, and weave back and forth over a magnetic field 156, by crossing the magnet housing region 150. The depth of the s-shaped capture segment 166 is 0.4 mm for the 1.6 mm wide channels and 0.475 for the 0.5 mm narrower channel.

The specific embodiment also comprises a barcode tag 198 located on a vertical edge of the microfluidic cartridge 100, as shown in FIG. 14A. Additional features of the specific embodiment of the microfluidic cartridge 100 are shown in FIGS. 14A and 14B.

3. Second Specific Embodiment of a Microfluidic Cartridge

In a variation of the first specific example of the cartridge 100 described above, the cartridge 100, as shown in FIG. 15, includes a top layer 110 including a set of twelve sample port-reagent port pairs 112, a set of twelve detection chambers 116, a shared fluid port 118, a heating region 195, and a vent region 190; an intermediate substrate 120, coupled to the top layer 110 and partially separated from the top layer 110 by a film layer 125, configured to form a waste chamber 130; an elastomeric layer 140 partially situated on the intermediate substrate 120; a magnet housing region 150 accessible by a magnet 152 providing a magnetic field 156; a bottom layer 170 coupled to the intermediate substrate 120 and configured to seal the waste chamber, and a set of fluidic pathways 160, formed by at least a portion of the top layer 110 and a portion of the elastomeric layer 140, in a manner analogous to that shown (e.g., as in FIGS. 1A-IC) and described.

The top layer 110 of this specific example includes features similar to or otherwise identical to those described above in Section 2, but can alternatively have another suitable configuration.

Figure 15:
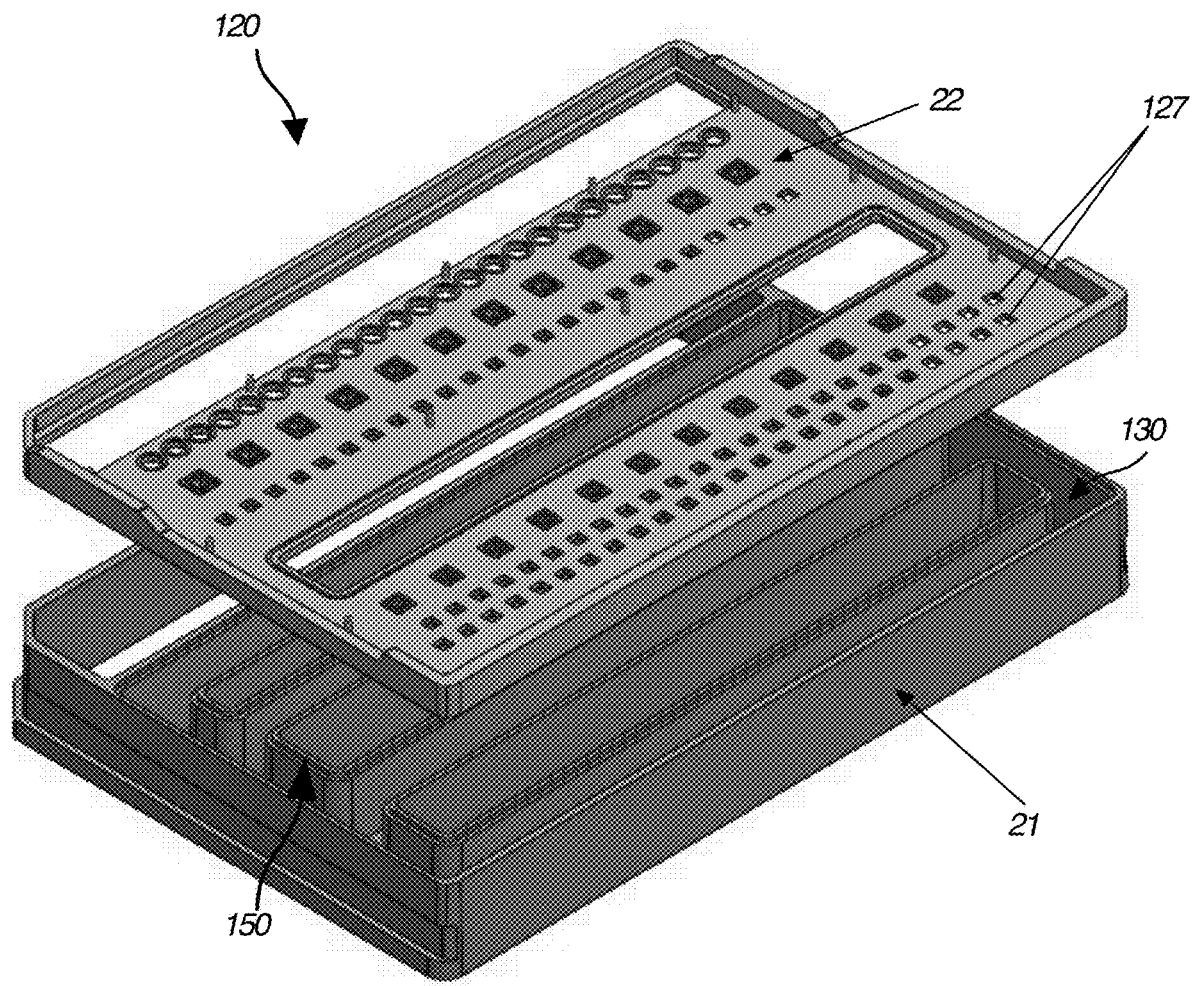
FIG. 15 depicts a specific example of the microfluidic cartridge.

In the specific embodiment, the intermediate substrate 120 is composed of a polypropylene material to minimize cost and simplify assembly, and configured to provide a waste chamber 130 with an increased capacity, that provides full support of the elastomeric layer 140 described below (with embodiments shown in FIGS. 5A-5D and 14A-14C), in relation to providing a fluid seal to prevent leakage of sample processing materials. In this specific embodiment, as shown in FIG. 15, the intermediate substrate comprises two portions: a) a first portion 21 defining a corrugated surface that defines the internal volume of the waste chamber 130 and the magnet housing region 150 and allows access to a set of occlusion positions of the set of fluidic pathways 160 defined in part by the top layer 110 (an embodiment of which is shown in FIG. 9); and b) a second portion 22 defining a set of valve guides 127, at a set of occlusion positions (of which embodiments of occlusion positions of normally open 42 and normally closed 43 occlusion positions are shown in FIG. 1C), which are holes with chamfered edges through the intermediate substrate 127. The second portion 22, in a manner analogous to that described for FIG. 14D, can include a set of sealing features about each of the set of valves/occlusion positions 141, in order to provide pressure concentration and to mitigate effects of manufacturing imperfections. The sealing features 41 shown in FIG. 14D comprise protruding boundaries about each of the openings associated with the set of occlusion positions 141, as shown in FIG. 15, which further compress the elastomeric layer 140 described in more detail below (with embodiments shown in FIGS. 5A-5D and 14A-14C). In specific examples, the sealing features 41 define a wall with a wall thickness and a height about each opening of the set of occlusion positions 41; however, variations of the specific example can omit the sealing features 41.

In this configuration, the first portion 21 and the second portion 22 are bonded together (e.g., physically coextensive) with glue between tongue-and-groove joints 23, as shown in FIG. 15; however, variations of this configuration can include coupling between the first portion 22 and the second portion 23 with any other suitable type of bond (e.g., thermal bond, chemical bond, adhesive bond) and/or any other suitable type(s) of joint(s).

Additionally, in the specific example, the intermediate substrate 120 is co-molded in a simultaneous process with the bottom layer 170 to mitigate risk of leaking through base regions of the cartridge 100, such that the intermediate substrate 120 and the bottom layer 170 are of unitary construction.

The elastomeric layer 140 of the specific embodiment is composed of a low durometer silicone that is 500 microns thick and can withstand temperatures of 120° C. at a minimum. The portions of the elastomeric layer 140 are arranged over the set of valve guides 127 and on surfaces of the intermediate substrate 120 adjacent to and surrounding the vent region 190, in order to provide a gap between the intermediate substrate 120 and the top layer 110 to allow for venting during sample processing. The strips of the elastomeric layer 140 can be bonded to the top of the intermediate substrate 120 using a silicone adhesive or any other suitable adhesive. Additionally, the elastomeric layer 140 is slightly compressed between the top layer 110 and the top of the intermediate substrate (in the orientation shown in FIG. 15), whereby the set of sealing features 41 promote pressure concentration within the elastomeric layer 140 about each of the set of occlusion positions/valve positions.

4. Third Specific Embodiment of a Microfluidic Cartridge

The following description a specific embodiment of the microfluidic cartridge 100 is for illustrative purposes only, and should not be construed as definitive or limiting of the scope of the claimed invention.

The specific embodiment of the microfluidic cartridge 100, as shown in FIGS. 11A and 11B, meets SLAS ANSI guidelines for a microtiter plate footprint, governing the dimensions of the specific embodiment of the microfluidic cartridge 100. The specific embodiment of the microfluidic cartridge 100 is thus 127.76 mm long and 85.48 mm wide.

The specific embodiment of the microfluidic cartridge 100 comprises a top layer 110 including a set of twelve sample port-reagent port pairs 112, a set of twelve Detection chambers 116, a shared fluid port 118, a heating region 195, and a vent region 190; an intermediate substrate 120, coupled to the top layer 110 and partially separated from the top layer 110 by a film layer 125, configured to form a waste chamber 130; an elastomeric layer 140 partially situated on the intermediate substrate 120; a magnet housing region 150 accessible by a magnet 152 providing a magnetic field 156; a bottom layer 170 coupled to the intermediate substrate 120 and configured to seal the waste chamber, and a set of fluidic pathways 160, formed by at least a portion of the top layer 110, a portion of the film layer 125, and a portion of the elastomeric layer 1400.

The top layer 110 of the specific embodiment of the microfluidic cartridge 100 functions preferably as described in Section 1.1, and is composed of polypropylene with low autofluorescence and a glass transition temperature suitable for PCR. The majority of the top layer 110 of the specific embodiment is 1.5 mm thick (aside from regions defining ports, the vent, the heating region 195 or fluidic pathways 165), and is produced by injection molding without the use of a mold release. The polypropylene is clear to allow transmission of light in the detection chambers. The injection molding process defines the set of 12 sample port-reagent port pairs, which are located along one long edge of the top layer 110, and also defines the set of 12 detection chambers 116, which are located along the opposite long edge of the top layer 110. The Detection chambers 117 do not completely transect the top layer 110, as shown in FIGS. 11A and 11B. Each detection chamber 117 of the specific embodiment is identical and comprised of three interconnected channels, configured in a circular arrangement, with each of the interconnected channels approximately 0.4 mm deep and 1.6 mm wide at its widest point, resulting in a total volume of ~10 mL for each detection chamber 117. The dimensions of the detection chambers 117 of the specific embodiment are such that the detection chambers 117 facilitate heating from one side (resulting in simpler heater design yet fast cycling given the small depth of the channels), and also facilitate the injection molding process. The bottoms of the detection chambers 117 are formed by the film layer 125, which is polypropylene film compatible with PCR (100 microns thick or less) that offers low autofluorescence. The film layer 125 can withstand temperatures up to 120° C. or more.

The injection molding process also defines the shared fluid port 118 of the top layer 110, and the vent region 190, which is recessed 0.5 mm into the top surface of the top layer 110 (in the orientation shown in FIG. 11B), and is covered with a polytetrafluoroethylene membrane, which is hydrophobic, gas permeable, and liquid impermeable. A paper label is bonded with adhesive to the top layer 110 over the vent region 190, which serves to identify the cartridge and protect the vent region 190, as shown in FIGS. 11A and 11B. The injection molding process also defines the heating region 195, which is recessed and spans the long dimension of the top layer 110, slightly offset from a midline of the top layer 110. The top layer 110 of the specific embodiment requires approximately 15 grams of polypropylene, and all draft angles for the top layer 110 are a minimum of 4 degrees, as defined by the injection molding process.

In the specific embodiment, the intermediate substrate 120 is composed of a polypropylene material to minimize cost and simplify assembly, and in the orientation shown in FIG. 11B, the top of the intermediate substrate 120 is 1.5 mm thick. The film layer 125, partially separating the intermediate substrate 120 from the top layer 110 is a polypropylene film with a nominal thickness of 50 microns. The film layer 125 is able to withstand temperatures of up to 95° C. encountered during fabrication and during an intended PCR procedure, while being thermally bondable to the top layer 110. The top layer 110 and the film layer 125 are bonded using thermal fusion bonding, and this subassembly is bonded to the intermediate substrate 120 using a polymer adhesive. Additionally, for aligning layers 110, 120, 125 and bonding the top layer 110 to the intermediate substrate 120, plastic studs are configured to extend from the top of the intermediate substrate 120 through die-cut holes in the film layer 125 and injection molded holes in the bottom of the top layer 110. The intermediate substrate also comprises a set of valve guides 127, at a set of occlusion positions 141, which are holes with chamfered edges through the intermediate substrate 127. Each valve guide in the set of valve guides 127 is 2.1 mm×2.1 mm square, and configured to accommodate an occluder with a 2 mm×2 mm square head for normally open positions 42 or 2.1 mm diameter circle to accommodate a 2 mm diameter round pin for normally closed positions 43.

The elastomeric layer 140 of the specific embodiment is composed of a low durometer silicone, and comprises strips that are 500 microns thick and that can withstand temperatures of 120° C. at a minimum. The strips of the elastomeric layer are arranged over the set of valve guides 127, and bonded to the top of the intermediate substrate 120 using a silicone adhesive. Additionally, the elastomeric layer 140 is slightly compressed between the film layer 125 and the top of the intermediate substrate (in the orientation shown in FIG. 11B).

The bottom layer 170 of the specific embodiment of the microfluidic cartridge 100 is composed of polypropylene, identical to that of the intermediate substrate 120. The bottom layer is 1.5 mm thick, and is contiguous in the area of the set of Detection chambers 116, such that an outer perimeter of the entire bottom layer 170 substantially spans the footprint of the microfluidic cartridge 100. The bottom layer 170 of the specific embodiment is bonded to the intermediate substrate 120 using polymer adhesive, providing a hermetic seal that ensures that a waste fluid within the waste chamber 130 of the intermediate substrate 120 does not leak out of the waste chamber 130.

The specific embodiment of the microfluidic cartridge 100 comprises twelve fluidic pathways 165 in the set of fluidic pathways 160, such that the microfluidic cartridge 100 is capable of testing up to twelve samples using twelve distinct fluidic pathways 165. Each of the twelve fluidic pathways 165 is coupled to one of the twelve sample port-reagent port pairs 113 on one end of the microfluidic cartridge 100, and coupled to one of the twelve detection chambers 117 on the other end of the microfluidic cartridge, as shown in FIGS. 11A and 11B. Each fluidic pathway 165 is substantially identical (aside from portions connecting to an initial segment 174 fluidically coupled to a fluid channel 119 coupled to a fluid port 118) and identical to the first embodiment of a fluidic pathway described in Section 1.5 and shown in FIG. 1C. Additionally, the microfluidic channels comprising each fluidic pathway 165 are of the first channel type 171 and 500 microns wide by 475 microns deep, aside from the microfluidic channels of the segments leading to and away from the detection chambers 163, 164, the turnabout portions 166, and the vent segments 177. Also, parallel microfluidic channels of the fluidic pathways 165 of the specific embodiment are typically evenly spaced at 2.25 mm (center-to-center).

The fluidic pathways 165 of the specific embodiment are, in their default condition, open at all occlusion positions, aside from the fourth, seventh, and eighth, occlusion positions 145, 148, 149, as shown in FIG. 1C. Furthermore, the s-shaped capture segment 166 of a fluidic pathway of the specific embodiment is configured to have a volume capacity of 22 µL, have a width of 5.5 mm, and weave back and forth over a magnetic field 156, by crossing the magnet housing region 150. The depth of the s-shaped capture segment 166 is 0.4 mm for the 1.6 mm wide channels and 0.475 for the 0.5 mm narrower channel.

The specific embodiment also comprises a barcode tag 198 located on a vertical edge of the microfluidic cartridge 100, as shown in FIG. 11A. Additional features of the specific embodiment of the microfluidic cartridge 100 are shown in FIGS. 11A and 11B.

5. Assembly Method for an Embodiment of the Microfluidic Cartridge

An embodiment of an assembly method 200 for an embodiment of the microfluidic cartridge 100 is shown in FIGS. 12A-12G. The assembly method 200 preferably comprises aligning the top layer to the film layer and thermally bonding the two, using silicone adhesive to bond the elastomeric layer to the intermediate substrate of the microfluidic cartridge S210; compressing the top layer, the film layer, the elastomeric layer, and the intermediate substrate and bonding the top/film layers to the elastomeric layer/intermediate substrate S220; bonding the intermediate substrate to the bottom layer S230; installing the vents of the vent region S250; and applying labels and packaging S260.

Figure 12A:
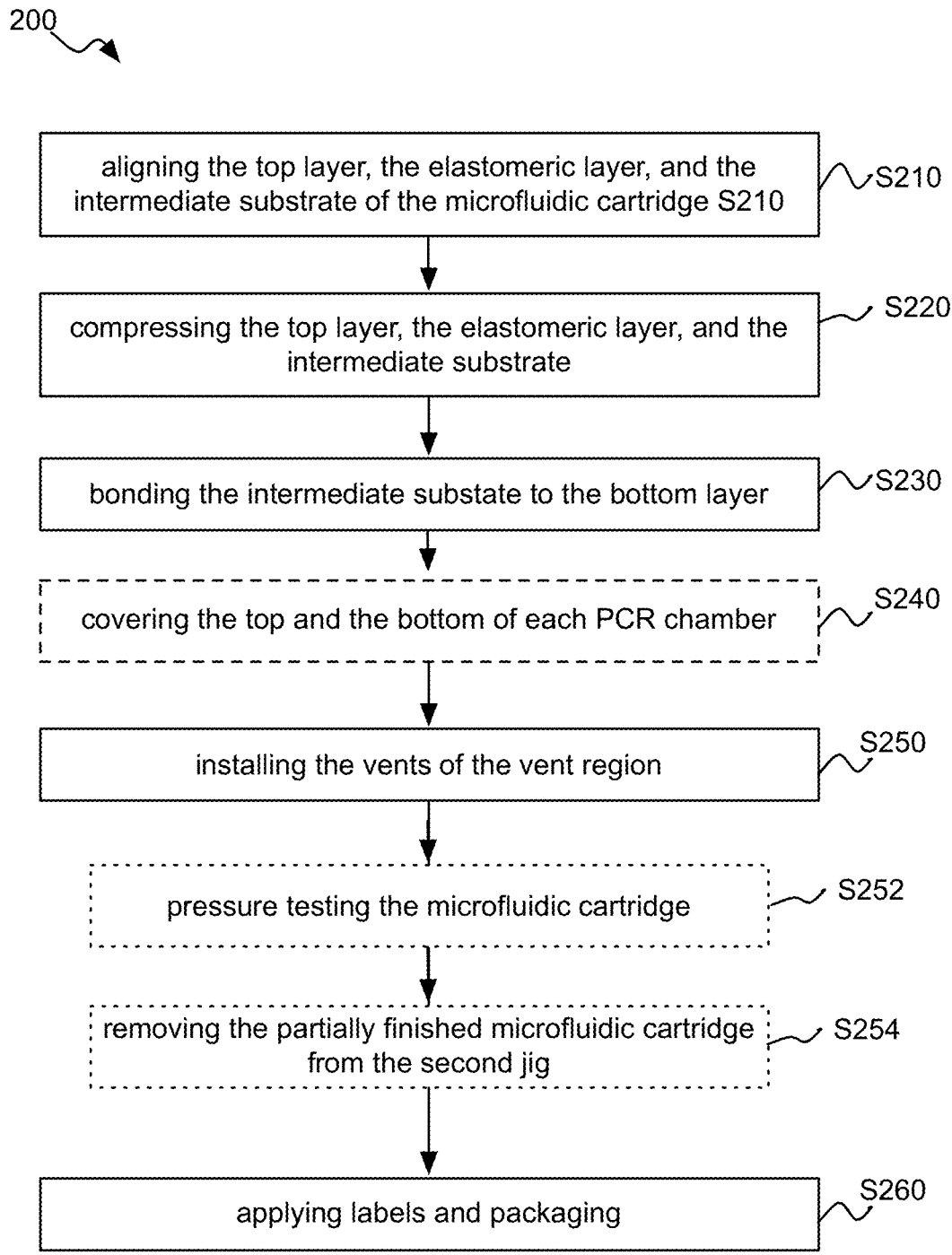
FIGS. 12A-12G depict an example manufacturing method for an embodiment of the microfluidic cartridge.
Figure 12B:
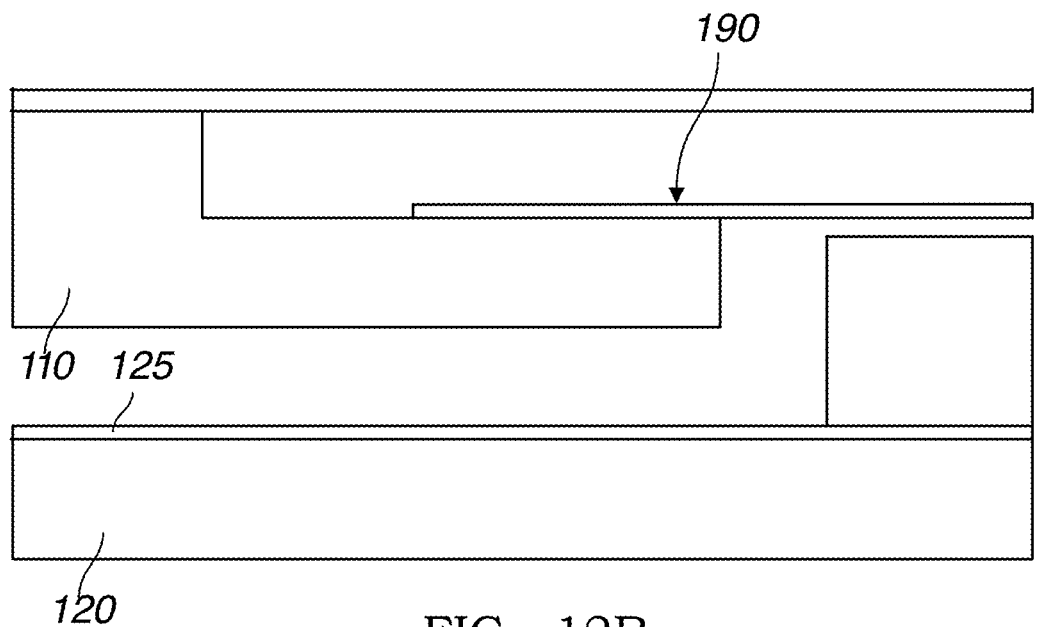
Figure 12C:
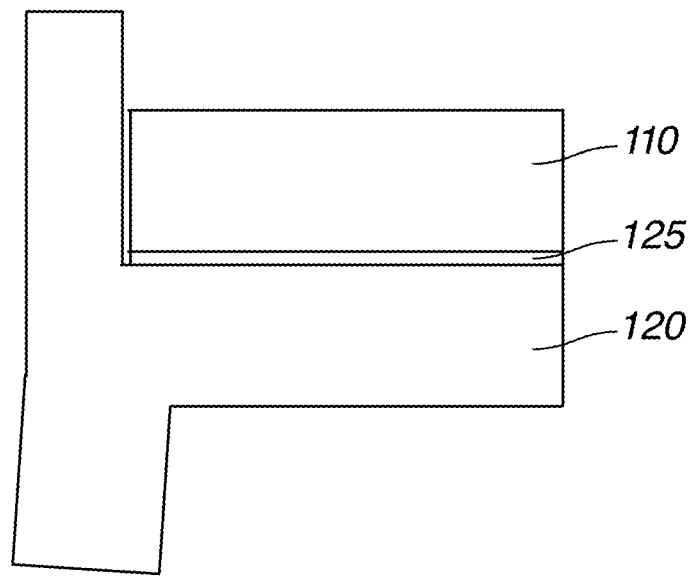
Figure 12D:
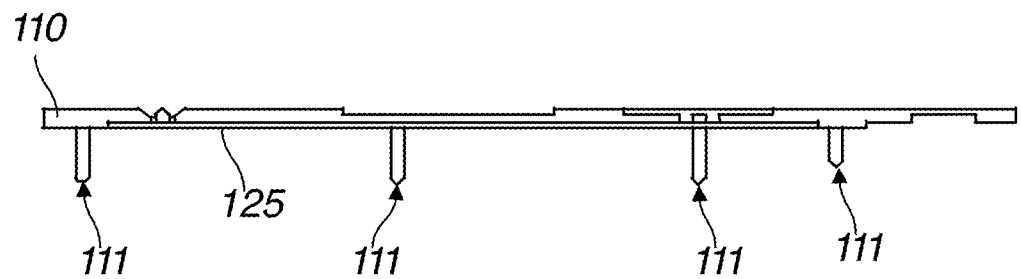
Figure 12E:
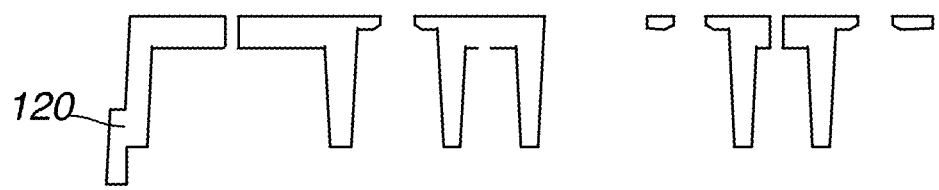
Figure 12F:
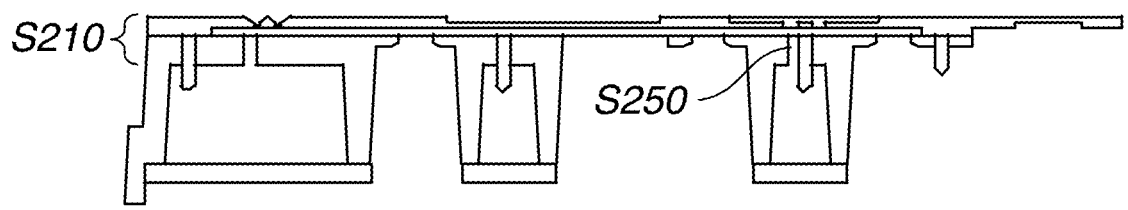

Step S210 recites aligning the top layer to the film layer and thermally bonding the two, using silicone adhesive to bond the elastomeric layer to the intermediate substrate of the microfluidic cartridge, and functions to create a first subassembly comprising the top layer, the film layer, the elastomeric layer, and the intermediate substrate. Preferably, the elastomeric layer is glued with silicone to the intermediate substrate; however, the elastomeric layer may alternatively be solely compressed between the top layer/film layer and the intermediate substrate, without any adhesive. Preferably, a first jig is used to align the top layer and the film layer using pins in the jig and holes in the layers, and in an example embodiment of S210, the top layer is first placed face down in the first jig, and the film layer is placed onto the top layer in preparation for thermal bonding using a lamination machine or hot press. In the example embodiment of S210, the elastomeric layer is then fit over ultrasonic welding tabs 111 of the top layer, as shown in FIGS. 12D and 12F, however, processes other than ultrasonic welding may be used. An adhesive may also be applied around the border of the elastomeric layer, to prevent leakage between the elastomeric layer and the intermediate substrate. Protrusions molded into the top of the intermediate substrate are then passed through alignment holes in the top layer, thus aligning the top layer, the elastomeric layer, and the intermediate substrate of the microfluidic cartridge. In alternative embodiments of S210, any appropriate alignment mechanism may be used to align the top layer, the elastomeric layer, and the intermediate substrate, using for example, a combination of adhesives, frames, and alignment pins/recesses.

Step S220 recites compressing the top layer, the film layer, the elastomeric layer, and the intermediate substrate and bonding the top/film layers to the elastomeric layer/intermediate substrate, and functions to seal the layers in order to prevent leakage between the layers. Preferably, S220 forms hermetic seals between the top layer and the elastomeric layer, and the elastomeric layer and the intermediate substrate, in embodiments of S210 where an adhesive application is involved. In an example embodiment of S220, the first jig with the top layer, the elastomeric layer, and the intermediate substrate is placed within an ultrasonic welder to be compressed and ultrasonically welded.

Figure 12G:
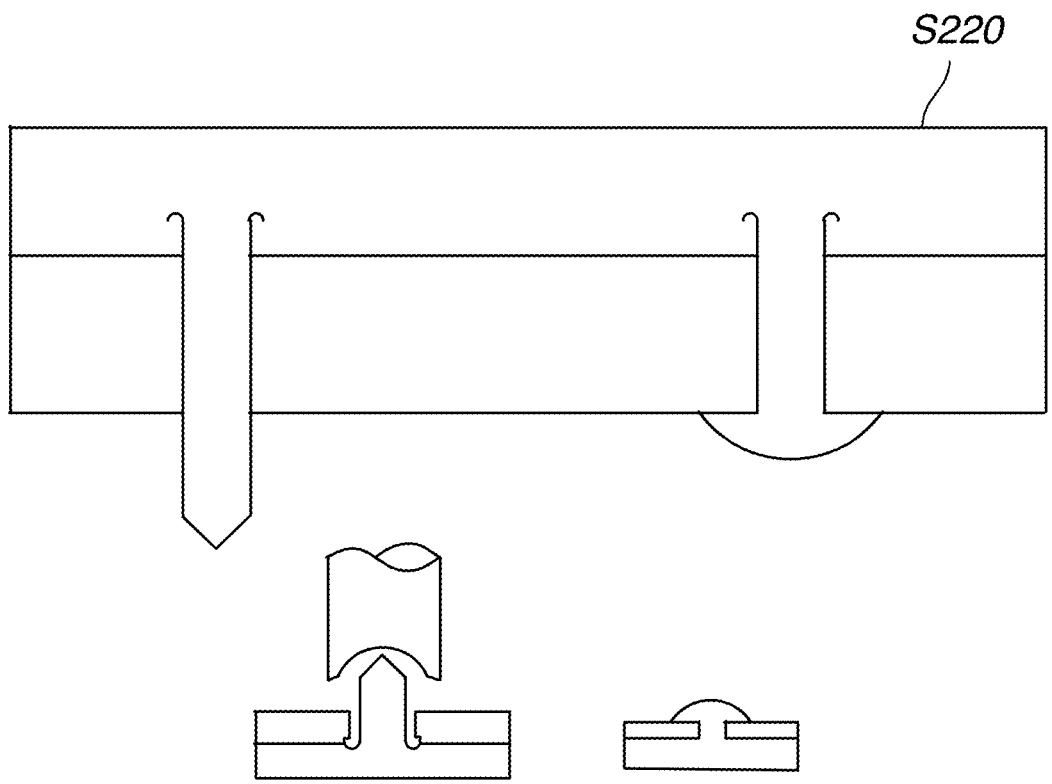

Step S230 recites bonding the intermediate substrate to the bottom layer S230, which functions to form a second subassembly comprising the top layer, the elastomeric layer, the intermediate substrate, and the bottom layer. Preferably, the bottom layer self-aligns with the intermediate substrate as a result of the bottom layer fitting completely inside a recessed flange on the lower portion of the intermediate layer. The bottom layer is preferably thermally bonded to the intermediate layer. Alternatively, the bottom layer may be bonded to the intermediate layer using adhesive or ultrasonic welding, as shown in FIG. 12G.

Step S250 recites installing the vents of the vent region S250, which functions to permanently form the vents of the vent region. Step S250 is preferably performed by heat staking the vents in place, but may alternatively be performed using adhesive or solvent bonding process. Following step S250, the assembly method 200 may further comprise certain quality control measures, including pressure testing the microfluidic cartridge S252 by blocking all sample and reagent ports, and injecting air into the fluid port, and removing the finished microfluidic cartridge from the second jig S254. Step S260 recites applying labels and packaging, and functions to prepare the microfluidic cartridge with identifying information using at least a barcode label, and preparing the microfluidic cartridge for commercial sale.

Figure 13:
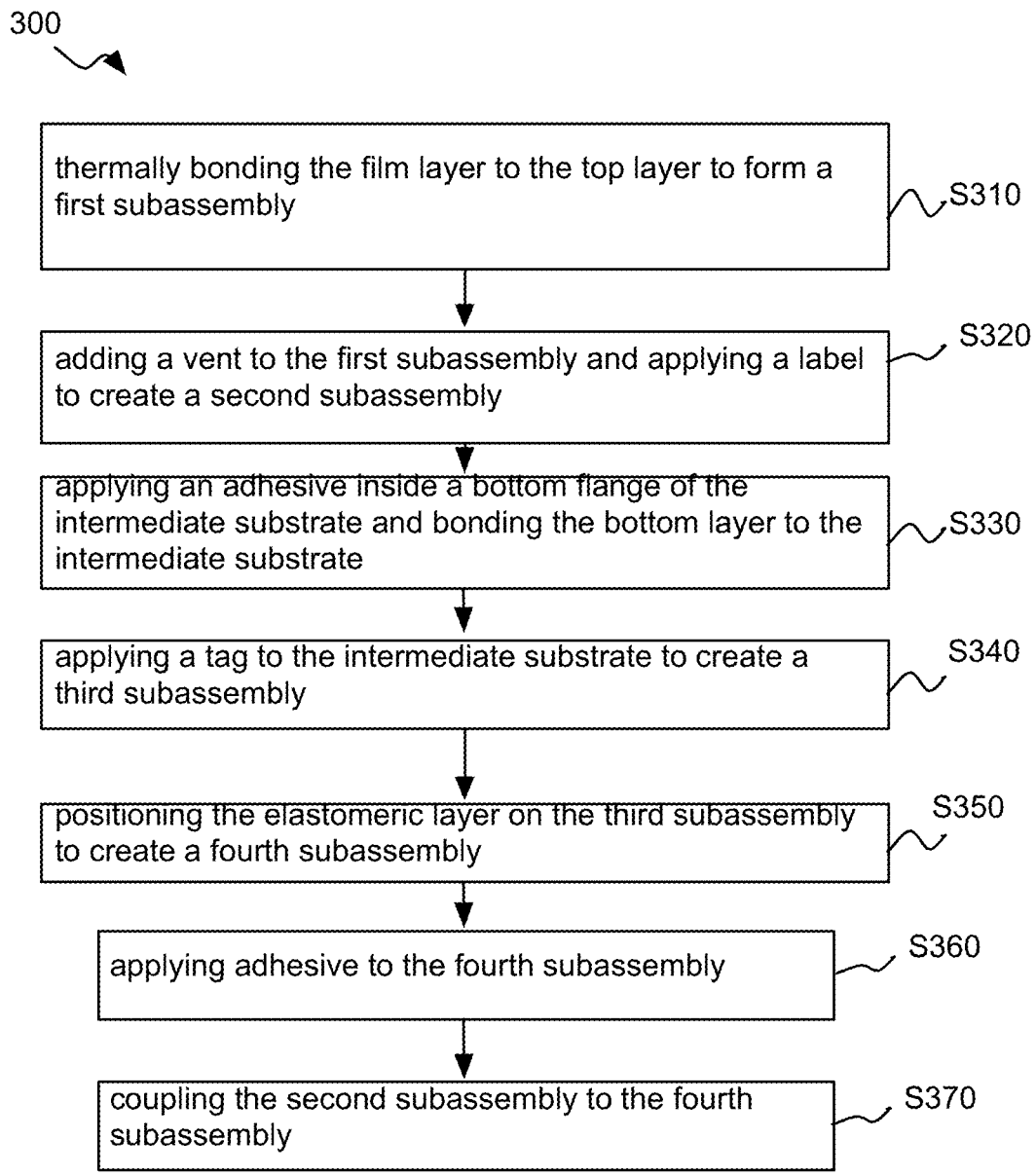
FIG. 13 depicts an alternative example manufacturing method for an embodiment of the microfluidic cartridge.

An alternative embodiment of an assembly method 300, as shown in FIG. 13, comprises thermally bonding the film layer to the top layer to form a first subassembly S310; adding a vent to the first subassembly and applying a label to create a second subassembly S320; applying an adhesive inside a bottom flange of the intermediate substrate and bonding the bottom layer to the intermediate substrate S330; applying a tag to the intermediate substrate to create a third subassembly S340; positioning the elastomeric layer on the third subassembly to create a fourth subassembly S350; applying adhesive to the fourth subassembly S360; and coupling the second subassembly to the fourth subassembly S370.

6. Process Fluid Container

Figure 16A:
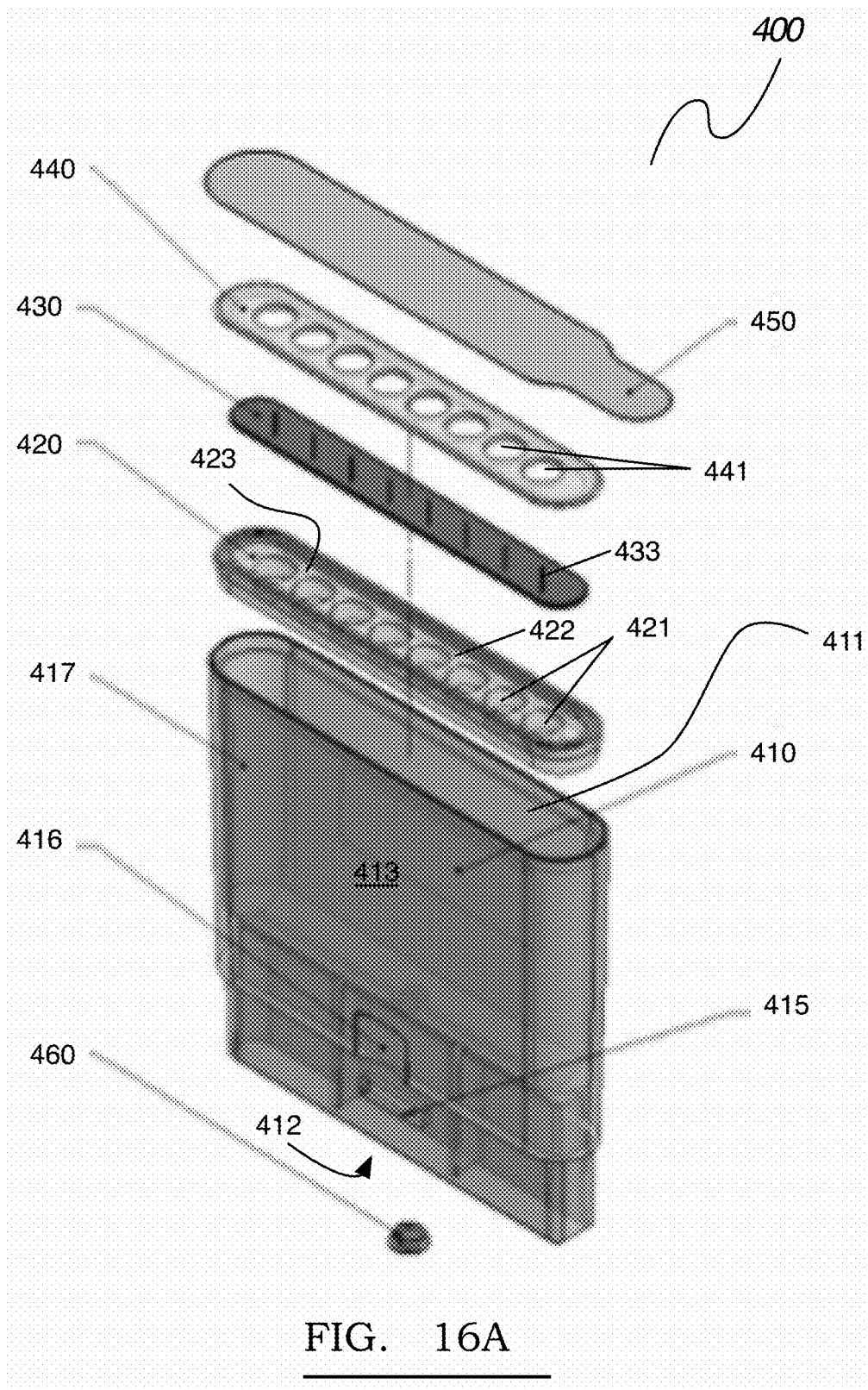
FIGS. 16A-16C depict an embodiment of a process fluid container associated with embodiments of the microfluidic cartridge.

As shown in FIG. 16A, the system 100 can further include or otherwise be associated with a process fluid container 400, which includes: a primary container 410 defining a first opening 411 for accessing at least one process fluid and a second opening 412 for delivering at least one process fluid, and defining an internal volume 413 for retaining at least one process fluid; a first cover 420 reversibly coupleable to the first opening 411 of the primary container 410 and including a set of positioning ports 421 for a set of fluid aspirators, the set of positioning ports 421 defined within a recess 423 of a broad surface 422 of the first cover 420; a septa layer 430 reversibly seated within the recess 423; a septa retainer 440 that includes a set of openings 441 corresponding to the set of positioning ports 421 and that, with the first cover 420, retains the septa layer 430 in position; a second cover 450 that reversibly covers the set of openings 441 of the septa retainer 440; and a stopper 460 that reversibly plugs the second opening 412 of the primary container 410. The process fluid container 400 can, however, include any other suitable elements for retaining process fluids and maintaining them in a desired state.

The process fluid container 400 functions to retain one or more process fluids in a usable state over a desired period of time. In more detail, the process fluid container 400 can perform to promote one or more of the following: minimization of evaporation; minimization of forces required to access process fluid within a sealed container by fluid aspiration/delivery elements (e.g., pipette tips); prevention of the process fluid container 400 from being disturbed by forces created during retraction of fluid aspiration/delivery elements (e.g., pipette tips) from the process fluid container 400; minimization of dead volume within the process container associated with process fluid that is inaccessible to fluid aspiration/delivery elements (e.g., pipette tips); prevention of leakage during shipping and handling of the process fluid container 400; provision of a target region for a marking that allows for easy reading of information contained in the marking by an electronic reader; provision of multiple regions for delivering process fluid to and/or from the process fluid container 400; reduction of physical footprint for the process fluid container 400 within an automated platform; enablement of redundant operations (e.g., in relation to allowing multiple units of process fluid containers to be loaded and/or delivered for sample processing); protection of elements of the process fluid container from oxidation by the process fluid(s) contained; and any other suitable function. Preferably, the process fluid container 400 is configured to be a consumable (i.e., disposable) and intended for a limited number of runs of the system. Alternatively, at least a portion of the process fluid container is configured to be reusable over an indefinite number of runs of the system.

Figure 16B:
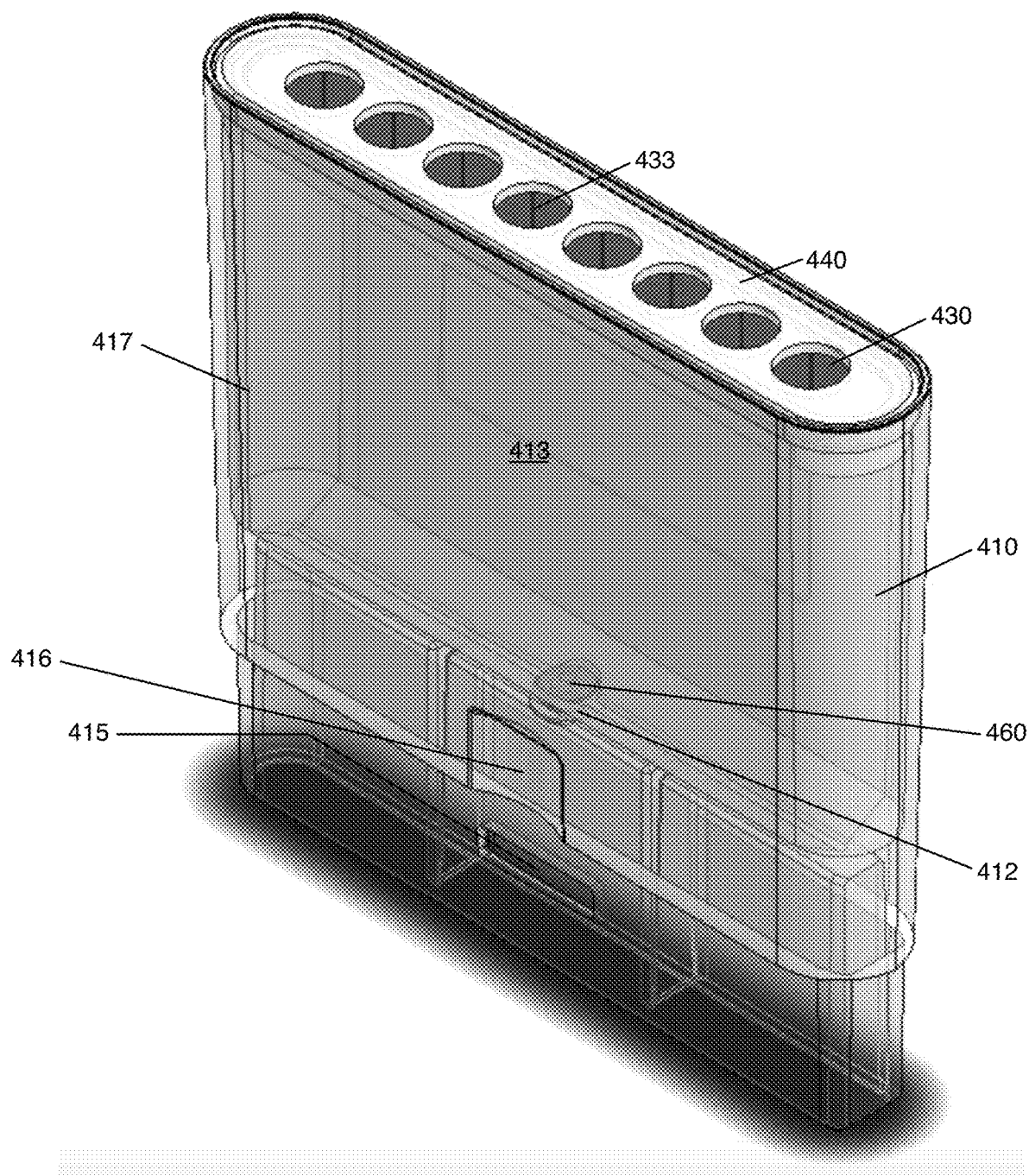

As shown in FIG. 16B, the primary container 410 defines a first opening 411 for accessing at least one process fluid and a second opening 412 for delivering at least one process fluid, and defines an internal volume 413 for retaining at least one process fluid. The primary container functions to retain one or more process fluids, and include multiple openings for facilitating fluid delivery to/from the internal volume 413, and between the internal volume 413 and the microfluidic cartridge 100 described above.

The primary container 410 is preferably configured such that the primary container 400 is capable of resting on a flat surface, provides a target region for a marking that allows for easy reading of information contained in the marking by an electronic reader, provides multiple regions for delivering process fluid to and/or from the process fluid container 400, and reduces physical footprint for the process fluid container 400 within an automated sample processing platform. The primary container 400 is preferably composed of a polymer that is substantially rigid at room temperature (or at any other suitable temperature associated with applications of use), and that can be processed to provide regions of reversible coupling (e.g., mechanical coupling, adhesive coupling, magnetic coupling, etc.) to other elements of the process fluid container 400 described below, but can alternatively be composed of any appropriate material that can contain a fluid and be coupled to other elements.

For a given volume, the primary container 410 preferably has a height greater than its depth and/or width, in order to span a smaller footprint within the automated sample processing platform, in comparison to fluid containers having horizontally distributed arrays of wells. Alternatively, the primary container 410 can have a height that is smaller than its depth and/or width, thereby having a larger footprint within the automated sample processing platform. Still alternatively, the primary container 410 can have any other suitable relationship between its height, depth, and/or width. In variations, the height of the primary container 410 is from 1 cm and 20 cm tall, the depth of the primary container 410 is from 1 cm and 20 cm deep, and the width of the primary container 410 is from 1 cm and 20 cm wide. In relation to dimensions, the primary container 410 can have an internal volume from 1 mL to 8000 mL. However the primary container 410 can alternatively have any other suitable dimensions and/or internal volume.

In relation to the primary container 410, the internal volume 413 can be a continuous, shared bulk volume for a single process fluid (e.g., buffer), or can alternatively include a set of volumes separated by barriers defined by walls of and within the primary container, wherein each of the set of volumes is substantially isolated from the other volumes in the set of volumes to avoid cross contamination. The walls can be liquid-impermeable, gas impermeable, and/or physically impermeable. In one variation, the internal volume 413 can be separated into the set of volumes using a set of vertical walls, wherein the number of volumes in the set of volumes corresponds to the number of positioning ports 421 described in more detail below. Additionally or alternatively, in another variations, individual volumes of the set of volumes can be coupled to each other using fluid pathways (e.g., pathways crossing walls of the set of walls at any suitable region) and/or valved connections. However, separation of individual volumes of the set of volumes can be achieved in any other suitable manner.

Furthermore, in relation to minimizing a dead volume (e.g., inaccessible or otherwise wasted fluid volume) within the primary container 410, the bottom of the primary container 410, in the orientation shown in FIGS. 16A-16B, can include one or more valleys that function to aggregate fluid remaining within the primary container 410 by gravitational force. The primary container can include a single valley at its inferior internal surface, or can alternatively include a set of valleys corresponding to the set of positioning ports 421 described above, such that each of a set of fluid aspirators (e.g., pipette tips) in an array can access the set of valleys to achieve higher aspiration efficiency (e.g., in relation to minimizing waste volume).

As shown in FIG. 16B, the primary container (and/or any other suitable portion of the process fluid container 400) can include a portion 415 of a retention assembly that functions to retain the process fluid container 400 at a desired position during use of the system. The portion 415 of the retention assembly can additionally or alternatively function to hold the primary container in position as a fluid aspiration/delivery element is retracted from the process fluid container 400. The portion 415 of the retention assembly can additionally or alternatively function to provide a coupling point for a module (e.g., robotic device) that couples to the primary container 410/process fluid container 400 and repositions it during performance of a sample processing assay. The portion 415 of the retention mechanism is preferably positioned at an inferior portion of the primary container 410 (e.g., toward the bottom of the primary container); however, the portion 415 of the retention mechanism can alternatively be positioned at any other suitable portion of the process fluid container 400.

In a first variation, the portion 415 of the retention mechanism can be mechanical and can operate by one or more of the following mechanisms: press fit, snap fit, clipping mechanism (e.g., spring-loaded clipping mechanism), hook and loop mechanism (e.g., using Velcro™, etc.), friction-lock, and any other suitable mechanism. In a specific example of this variation, as shown in FIG. 16B, the portion 415 of the retention mechanism includes a slot feature that interfaces with a spring-loaded retainer clip within the sample processing platform in order to retain the process fluid container 400 in position during interactions with a fluid aspirator/delivery element.

In a second variation, the portion 415 of the retention mechanism can be magnetic and include a magnetic feature (e.g., supported by a permanent magnet, supported by an electromagnet, etc.) for coupling to a complementary magnetic feature of the retention mechanism. In additional variations, the portion 415 of the retention mechanism can be associated with any other suitable type of retention mechanism (e.g. adhesive) that allows for retention of the process fluid container 400 in position during use of the system.

In relation to the retention mechanism(s) described in variations above, the primary container 410 and/or any other suitable portion of the process fluid container 400 can include gripping features that facilitate transitioning of the process fluid container 400 from a retained mode to a released mode during use of the system by a user. In a first example, as shown in FIG. 16B, the gripping feature can include a recessed region 416 located proximal to the portion 415 of the retention mechanism described above, wherein the recessed region 416 allows a user to grip the process fluid container 400 (e.g., with his/her thumb) in order to facilitate transitioning of the process fluid container 400 from a retained mode to a released mode during use. However, the gripping features can additionally or alternatively be defined in any other suitable manner (e.g., with a friction pad layer, etc.).

As shown in FIGS. 16A-16B, the primary container 410 and/or any other suitable portion of the process fluid container 400 can include a marking region 417 that functions to provide a target region for a marking that allows for easy reading of information contained in the marking by an electronic reader. In more detail, the marking region can function to decrease the probability of misreads or other reading errors, by promoting proper positioning of any markings within a field of view of an electronic reader. The marking region 416 can be defined by a recess in a broad surface of the primary container 410 or any other suitable portion of the process fluid container 400. However, in variations, the marking region 416 may not be defined by a recess in a broad surface.

The marking associated with the marking region 417 can include one or more of: a label (e.g. a paper label with an adhesive backing, a plastic label with an adhesive backing, a metallic label with an adhesive backing, etc.), a printed marking, an embossed marking, a marking created during a molding process associated with fabrication of the process fluid container, and any other suitable marking. In format, the marking can include one or more of: text characters, non-text characters, images, a bar code, a QR code, and any other suitable content. The content associated with the marking can include sample information (e.g., sample contents, sample source, sample extraction date, sample processing date, sample volume, sample physical characteristics, etc.), sample storage information, sample processing protocol information, process fluid information (e.g., contents, concentrations, physical characteristics, shelf life, time stamp of creation, time stamp of expiration, etc.), process fluid container information (e.g., batch information, available protocol information, etc.), and any other suitable information.

As described above, the process container 400 can include a stopper 460 that reversibly plugs the second opening 412 of the primary container 410. The second opening 412 functions to allow the process fluid container 400 to be filled with a process fluid, and in a specific application, allows the process fluid container 400 to be filled with a process fluid after the primary container 410, the first cover 420, the septa layer 430, the septa retainer 440, and the second cover 450 have been assembled in a manner that seals the first opening 411. In this specific example, the second opening includes a filling opening feature and a sealing flange, which is configured to interface with the stopper 460 to seal the second opening 412 of the primary container 410.

The stopper 460 is preferably composed of a polymeric material, and in a specific example, can be composed of a silicone material. However, the stopper 460 can additionally or alternatively be composed of any other suitable material. In morphology, the stopper 460 preferably comprises a cross section that matches a cross sectional shape of the second opening 412 (e.g., circular, polygonal, ellipsoidal, etc.); however, the stopper 460 can additionally or alternatively define any other suitable shape that promotes sealing of the second opening 412 of the primary container 410. The stopper 460 can taper from a wide base to a narrow base; however, the stopper 460 can alternatively omit a tapering morphology.

The process fluid container 400 also includes a first cover 420 reversibly coupleable to the first opening 411 of the primary container 410 and including a set of positioning ports 421 for a set of fluid aspirators, the set of positioning ports 421 defined within a recess 423 of a broad surface 422 of the first cover 420. The first cover 420 functions to provide a rigid support for the septa layer 430 described in further detail below, and to define regions through which one or more fluid aspirator/delivery elements can access fluid contained within the primary container 410.

Figure 16C:
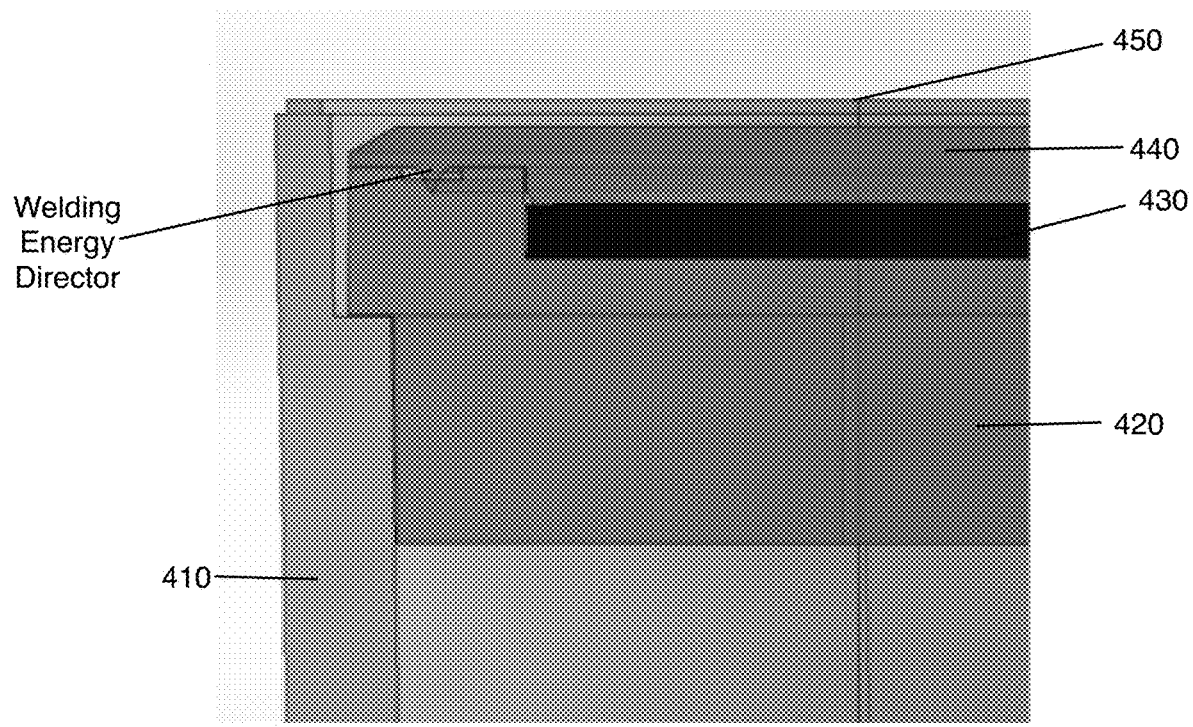

The first cover 420 is preferably composed of a polymeric material (e.g., polyethylene-associated polymer, ABS associated polymer, etc.), but can alternatively be composed of any other suitable material that provides support to the septa layer and fluid aspirator elements (e.g., pipette tips) during use of the system. In particular, the first cover 420 is preferably composed of a material that promotes coupling (e.g., mechanical coupling, thermal coupling, adhesive coupling, etc.) of the first cover 420 at the first opening 411 of the primary container 410. In a specific example, the first cover 420 can be seated within the first opening 411 and coupled together with the primary container 410 at the first opening with a press fit or snap fit (e.g., with supplemental ultrasonic welding as shown in FIG. 16C, with supplemental other thermal bonding techniques, with supplemental adhesive bonding, etc.); however the first cover 420 and the primary container 410 can alternatively be coupled to each other in any other suitable manner.

In relation to leakage prevention, the first cover 420, is preferably mounted below the top boundary of the primary container 410 (in the orientation shown in FIGS. 16A-16C) in a manner that positions the recess 423, the septa layer 430, and the septa retainer 440 sufficiently below the top boundary of the primary container 410. In this regard, the second cover 450 is configured to be separated from the portions of the process fluid container 400 that could leak (e.g., the septa layer, as described in more detail below) if mechanically or otherwise physically disturbed during handling of units of the process fluid container 400.

The set of positioning ports 421 preferably includes circular ports that correspond to a cross sectional shape of associated fluid aspirator/delivery elements used with the system; however, the set of positioning ports 421 can alternatively be defined by any other suitable port shape. In a specific example, as shown in FIG. 16A, the set of positioning ports 421 includes 8 ports; however, the first cover 420 can alternatively include any other suitable number of ports.

The process fluid container 400 also includes a septa layer 430 reversibly seated within the recess 423 of the first cover 420, which functions to reduce evaporation of fluid contents of the process fluid container 400 during use of the system. The septa layer 430 can additionally or alternatively function to reduce forces required to access process fluid within a sealed container by fluid aspiration/delivery elements (e.g., pipette tips). The septa layer 430 is preferably composed of an elastomeric polymer (e.g., silicone) that can be subject to a high degree of elastic deformation and recover to a baseline state. Furthermore, in relation to reducing forces required to access process fluid within a sealed container by fluid aspiration/delivery elements, the septa layer 430 can include surface coatings with low coefficients of friction in order to ease penetration of the septa layer 430 and retraction from the septa layer 430 by fluid aspiration/delivery elements. In a specific example, the septa layer includes coatings of polytetrafluoroethylene at surfaces intended to interface with fluid aspiration/delivery elements, in order to provide low coefficient of friction surfaces for penetration of the septa layer 430 and retraction from the septa layer 430 by fluid aspiration/delivery elements. However, the septa layer 430 can alternatively be composed of any other suitable material(s).

In relation to evaporation reduction, the septa layer 430 preferably includes a set of self-sealing regions that correspond to the set of positioning ports 421, wherein the self-sealing regions can include slits (or other openings) that are normally in a closed state. As such, the septa layer 430 can operate in a baseline sealed mode, whereby the slits are closed, and then transitioned to an unsealed mode upon interacting with one or more fluid aspiration elements that penetrate the self-sealing regions. As such, in the baseline state, the septa layer 430 is sealed in a manner that reduces evaporation of fluid contents of the process fluid container 400.

The slits of the set of self-sealing regions 433, as shown in FIG. 16B, of the septa layer 430 preferably also promote force reduction in relation to access by fluid aspiration/delivery elements. In particular, the force required to penetrate the septa layer 430 is associated with a slit length characteristic; however, slit lengths are limited with respect to orientation of the slit relative to other features of the primary container 410/process fluid container 400. In the specific example shown in FIGS. 16A-16B, the slits are oriented 45 degrees relative to a characteristic longitudinal axis of the septa layer 430 (e.g., 45 degrees from horizontal in the orientation shown in FIG. 16B), in order to maximize the lengths of each slit to reduce forces required for penetration. However, in relation to other process fluid container designs, the slits can be configured in a manner that maximizes length without interference by walls of the primary container 410 or adjacent slits in any other suitable manner.

The process fluid container 400 also includes a septa retainer 440 that includes a set of openings 441 corresponding to the set of positioning ports 421 and that, with the first cover 420, retains the septa layer 430 in position. The septa retainer 440 functions to retain the septa layer 430 in position, and can additionally or alternatively compress the septa layer 430, with the first cover 420. The septa retainer 440 is preferably composed of a polymeric material that can be coupled to the primary container 410 and/or the first cover 420 (e.g., mechanically, thermally, etc.); however, the septa retainer 440 can alternatively be composed of any other suitable material. In configuration, the septa retainer preferably includes openings that correspond in shape and number of the set of positioning ports 421 of the first cover 420; however, the openings can alternatively be configured in any other suitable manner. As shown in the example of FIG. 16C, the septa retainer 440 can be ultrasonically welded to the first cover and/or regions associated with the first opening 411 of the primary container 410, thereby sealing the septa layer 430 against the first cover 420; however, the septa retainer 440 can be coupled with the other elements of the process fluid container 410 in any other suitable sealed manner.

The process fluid container 400 also includes a second cover 450 that reversibly covers the set of openings 441 of the septa retainer 440, and functions to seal, with other elements, the first opening 411 of the primary container 410 until the process fluid container is ready to be used. The second cover preferably includes a first polymer surface and a second surface coupled to the first surface and composed of a material that is readily pierced by fluid aspirator/delivery elements (e.g., pipette tips). The second surface can be metallic (e.g., aluminum foil, tin foil, etc.), can be polymeric, can be natural (e.g., paper), or can alternatively be any other suitable material that is readily pierced by fluid aspirator/delivery elements (e.g., pipette tips). In particular, the first polymer surface preferably has a thick-enough or uniform-enough characterization, such that it adequately protects the second surface of the second cover 450 from more damaging components of the process fluid(s) contained within the process fluid container. In a specific application, the first surface is associated with a polymer coating having no voids (i.e., access points to the second surface by contents of the process fluid container 400), and the second surface is associated with an aluminum foil layer. In this configuration, the aluminum layer is protected from oxidative components (e.g., Guanidine) or other damaging components of the process fluids contained within the process fluid container. In relation to assembly of the process fluid container 400, in a specific example, the primary container 410 can have a landing at a superior surface to which the second cover 450 can be coupled (e.g., by heat sealing); however, the second cover 450 can be coupled to the primary container 410 and/or any other suitable portion of the process fluid container 400 in any other suitable manner.

In a specific example, the process fluid container 400 has a mass of 116.26 grams, has a volume of 116.3 mL, has a surface area of 18797 mm$^2$, and has a suitably low center of gravity to prevent tipping of the process fluid container 400 during use. However, the process fluid container 400 can alternatively have any other suitable morphological, physical, and/or kinematic properties to prevent undesired aspects of use.

7. Conclusion

The FIGURES illustrate the architecture, functionality and operation of possible implementations of methods according to preferred embodiments, example configurations, and variations thereof. It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose systems that perform the specified functions or acts.

As a person skilled in the art will recognize from the previous detailed description and from the figures and claims, modifications and changes can be made to the preferred embodiments of the invention without departing from the scope of this invention defined in the following claims.

We claim:
1. A system for processing a sample, the system comprising a cartridge comprising:
   a first layer comprising a sample port;
      an intermediate substrate that is coupled to the first layer, partially separated from the first layer by a film layer, and configured to form a waste chamber and a waste port into the waste chamber, wherein the waste chamber directly opposes the first layer across the film layer and defines an external void, wherein the intermediate substrate comprises:
         a first portion defining a volume of the waste chamber and the external void,
         a second portion coupled to a superior surface of the first portion and defining a set of valve guides facing the first layer, and
         an elastomeric layer,
         wherein the second portion supports the elastomeric layer, and
         wherein the first portion, the elastomeric layer, and the second portion are configured to seal the waste chamber; and
      a fluidic pathway, comprising a set of occlusion positions corresponding to the set of valve guides and positioned superior to the intermediate substrate and at least partially separated from the waste chamber by a deformable layer, wherein the fluidic pathway is fluidly coupled to the sample port, and wherein the fluidic pathway operates in an occluded mode in which the deformable layer is deformed by an occluder passing through the external void defined by the waste chamber, the occluded mode allowing waste fluid of the sample to be transmitted through the waste port into an interior portion of the waste chamber.

2. The system of claim 1, wherein the fluidic pathway is defined between the first layer and the film layer.

3. The system of claim 1, wherein the cartridge further comprises an adhesive layer between the intermediate substrate and the film layer, wherein the adhesive layer is positioned at a perimeter region of a broad surface of the intermediate substrate and at a magnet housing region of the intermediate substrate.

4. The system of claim 1, wherein the elastomeric layer comprises a set of elastomeric strips.

5. The system of claim 4, wherein the cartridge further comprises a bottom layer physically coextensive with the intermediate substrate and forming a boundary of the waste chamber.

6. The system of claim 1, wherein at least one of the set of valve guides is bounded by a perimeter wall that provides a biasing force against the elastomeric layer.

7. The system of claim 1, further comprising a process fluid container in fluid communication with the cartridge, the process fluid container comprising:
   a primary container defining a first opening for accessing at least one process fluid and a second opening for delivering at least one process fluid, and defining an internal volume for retaining at least one process fluid;
   a first cover reversibly coupleable to the first opening of the primary container and including a set of positioning ports for a set of fluid aspirators, the set of positioning ports defined within a recess of a broad surface of the first cover;

a septa layer reversibly seated within the recess;

a septa retainer that includes a set of openings corresponding to the set of positioning ports and that, with the first cover, retains the septa layer in position;

a second cover that reversibly covers the set of openings of the septa retainer; and a stopper that reversibly plugs the second opening of the primary container.

8. The system of claim 7, wherein the septa layer is composed of an elastomeric material, includes a polytetrafluoroethylene coating, and includes a set of slits passing through a thickness of the septa layer, the set of slits corresponding to the set of positioning ports.

9. A system for processing a sample, the system comprising:

a cartridge comprising:
a first layer comprising a sample port and a fluid port;
an intermediate substrate that is coupled to the first layer and configured to form a waste chamber, wherein the waste chamber directly opposes the first layer and defines an external void; and
a fluidic pathway, superior to the intermediate substrate and at least partially separated from the waste chamber by a deformable layer, wherein the fluidic pathway is fluidly coupled to the sample port and the fluid port, and wherein the fluidic pathway operates in an occluded mode in which the deformable layer is deformed by an occluder passing through the external void defined by the waste chamber; and a process fluid container in fluid communication with the cartridge, the process fluid container comprising:
a primary container defining a first opening for accessing a process fluid and a second opening for delivering the process fluid;
a first cover coupled to the first opening of the primary container and including a set of positioning ports for a set of fluid aspirators, the set of positioning ports defined within a recess of a broad surface of the first cover;
a septa layer reversibly seated within the recess;
a septa retainer that, with the first cover, retains the septa layer in position; and
a stopper that reversibly plugs the second opening of the primary container.

10. The system of claim 9, wherein the cartridge comprises: an adhesive layer between the intermediate substrate and the first layer, wherein the adhesive layer is positioned at a perimeter region of a broad surface of the intermediate substrate and at a magnet housing region of the intermediate substrate; and wherein the deformable layer comprises a set of elastomeric sheets.

11. The system of claim 10, wherein the intermediate substrate comprises a set of openings facing the first layer and corresponding to a set of occlusion positions of the fluidic pathway, and wherein at least one of the set of openings is bounded by a perimeter wall that provides a biasing force against the deformable layer.

12. The system of claim 9, wherein the recess of the first cover is seated below a superior boundary of the primary container, thereby positioning the septa layer and the septa retainer below the superior boundary of the primary container.

13. The system of claim 9, wherein the septa layer of the process fluid container is composed of an elastomeric material, includes a polytetrafluoroethylene coating, and includes a set of slits passing through a thickness of the septa layer, the set of slits corresponding to the set of positioning ports.

14. The system of claim 9, wherein the primary container of the process fluid container further comprises a marking region associated with a marking that contains electronically accessible information associated with sample processing.

15. The system of claim 9, wherein a height dimension of the process fluid container is greater than a depth dimension and a width dimension of the process fluid container.

* * * * *